(12) United States Patent
Li et al.

(10) Patent No.: US 10,266,821 B2
(45) Date of Patent: Apr. 23, 2019

(54) COMPOSITIONS OF ASYMMETRIC INTERFERING RNA AND USES THEREOF

(71) Applicant: 1 GLOBE HEALTH INSTITUTE LLC, Norwood, MA (US)

(72) Inventors: Chiang Jia Li, Cambridge, MA (US); Xiangao Sun, Brookline, MA (US); Harry Rogoff, Norwood, MA (US); Youzhi Li, Westwood, MA (US)

(73) Assignee: 1GLOBE HEALTH INSTITUTE LLC, Norwood, MA (US)

( * ) Notice: Subject to any disclaimer, the term of this patent is extended or adjusted under 35 U.S.C. 154(b) by 52 days.

(21) Appl. No.: 15/081,559

(22) Filed: Mar. 25, 2016

(65) Prior Publication Data

US 2016/0304868 A1 Oct. 20, 2016

Related U.S. Application Data

(62) Division of application No. 12/199,797, filed on Aug. 27, 2008, now Pat. No. 9,328,345.

(60) Provisional application No. 61/038,954, filed on Mar. 24, 2008, provisional application No. 61/029,753, filed on Feb. 19, 2008, provisional application No. 60/968,257, filed on Aug. 27, 2007.

(51) Int. Cl.
*C12N 15/113* (2010.01)
*A61K 48/00* (2006.01)
*C12N 15/11* (2006.01)

(52) U.S. Cl.
CPC .......... *C12N 15/113* (2013.01); *C12N 15/111* (2013.01); *C12N 2310/14* (2013.01); *C12N 2310/141* (2013.01); *C12N 2310/315* (2013.01); *C12N 2310/321* (2013.01); *C12N 2310/531* (2013.01); *C12N 2320/30* (2013.01); *C12N 2320/53* (2013.01); *C12N 2330/51* (2013.01)

(58) Field of Classification Search
CPC .......... C12N 2310/14; C12N 2310/315; C12N 2310/321; C12N 2310/322; C12N 2310/344; C12N 2310/3521
USPC ....... 435/6.1, 91.1, 91.31, 455, 458; 514/44; 536/23.1, 24.2, 24.5
See application file for complete search history.

(56) References Cited

U.S. PATENT DOCUMENTS

| | | | |
|---|---|---|---|
| 6,962,944 B2 | 11/2005 | Jiang et al. | |
| 7,074,824 B2 | 7/2006 | Jiang et al. | |
| 7,078,196 B2 | 7/2006 | Tuschl et al. | |
| 8,058,255 B2 | 11/2011 | Ford et al. | |
| 8,895,721 B2 | 11/2014 | Tuschl et al. | |
| 9,328,345 B2 | 5/2016 | Li et al. | |
| 2003/0091639 A1 | 5/2003 | Jiang et al. | |
| 2004/0071775 A1 | 4/2004 | Jiang et al. | |
| 2004/0229266 A1 | 11/2004 | Tuschl et al. | |
| 2005/0203047 A1 | 9/2005 | Thomann et al. | |
| 2005/0255487 A1 | 11/2005 | Khvorova et al. | |
| 2005/0266552 A1 | 12/2005 | Doench et al. | |
| 2006/0069050 A1* | 3/2006 | Rana ..................... C12N 15/111 514/44 A |
| 2006/0142228 A1 | 6/2006 | Ford et al. | |
| 2006/0211642 A1* | 9/2006 | McSwiggen ....... C12N 15/1131 514/44 A |
| 2007/0042983 A1 | 2/2007 | Haeberli et al. | |
| 2009/0208564 A1 | 8/2009 | Li et al. | |
| 2010/0286378 A1 | 11/2010 | Li et al. | |

FOREIGN PATENT DOCUMENTS

| | | |
|---|---|---|
| EP | 2193140 A2 | 6/2010 |
| WO | WO 03011224 A2 | 2/2003 |
| WO | WO2003011224 A3 | 5/2003 |
| WO | WO 2005/079533 A2 | 9/2005 |
| WO | WO 2005/089287 A2 | 9/2005 |
| WO | WO2005079533 A2 | 9/2005 |
| WO | WO-2005089287 A2 | 9/2005 |
| WO | WO-2009029688 A2 | 3/2009 |
| WO | WO-2009029688 A3 | 3/2009 |
| WO | WO-2009029690 A1 | 3/2009 |
| WO | WO 2009/078685 A2 | 6/2009 |
| WO | WO2009078685 A3 | 9/2009 |
| WO | WO 2015/139044 A1 | 9/2015 |
| WO | WO2015139044 A1 | 9/2015 |

OTHER PUBLICATIONS

Takei et al., "A Small Interfering RNA Targeting Vascular Endothelial Growth Factor as Cancer Therapeutics" Cancer Res. (2004) 64(10): 3365-3370.
Woodle et al., "Sterically Stabilized Polyplex: Ligand-Mediated Activity" J. Control. Release. (2001) 74(1-3):309-11.
Woodle et al. "Nanoparticles Deliver RNAi Therapy" Materials Today (2005) Issue 8, Suppl. 8:34-41.
Xiang, S., et al., "Short hairpin RNA-expressing bacteria elicit RNA interference in mammals" Nature Biotechnology (2006) 24:697-702.
Zamore, P.D. and Aronin, N., "siRNAs knock down hepatitis" Nature Medicine (2003) 9:266-267.
Zamore, P.D., et al., "RNAi: double-stranded RNA direct the ATP-dependent cleavage of mRNA at 21 to 23 nucleotide intervals" Cell (2000) 101:25-33.

(Continued)

*Primary Examiner* — Jane J Zara
(74) *Attorney, Agent, or Firm* — Milstein Zhang & Wu LLC; Duan Wu, Esq.

(57) ABSTRACT

The present invention provides asymmetrical duplex RNA molecules that are capable of effecting sequence-specific gene silencing. The RNA molecule comprises a first strand and a second strand. The first strand is longer than the second strand. The RNA molecule comprises a double-stranded region formed by the first strand and the second strand, and two ends independently selected from the group consisting of 5'-overhang, 3'-overhang, and blunt end. The RNA molecules of the present invention can be used as research tools and/or therapeutics.

32 Claims, 26 Drawing Sheets

Specification includes a Sequence Listing.

(56) References Cited

OTHER PUBLICATIONS

Zhang, B., and Farwell, M.A., "microRNAs: A new emerging class of players for disease diagnostics and gene therapy" J Cell Mol. Med. (2008) 12(2):3-21.
Zhang, H.Y., et al., "RNA Interference with chemically modified siRNA" Current Topics in Medicinal Chemistry (2006) 6:893-900.
"U.S. Appl. No. 12/199,797, Advisory Action dated Feb. 6, 2014", 7 pgs.
"U.S. Appl. No. 12/199,797, Advisory Action dated Sep. 4, 2015", 3 pgs.
"U.S. Appl. No. 12/199,797, Examiner Interview Summary dated Jun. 25, 2015", 3 pgs.
"U.S. Appl. No. 12/199,797, Final Office Action dated Mar. 27, 2015", 16 pgs.
"U.S. Appl. No. 12/199,797, Final Office Action dated Apr. 14, 2011", 15 pgs.
"U.S. Appl. No. 12/199,797, Final Office Action dated Jul. 24, 2013", 22 pgs.
"U.S. Appl. No. 12/199,797, Non Final Office Action dated Sep. 28, 2010", 14 pgs.
"U.S. Appl. No. 12/199,797, Non Final Office Action dated Nov. 2, 2012", 16 pgs.
"U.S. Appl. No. 12/199,797, Non Final Office Action dated Nov. 16, 2015", 9 pgs.
"U.S. Appl. No. 12/199,797, Notice of Allowance dated Nov. 28, 2015", 9 pgs.
"U.S. Appl. No. 12/199,797, Preliminary Amendment filed Dec. 23, 2008", 3 pgs.
"U.S. Appl. No. 12/199,797, Response filed Jan. 16, 2012 to Final Office Action dated Apr. 14, 2011", 16 pgs.
"U.S. Appl. No. 12/199,797, Response filed Jan. 24, 2014 to Final Office Action dated Jul. 24, 2013", 14 pgs.
"U.S. Appl. No. 12/199,797, Response filed May 2, 2013 to Non Final Office Action dated Nov. 2, 2012", 13 pgs.
"U.S. Appl. No. 12/199,797, Response filed Jul. 30, 2010 to Restriction Requirement dated Jun. 30, 2010", 7 pgs.
"U.S. Appl. No. 12/199,797, Response filed Aug. 25, 2014 to Advisory Action dated Feb. 6, 2014", 15 pgs.
"U.S. Appl. No. 12/199,797, Response filed Aug. 27, 2015 to Final Office Action dated Mar. 27, 2015", 12 pgs.
"U.S. Appl. No. 12/199,797, Response filed Sep. 25, 2015 to Advisory Action dated Sep. 4, 2015", 12 pgs.
"U.S. Appl. No. 12/199,797, Response filed Nov. 24, 2015 to Non Final Office Action dated Nov. 16, 2015", 10 pgs.
"U.S. Appl. No. 12/199,797, Response filed Dec. 28, 2010 to Non Final Office Action dated Sep. 28, 2010", 14 pgs.
"U.S. Appl. No. 12/199,797, Restriction Requirement dated Jun. 30, 2010", 10 pgs.
"U.S. Appl. No. 12/675,620, Final Office Action dated Jan. 23, 2012", 7 pgs.
"U.S. Appl. No. 12/675,620, Non Final Office Action dated Mar. 14, 2014", 14 pgs.
"U.S. Appl. No. 12/675,620, Non Final Office Action dated Dec. 23, 2010", 10 pgs.
"U.S. Appl. No. 12/675,620, Preliminary Amendment filed Feb. 26, 2010", 2 pgs.
"U.S. Appl. No. 12/675,620, Response filed May 23, 2011 to Non Final Office Action dated Dec. 23, 2010", 78 pgs.
"U.S. Appl. No. 12/675,620, Response filed Sep. 17, 2012 to Final Office Action dated Jan. 23, 2012", 14 pgs.
"U.S. Appl. No. 12/675,620, Supplemental Preliminary Amendment filed Jul. 26, 2010", 2 pgs.
"Canadian Application Serial No. 2,735,166, Office Action dated Dec. 27, 2017", 6 pgs.
"European Application Serial No. 08798830.9, Communication Pursuant to Article 94(3) EPC dated Mar. 25, 2013", 4 pgs.
"European Application Serial No. 08798830.9, Extended European Search Report dated Dec. 2, 2011", 5 pgs.
"European Application Serial No. 08798830.9, Response filed Oct. 18, 2012 to Extended European Search Report dated Dec. 2, 2011", 7 pgs.
"European Application Serial No. 08828867.5, Communication Pursuant to Article 94(3) EPC dated Jan. 5, 2016", 4 pgs.
"European Application Serial No. 08828867.5, Communication Pursuant to Article 94(3) EPC dated Jul. 10, 2014", 4 pgs.
"European Application Serial No. 08828867.5, Communication Pursuant to Article 94(3) EPC dated Nov. 2, 2012", 5 pgs.
"European Application Serial No. 08828867.5, Extended European Search Report dated Jun. 14, 2011", 8 pgs.
"European Application Serial No. 08828867.5, Intention to grant dated Jun. 20, 2016", 6 pgs.
"European Application Serial No. 08828867.5, Office Action dated Sep. 11, 2012", 1 pg.
"European Application Serial No. 08828867.5, Response filed Jan. 12, 2012 to Extended European Search Report dated Jun. 14, 2011", 7 pgs.
"European Application Serial No. 08828867.5, Response filed Jan. 25, 2016 to Communication Pursuant to Article 94(3) EPC dated Jan. 5, 2016", 32 pgs.
"European Application Serial No. 08828867.5, Response filed Apr. 9, 2015 to Communication Pursuant to Article 94(3) EPC dated Jul. 10, 2014", 8 pgs.
"European Application Serial No. 08828867.5, Response filed Oct. 22, 2012 to Office Action dated Sep. 11, 2012", 3 pgs.
"European Application Serial No. 08828867.5, Response filed Oct. 31, 2013 to Communication Pursuant to Article 94(3) EPC dated Nov. 2, 2012", 12 pgs.
"European Application Serial No. 08828867.5, Summons to Attend Oral Proceedings dated Jul. 31, 2015", 4 pgs.
"European Application Serial No. 08828867.5, Written Submission filed Dec. 17, 2015", 43 pgs.
"European Application Serial No. 16187862.4, Extended European Search Report dated Dec. 2, 2016", 11 pgs.
"European Application Serial No. 16187862.4, Response filed Oct. 31, 2017 to Extended European Search Report dated Dec. 2, 2016", 9 pgs.
"International Application Serial No. PCT/US2008/074528, International Preliminary Report on Patentability dated Mar. 2, 2010", 13 pgs.
"International Application Serial No. PCT/US2008/074531, International Preliminary Report on Patentability dated Mar. 2, 2010", 12 pgs.
Elbashir, S. M., et al., "Functional anatomy of siRNAs for mediating efficient RNAi in *Drosophila melanogaster* embryo lysate", EMBO J. 20/23, (2001), 6877-6888.
Blow, "Small RNAs: biology's brave new world" Nature Methods (2009) vol. 6, No. 3, 231-235.
Bernstein, E., et al., "Role for a bidentate ribonuclease in the initiation step of RNA interference" Nature (2001) 409:363-366.
Bramsen et al., "Improved silencing properties using small internal segmented interfering RNAs" Nucleic Acids Research (2007), vol. 35, No. 17, p. 5886-5897.
Chang et al., "Asymmetric shorter-duplex siRNA structures trigger efficient gene silencing with reduced nonspecific effects" Molecular Therapy 17(4): 725-732 (2009).
Chiu, Y.L., and Rana, T.M., siRNA function in RNAi: a chemical modification analysis RNA (2003) 9(9):1034-48.
Clevers, H., "Wnt/beta-catenin signaling in development and disease" (2003) Cell 127:469-480.
Czauderna, F., et al., "Structural variations and stabilizing modifications of synthetic siRNAs in mammalian cells" (2003) 31 (11): 2705-2716.
Czech, M.P. "MicroRNAs as therapeutic targets" The New England Journal of Medicine (2006) 354:1194-1195.
De Fougerolles, et al., "Interfering with disease: a progress report on siRNA-based therapeutics" Nat Rev Drug Discov. (2007) 6(6):443-53.
Dignam, J.D., et al., "Accurate transcription initiation by RNA polymerase II in a soluble extract from isolate mammalian nuclei" (1983) 11; 11(5): 1475-1489.

(56) References Cited

OTHER PUBLICATIONS

Donze, O. and Picard, D., "RNA interference in mammalian cells using siRNAs synthesized with T7 RNA polymerase" (2002) Nucleic Acids Res. 30(10):e46.
Dykxhoorn, D.M., et al. "Killing the messenger: short RNAs that silence gene expression" Nat Rev Mol Cell Biol. (2003) 4(6): 457-67.
Elbashir, S.M, et al., "Duplexes of 21-nucleotide RNAs mediate RNA interference in cultured mammalian cells" Nature (2001) 411:494-498.
Elbashir, S.M., et al., "RNA interference is mediated by 21- and 22-nucleotide RNAs" Gene Dev., (2001) 15:188-200.
Elbashir, S.M., et al., "Functional anatomy of siRNAs for mediating efficient RNAi in *Drosophila melanogaster* embryo lysate" EMBO J. (2001) 20:6877-6888.
Eulalio, A., et al., "Getting to the root of miRNA-mediated gene silencing" Cell (2008) 132: 9-14.
Fire, A., et al., "Potent and Specific genetic interference by double-stranded RNA in Caenorhabditis elegans" Nature (1998) 391:806-811.
Grimm, "Asymmetry in siRNA design" Gene Therapy (2009) vol. 16, pp. 827-829.
Grimm, "Small silencing RNAs: State-of-the-art" Advanced Drug Delivery Reviews (2009) vol. 61, pp. 672-703.
Hammond, S.M., et al., "An RNA-directed nuclease mediates post-transcriptional gene silencing in *Drosophila* cells" (2000) Nature, 404: 293-296.
Hammond, S.M., et al., "Argonaute2, a link between genetic and biochemical analyses of RNAi" Science (2001) 291:1146-1150.
International Searching Authority, International Search Report and Written Opinion in PCT No. PCT/US2008/74531, dated Jan. 16, 2009.
International Searching Authority, International Search Report and Written Opinion in PCT No. PCT/US2008/74528, dated May 4, 2009.
Iorns, E., et al. "Utilizing RNA interference to enhance cancer drug discovery" Nature Reviews (2007) 6:556-568.
Kim, D. H., et al., "Synthetic dsRNA Dicer substrates enhance RNAi potency and efficacy" Nat Biotechnology (2005) 123:222-226.
Kim, D.H., and Rossi, U., "Strategies for silencing human disease using RNA interference" Nature Reviews (2007) 8:173-184.
Kleinman et al., "Sequence- and target-independent angiogenesis suppression by siRNA via TLR3" Nature (2008) vol. 452, pp. 591-598.
Let-7a sequence [retrieved from the internet on Dec. 20, 2010] <http://www.mirbase.org/cgi-bin/mirnaentry.pl?acc=MI0000060>.
Leuschner et al., "Cleavage of the siRNA passenger strand during RISC assembly in human cells" EMBO Rep. (2006) vol. 7, No. 3 p. 314-320.
Liu et al., "Structural Basis of Toll-Like Receptor 3 Signaling with Double-Stranded RNA" Science (2008), vol. 320, pp. 379-381.
Liu, J., et al., "Argonaute2 is the catalytic engine of mammalian RNAi" Science (2004) 305:1437-1441.
Lu et al., "Delivering Small Interfering RNA for Novel Therapeutics" Methods Mol. Biol. (2008) 437 p. 93-107.
Mack, G.S. "MicroRNA gets down to business" Nature Biotechnology (2007) 25:631-638.
Martinez J and Tuschl, T., "RISC is a 5' phosphomonoester-producing RNA endonuclease" Genes Dev. (2004) 18:975-980.
Matranga, C., et al. "Passenger-strand cleavage facilities assembly of siRNA into Ago2-containing RNAi enzyme complexes" Cell (2005)123:607-620.
Minakuchi et al. "Atelcollagen-Mediated Synthetic Small Interfering RNA Delivery for Effective Gene Silencing in vitro and in vivo" Nucleic Adds Res. (2004) 32 (13): e109.
Morissey et al., "Potent and Persistent in vivo Anti-HBV Activity of Chemically Modified siRNAs" Nat. Biotechnol. (2005) 23, 1002-1007.
Paddison, P.J., et al., "Short hairpin RNAs (shRNAs) induce sequence-specific silencing in mammalian cells" Genes Dev. (2002)16:948-958.
Patzel, V., "In silica selection of active siRNA" Drug Discovery Today (2007) 12:139-148.
Rana, T M "Illuminating the silence: understanding the structure and function of small RNAs" Nat. Rev. Mol. Cell Biol., (2007) 8:23-36.
Rogoff, H.A. et al., "Apoptosis associated with deregulated E2F activity is dependent on E2FI and Atm/Nbsl/Chk2" Mol Cell Biol. (2004) 24: 2968-2977.
Schmidt, "Negotiating the RNAi Patent Thicket" Nat. Biotechnol. (2007) 25, 273-275.
Schwarz, D.S., et al., "Asymmetry in the assembly of the RNAi enzyme complex".
Sibley et al., "Novel RNA-based Strategies for Therapeutic Gene Silencing" The American Society of Gene & Cell Therapy (2010) vol. 18, No. 3, 466-476.
Siolas, D., et al., "Synthetic shRNAs as potent RNAi trigger" Nat. Biotechnology (2005) 123:227-231.
Sledz, C.A., et al. "Activation of the interferon system by short-interfering RNAs" Nat. Cell Biol. (2003) 5:834-839.
Song et al. "Antibody Mediated in vivo Delivery of Small interfering RNAs via Cell-Surface Receptors" Nat. Biotechnol. (2005) 23(6) 709-717.
Soutschek, J., et al. "Therapeutic silencing of an endogenous gene by systemic administration of modified siRNAs" Nature (2004) 432: 173-178.
Sun et al., "Asymmetric RNA duplexes mediate RNA interference in mammalian cells" Nature Biotechnology (2008) vol. 26, No. 12, 1379-1382.
Tabara, H., et al., "The rde-I gene, RNA interference, and transposon silencing in C. elegans" Cell (1999) 99:123-132.
Let-7a sequence [retrieved from the internet on Dec. 20, 2010]. http://www.mirbase.org/cgi-bin/mirna_entry.pl?acc=MIOOO0060.
Bernstein E., et al., (2001), Role for a bidentate ribonuclease in the initiation step of RNA interference, Nature, 409: 363-366.
Blow, "Small RNAs: biology's brave new world," Nature Methods, Mar. 2009, vol. 6, No. 3, pp. 231-235.
Bramsen et al., "Improved silencing properties using small internally segmented interfering RNAs," Nucleic Acids Research, 2007, pp. 5886-5897, vol. 35, No. 17, Published online Jul. 28, 2007.
Chang, Chan Il et al., "Asymmetric shorter-duplex siRNA structures trigger efficient gene silencing with reduced nonspecific effects," Molecular Therapy, 17(4): 725-732 (2009).
Chiu, YL., and Rana, T.M. (2003), siRNA function in RNAi: a chemical modification analysis, RNA (New York, NY 9, 1034-1048.
Clevers, H., (2006), Wnt/beta-catenin signaling in development and disease, Cell, 127:469-480.
Czauderna, F., et al., (2003), Structural variations and stabilizing modifications of synthetic siRNAs in mammalian cells, Nucleic acids research, 31:2705-2716.
Czech M.P., (2006), MicroRNAs as therapeutic targets, The New England Journal of medicine, 354:1194-1195.
De Fougerolles et al., (2007), Interfering with disease: a progress report on siRNA-based therapeutics, Nat Rev Drug Discov, 6:443-453.
Dignam, J.D., et al., (1983), Accurate transcription initiation by RNA polymerase II in a soluble extract from isolated mammalian nuclei, Nucleic acids research, 11:1475-1489.
Donze, O.., and Picard D.., (2002), RNA interference in mammalian cells using siRNAs synthesized with T7 RNA polymerase, Nucleic Acids Res., 30:e46.
Dykxhoorn, D.M., et al., (2003), Killing the messenger: short RNAs that silence gene expression, Nat Rev Mol Cell Biol. 4:457-467.
Elbashir, S.M. et al., (2001a), Duplexes of 21-nucleotide RNAs mediate RNA interference in cultured mammalian cells, Nature 411:494-498.
Elbashir, S.M. et al., (2001b), RNA interference is mediated by 21- and 22-nucleotide RNAs, Genes Dev., 15: 188-200.
Elbashir, S.M. et al., (2001c), Functional anatomy of siRNAs for mediating efficient RNAi in *Drosophila melanogaster* embryo lysate, Embo J., 20:6877-6888.

(56) References Cited

OTHER PUBLICATIONS

Eulalio A., et al., (2008), Getting to the root of miRNA-mediated gene silencing, Cell, 132:9-14.
Fire, A., et al., (1998), Potent and specific genetic interference by double-stranded RNA in Caenorhabditis elegans, Nature, 391:806-811.
Hammond, S.M., (2001), Argonaute2, a link between genetic and biochemical analyses of RNAi, Science, 293:1146-1150.
Hammond, S.M., et al., (2000), An RNA-directed nuclease mediates post-transcriptional gene silencing in *Drosophila* cells, Nature, 404:293-296.
Iorns, E., et al., (2007), Utilizing RNA interference to enhance cancer drug discovery, Nature reviews, 6:556-568.
Kim, D.H., and Rossi, IJ., (2007), Strategies for silencing human disease using RNA interference, Nature reviews, 8:173-184.
Kim, D.H., et al., (2005), Synthetic dsRNA Dicer substrates enhance RNAi potency and efficacy, Nat Biotechno., 123:222-226.
Kleinman et al., Sequence- and target-independent angiogenesis suppression by siRNA via TLR3, Nature, Apr. 3, 2008, vol. 452, pp. 591-598.
Leuschner et al., "Cleavage of the siRNA passenger strand during RISC assembly in human cells," EMBO rep., Mar. 2006, 314-320, vol. 7. No. 3.
Liu et al, "Structural Basis of Toll-Like Receptor 3 Signaling with Double-Stranded RNA," Science, Apr. 18, 2008, vol. 320, pp. 379-381.
Liu, J., et al., (2004), Agronaute2 is the catalytic engine of mammalian RNAi, Science, 305:1437-1441.
Lu et al., "Delivering Small Interfering RNA for Novel Therapeutics," Methods Mol. Biol. 437(2008): 93-107.
Mack, G.S. (2007), MicroRNA gets down to business, Nature biotechnology, 25:631-638.
Martinez J. and Tuschl, T. (2004) RISC is a 5' phosphomonoester-producing RNA endonuclease, Genes Div., 18:975-980.
Matranga, C., et al., (2005), Passenger-strand cleavage facilitates assembly of siRNA into Ago02-containing RNAi enzyme complexes. Cell 123, 607-620.
Minakuchi et al., "Atelocollagen-Mediated Synthetic Small Interfering RNA Delivery for Effective Gene Silencing in vitro and in vivo." Nucleic Acids Res. 32.13 (2004):e109.
Morrissey et al. "Potent and Persistant in vivo Anti-HBV Activity of Chemically Modified siRNAs." Nat. Biotechnol. 23.8(2005):709-717.
Paddison, P.J., et al., (2002), Short hairpin RNAs (shRNAs) induce sequence-specific silencing in mammalian cells, Genes Dev., 16:948-958.
Patzel, V., (2007), In silica selection of active siRNA, Drug discovery today, 12:139-148.
Rana, T.M. (2007), Illuminating the silence: understanding the structure and function of small RNAs, Nat Rev Mol Cell Biol., 8:23-36.
Rofoff, H.A. et al., (2004) Apoptosis associated with deregulated E2F activity is dependent on E2FI and Atm/Nbsl/Chk2., Mol Cell Biol. 24:2968-2977.
Schmidt. "Negotiating the RNAi Patent Thicket." Nat. Biotechnol. 25.3(2007): 273-275.
Schwarz, D.S., et al., Asymmetry in the assembly of the RNAi enzyme complex, Cell, 115: 199-208 (2003).
Sibley et al., "Novel RNA-based Strategies for Therapeutic Gene Silencing," The American Society of Gene & Cell Therapy, Mar. 2010, vol. 18, No. 3, pp. 466-476.
Siolas, D., et al., (2005), Synthetic shRNAs as potent RNAi triggers, Nat Biotechno., 123:227-231.
Sledz, C.A. et al., (2003), Activation of the interferon system by short-interfering RNAs, Nat Cell Biol., 5:834-839.
Song et al., "Antibody Mediated in vivo Delivery of Small Interfering RNAs via Cell-Surface Receptors." Nat. Biotechnol. 23.6 (2005): 709-717.
Soutscheck, J., et al., (2004), Therapeutic silencing of an endogenous gene by systemic administration of modified siRNAs, Nature, 432:173-178.
Sun et al., "Asymmetric RNA duplexes mediate Rna interference in mammalian cells," Nature Biotechnology, Dec. 2008, vol. 26, No. 12, pp. 1,379-1,382.
Tabara, H., et al., (1999), The rde-I gene, RNA interference, and transposon silencing in C. elegans, Cell, 99:123-132.
Takei et al., "A small interfering RNA Targeting Vascular Endothelial Growth Factor as Cancer Therapeutics." Cancer Res. 64.10(2004): 3365-3370.
Woodle et al., "Nanoparticles Deliver RNAi Therapy." Materials Today. 8.S8(2005):34-41.
Woodle et al., "Sterically Stabilized Polypex: Ligand-Mediated Activity." J. Control. Release. 74. 1-3(2001): 309-311.
Xiang, S., et al., (2006), Short hairpin RNA-expressing bacteria elicit RNA interference in mammals, Nature, biotechnology, 24:697-702.
Xiangao, Sun, et al., "Asymmetric RNA duplexes mediate RNA interference in mammalian cells," Nature Biotech., 26 (12): 1379-1382 (2008).
Zamore, P.D. and Aronin, N., (2003), siRNAs knock down hepatitis, Nature Medicine, 9:266267.
Zamore, P.D. et al., (2000), RNAi: double-stranded RNA directs the ATP-dependent cleavage of mRNA at 21 to 23 nucleotide intervals, Cell, 101:25-33.
Zhang, B., and Farwell, M.A. (2008), microRNAs: a new emerging class for disease diagnostics and gene therapy, J Cell Mol Med., 12(2):3-21.
Zhang, H.Y., et al., (2006), RNA interference with chemically modified siRNA Current Topics in medicinal, Chemistry, 6:893-900.
"Related Chinese Patent No. CN 101835789 B, published on Jun. 24, 2015," 126 pages in Chinese original.
English Translation of Granted Claims in related Chinese Patent No. CN 101835789 B, 2 pgs.
"Related Chinese Patent No. CN 105018492 B, published on Aug. 24, 2018," 111 pages in Chinese original.
English Translation of Granted Claims in related Chinese Patent No. CN 105018492 B, 6 pages.
"Related European Application No. 16187862.4, Communication pursuant to Article 94(3) EPC dated Feb. 9, 2018," 5 pgs.
"Related European Application No. 16187862.4, Response filed Jun. 15, 2018," 10 pgs.
"Related European Application No. 16187862.4, Communication pursuant to Article 94(3) EPC dated Aug. 9, 2018," 6 pgs.
"Related Canadian Application Serial No. 2735166, Response filed Jun. 26, 2018 to Office Action dated Dec. 27, 2017," 11 pages.
"Related Japanese Patent No. 5986596, published on Sep. 6, 2016," 76 pages in Japanese original.
English Translation of Granted Claims in related Japanese Patent No. 5986596, 4 pages.
"Related Japanese Patent No. 6236498, published on Nov. 22, 2017," 76 pages in Japanese original.
English Translation of Granted Claims in related Japanese Patent No. 6236498, 3 pages.

\* cited by examiner

COMPOSITIONS OF ASYMMETRIC INTERFERING RNA AND USES THEREOF

CROSS-REFERENCE TO RELATED APPLICATIONS

This application is a Divisional of U.S. patent application Ser. No. 12/199,797 filed Aug. 27, 2008, which claims the benefit of priority to U.S. Provisional Applications Nos. 61/038,954 filed Mar. 24, 2008, 61/029,753 filed Feb. 19, 2008, and 60/968,257 filed Aug. 27, 2007. The disclosures of the prior applications are hereby incorporated in their entirety by reference.

BACKGROUND OF THE INVENTION

Gene silencing through RNAi (RNA-interference) by use of small or short interfering RNA (siRNA) has emerged as a powerful tool for molecular biology and holds the potential to be used for therapeutic purposes (de Fougerolles et al., 2007; Kim and Rossi, 2007).

RNAi can be theoretically employed to knockdown or silence any disease gene with specificity and potency. Possible applications of RNAi for therapeutic purposes are extensive and include genetic, epigenetic, and infectious diseases, provided that a disease-causing gene is identified.

However, other than the prominent delivery issue, the development of RNAi-based drugs faces challenges of limited efficacy of siRNA, non-specific effects of siRNA such as interferon-like responses and sense-strand mediated off-target gene silencing, and the prohibitive or high cost associated with siRNA synthesis. The gene silencing efficacy by siRNA is limited to about 50% or less for majority of genes in mammalian cells. The manufacture of these molecules is expensive (much more expensive than manufacturing antisense deoxynucleotides), inefficient, and requires chemical modification. Finally, the observation that the extracellular administration of synthetic siRNAs can trigger interferon-like responses has added a significant barrier for RNAi-based research and RNAi-based therapeutic development.

RNAi can be selectively triggered by synthetic short interfering RNA (siRNAs) or genetic elements encoding short-hairpin RNAs (shRNAs) that are subsequently cleaved into siRNAs by the ribonuclease III-like enzyme, Dicer. The biochemical mechanism of gene silencing, not yet fully understood, appears to involve a multi-protein RNA-induced silencing complex (RISC). RISC binds, unwinds, and incorporates the anti-sense siRNA strand, which then recognizes and targets perfectly complementary mRNAs for cleavage thereby reducing gene expression. Potent gene silencing (1-10 days) is attributable to the catalytic properties of the RISC complex. The power of RNAi stems from the exquisite specificity that can be achieved. However, off-target RNAi effects are known to occur. Another major side effect is the activation of the interferon-like response by siRNA, which is mediated via dsRNA-dependent protein kinase (PKR) and Toll-like receptors (TLR). The capability to induce interferon-like response by siRNA is mainly determined by its length. (ibid.)

For gene silencing in mammalian cells, the current art teaches that the structure of siRNA is a symmetric double stranded RNA with a length of 19-21 nucleotides and 3' overhangs on both ends to be effective in mammalian cells and to avoid cellular innate "anti-viral" responses. (ibid.) It is now well established in the field that this "optimal" structure can still trigger interferon responses, and pose significant challenges to the development of RNAi-based research and RNAi-based therapeutics (Sledz et al., 2003).

There is a need to develop novel approaches to effective RNAi in mammalian cells through a novel design of siRNAs having better efficacy and potency, rapid onset of action, better durability, and a shorter length of the RNA duplex to avoid non-specific interferon like response and to reduce the cost of synthesis for research and pharmaceutical development of RNAi therapeutics.

The references cited herein are not admitted to be prior art to the claimed invention.

SUMMARY OF THE INVENTION

The present invention is about a surprising discovery of a novel class of small duplex RNA that can induce potent gene silencing in mammalian cells, which is termed herein asymmetrical interfering RNAs (aiRNA). The hallmark of this novel class of RNAi-inducers is the length asymmetry of the two RNA strands. Such a novel structural design is not only functionally potent in effecting gene silencing, but offers several advantages over the current state-of-art siRNAs. Among the advantages, aiRNA can have RNA duplex structure of much shorter length than the current siRNA, which should reduce the cost of synthesis and abrogate/reduce the length-dependent triggering of nonspecific interferon-like responses. In addition, the asymmetry of the aiRNA structure abrogates/reduces the sense-strand mediated off-target effects. Furthermore, aiRNA is more efficacious, potent, rapid-onset, and durable than siRNA in inducing gene silencing. AiRNA can be used in all areas that current siRNA or shRNA are being applied or contemplated to be used, including biology research, R&D research in biotechnology and pharmaceutical industry, and RNAi-based therapies.

The present invention provides a duplex RNA molecule. The duplex RNA molecule comprises a first strand with a length from 18-23 nucleotides and a second strand with a length from 12-17 nucleotides, wherein the second strand is substantially complementary to the first strand, and forms a double-stranded region with the first strand, wherein the first strand has a 3'-overhang from 1-9 nucleotides, and a 5'-overhang from 0-8 nucleotides, wherein said duplex RNA molecule is capable of effecting selective gene silencing in a eukaryotic cell. In an embodiment, the first strand comprises a sequence being substantially complementary to a target mRNA sequence. In a further embodiment, the first strand comprises a sequence being at least 70 percent complementary to a target mRNA sequence. In another embodiment, the eukaryotic cell is a mammalian cell or an avian cell.

In an embodiment, at least one nucleotide of the sequence of 5' overhang is selected from the group consisting of A, U, and dT.

In an embodiment, the GC content of the double stranded region is 20%-70%.

In an embodiment, the first strand has a length from 19-22 nucleotides.

In an embodiment, the first strand has a length of 21 nucleotides. In a further embodiment, the second strand has a length of 14-16 nucleotides.

In an embodiment, the first strand has a length of 21 nucleotides, and the second strand has a length of 15 nucleotides. In a further embodiment, the first strand has a 3'-overhang of 2-4 nucleotides. In an even further embodiment, the first strand has a 3'-overhang of 3 nucleotides.

In an embodiment, the duplex RNA molecule contains at least one modified nucleotide or its analogue. In a further embodiment, the at least one modified nucleotide or its analogue is sugar-, backbone-, and/or base-modified ribonucleotide. In an even further embodiment, the backbone-modified ribonucleotide has a modification in a phosphodiester linkage with another ribonucleotide. In an embodiment, the phosphodiester linkage is modified to include at least one of a nitrogen or sulphur heteroatom. In another embodiment, the nucleotide analogue is a backbone-modified ribonucleotide containing a phosphothioate group.

In an embodiment, the at least one modified nucleotide or its analogue is an unusual base or a modified base. In another embodiment, the at least one modified nucleotide or its analogue comprises inosine, or a tritylated base.

In a further embodiment, the nucleotide analogue is a sugar-modified ribonucleotide, wherein the 2'-OH group is replaced by a group selected from H, OR, R, halo, SH, SR, $NH_2$, NHR, $NR_2$, or CN, wherein each R is independently C1-C6 alkyl, alkenyl or alkynyl, and halo is F, Cl, Br or I.

In an embodiment, the first strand comprises at least one deoxynucleotide. In a further embodiment, the at least one deoxynucleotides are in one or more regions selected from the group consisting of 3'-overhang, 5'-overhang, and double-stranded region. In another embodiment, the second strand comprises at least one deoxynucleotide.

The present invention also provides a method of modulating gene expression in a cell or an organism comprising the steps of contacting said cell or organism with the duplex RNA molecule of the invention under conditions wherein selective gene silencing can occur, and mediating a selective gene silencing effected by the duplex RNA molecule towards a target gene or nucleic acid having a sequence portion substantially corresponding to the double-stranded RNA. In a further embodiment, said contacting step comprises the step of introducing said duplex RNA molecule into a target cell in culture or in an organism in which the selective gene silencing can occur. In an even further embodiment, the introducing step is selected from the group consisting of transfection, lipofection, electroporation, infection, injection, oral administration, inhalation, topical and regional administration. In another embodiment, the introducing step comprises using a pharmaceutically acceptable excipient, carrier, or diluent selected from the group consisting of a pharmaceutical carrier, a positive-charge carrier, a liposome, a protein carrier, a polymer, a nanoparticle, a nanoemulsion, a lipid, and a lipoid.

In an embodiment, the modulating method is used for determining the function or utility of a gene in a cell or an organism.

In an embodiment, the modulating method is used for treating or preventing a disease or an undesirable condition.

In an embodiment, the target gene is associated with a disease, a pathological condition, or an undesirable condition in a mammal. In a further embodiment, the target gene is a gene of a pathogenic microorganism. In an even further embodiment, the target gene is a viral gene. In another embodiment, the target gene is a tumor-associated gene. In yet another embodiment, the target gene is a gene associated with a disease selected from the group consisting of autoimmune disease, inflammatory diseases, degenerative diseases, infectious diseases, proliferative diseases, metabolic diseases, immune-mediated disorders, allergic diseases, dermatological diseases, malignant diseases, gastrointestinal disorders, respiratory disorders, cardiovascular disorders, renal disorders, rheumatoid disorders, neurological disorders, endocrine disorders, and aging.

The present invention provides a research reagent. The reagent comprises the duplex RNA molecule.

The present invention further provides a kit. The kit comprises a first RNA strand with a length from 18-23 nucleotides and a second RNA strand with a length from 12-17 nucleotides, wherein the second strand is substantially complementary to the first strand, and capable of forming a duplex RNA molecule with the first strand, wherein the duplex RNA molecule has a 3'-overhang from 1-9 nucleotides, and a 5'-overhang from 0-8 nucleotides, wherein said duplex RNA molecule is capable of effecting sequence-specific gene silencing in a eukaryotic cell.

The present invention also provides a method of preparing the duplex RNA molecule. The method comprises the steps of synthesizing the first strand and the second strand, and combining the synthesized strands under conditions, wherein the duplex RNA molecule is formed, which is capable of effecting sequence-specific gene silencing. In an embodiment, the method further comprises a step of introducing at least one modified nucleotide or its analogue into the duplex RNA molecule during the synthesizing step, after the synthesizing and before the combining step, or after the combining step. In another embodiment, the RNA strands are chemically synthesized, or biologically synthesized.

The present invention provides an expression vector. The vector comprises a nucleic acid or nucleic acids encoding the duplex RNA molecule operably linked to at least one expression-control sequence. In an embodiment, the vector comprises a first nucleic acid encoding the first strand operably linked to a first expression-control sequence, and a second nucleic acid encoding the second strand operably linked to a second expression-control sequence. In another embodiment, the vector is a viral, eukaryotic, or bacterial expression vector.

The present invention also provides a cell. In an embodiment, the cell comprises the vector. In another embodiment, the cell comprises the duplex RNA molecule. In a further embodiment, the cell is a mammalian, avian, or bacterial cell.

The present invention provides a duplex RNA molecule. The duplex RNA molecule comprises a first strand and a second strand, wherein the first strand is longer than the second strand, wherein the second strand is substantially complementary to the first strand, and forms a double-stranded region with the first strand, wherein said duplex RNA molecule is capable of effecting selective gene silencing in a eukaryotic cell. In an embodiment, the two ends of the duplex RNA molecule are independently selected from the group consisting of 3'-overhang from 1-10 nucleotides, 5'-overhang from 0-10 nucleotides, and blunt end. In another embodiment, the first strand is substantially complementary to a target mRNA sequence. In an alternative embodiment, the second strand is substantially complementary to a target mRNA sequence. In an embodiment, the eukaryotic cell is a mammalian cell or an avian cell. In another embodiment, the duplex RNA molecule is an isolated duplex RNA molecule.

In an embodiment, the first strand has a 3'-overhang from 1-8 nucleotides and a 5'-overhang from 1-8 nucleotides.

In another embodiment, the first strand has a 3'-overhang from 1-10 nucleotides and a blunt end.

In yet another embodiment, the first strand has a 5'-overhang from 1-10 nucleotides and a blunt end.

In an alternative embodiment, the RNA duplex has two 5'-overhangs from 1-8 nucleotides, or two 3'-overhangs from 1-10 nucleotides.

In an embodiment, the first strand has a length from 12-100 nucleotides, from 12-30 nucleotides from 18-23 nucleotides, from 19-25 nucleotides. In a further embodiment, the first strand has a length of 21 nucleotides.

In another embodiment, the second strand has a length from 5-30 nucleotides, 12-22 nucleotides, 12-17 nucleotides. In a further embodiment, the second strand has a length of 15 nucleotides.

In an embodiment, the first strand has a length from 12-30 nucleotides, and the second strand has a length from 10-29 nucleotides, with the provision that when the double stranded region is 27 bp, the both ends of the RNA molecule are independently 3' overhang or 5' overhang. In a further embodiment, the first strand has a length from 18-23 nucleotides, and the second strand has a length from 12-17 nucleotides.

In another embodiment, the first strand has a length from 19-25 nucleotides, and the second strand has a length from 12-17 nucleotides.

In an alternative embodiment, the first strand has a length from 19-25 nucleotides, and the second strand has a length from 18-24 nucleotides, with the provision that when the first strand is

```
                                            (SEQ ID NO: 1)
    5'-UUCGAAGUAUUCCGCGUACGU (SEQ ID NO: 2)
    5'-UCGAAGUAUUCCGCGUACGUG
    or
                                            (SEQ ID NO: 3)
    5'-CGAAGUAUUCCGCGUACGUGA
``` the second strand has a length of at most 17 nucleotides, or contains at least one mismatch with the first strand, or contains at least one modification.

In an embodiment, the first strand has a length of 21 nucleotides and the second strand has a length of 12-17 nucleotides, or 14-16 nucleotides.

In an embodiment, the first strand is from 1-10 nucleotides longer than the second strand.

In an embodiment, the 3'-overhang has a length from 2-6 nucleotides.

In another embodiment, the 5'-overhang has a length from 0-5 nucleotides.

In an embodiment, the gene silencing comprises one or two, or all of RNA interference, modulation of translation, and DNA epigenetic modulations.

In another embodiment, the duplex RNA molecule further comprises a nick in at least one of said first and second strands.

In another embodiment, the double stranded region comprises a gap of one or more nucleotides.

In an embodiment, at least one nucleotide of the 5' overhang is not complementary to the target mRNA sequence.

In another embodiment, at least one nucleotide of 5' overhang is selected from the group consisting of A, U, and dT.

In an embodiment, the duplex RNA molecule is conjugated to an entity selected from the group consisting of peptide, antibody, polymer, lipid, oligonucleotide, cholesterol, and aptamer.

In an embodiment, the RNA molecule further comprises at least one unmatched or mismatched nucleotide.

In another embodiment, the GC content of the double stranded region is 20-70%.

In an embodiment, the 3'-overhang and/or 5'-overhang is stabilized against degradation.

In an embodiment, the duplex RNA molecule contains at least one modified nucleotide or its analogue. In a further embodiment, the at least one modified nucleotide or its analogue is sugar-, backbone-, and/or base-modified ribonucleotide. In a further embodiment, the backbone-modified ribonucleotide has a modification in a phosphodiester linkage with another ribonucleotide. In another embodiment, the phosphodiester linkage is modified to include at least one of a nitrogen or sulphur heteroatom. In yet another embodiment, the nucleotide analogue is a backbone-modified ribonucleotide containing a phosphothioate group.

In an embodiment, the at least one modified nucleotide or its analogue comprises a non-natural base or a modified base. In another embodiment, the at least one modified nucleotide or its analogue comprises inosine, or a tritylated base.

In a further embodiment, the nucleotide analogue is a sugar-modified ribonucleotide, wherein the 2'-OH group is replaced by a group selected from H, OR, R, halo, SH, SR, $NH_2$, NHR, $NR_2$, or CN, wherein each R is independently C1-C6 alkyl, alkenyl or alkynyl, and halo is F, Cl, Br or I.

In an embodiment, the first strand comprises at least one deoxynucleotide. In a further embodiment, the at least one deoxynucleotides are in one or more regions selected from the group consisting of 3'-overhang, 5'-overhang, and double-stranded region proximal to the 5' end of the first strand. In another embodiment, the second strand comprises at least one deoxynucleotide.

The present invention also provides a method of modulating gene expression in a cell or an organism. The method comprises the steps of: contacting said cell or organism with the duplex RNA molecule of claim 1 under conditions wherein selective gene silencing can occur, and mediating a selective gene silencing effected by the double-stranded RNA towards a target nucleic acid having a sequence portion substantially corresponding to the double-stranded RNA. In a further embodiment, said contacting comprises the step of introducing said duplex RNA molecule into a target cell in culture or in an organism in which the selective gene silencing can occur. In an even further embodiment, the introducing step is selected from the group consisting of transfection, lipofection, electroporation, infection, injection, oral administration, inhalation, topical and regional administration. In another embodiment, the introducing step comprises using a pharmaceutically acceptable excipient, carrier, or diluent selected from the group consisting of a pharmaceutical carrier, a positive-charge carrier, a liposome, a protein carrier, a polymer, a nanoparticle, a nanoemulsion, a lipid, and a lipoid. In an embodiment, the modulating method is used for modulating the expression of a gene in a cell or an organism.

In another embodiment, the modulating method is used for treating or preventing a disease or an undesirable condition.

In an embodiment, the target gene is a gene associated with human or animal diseases. In a further embodiment, the gene is a gene of a pathogenic microorganism. In an even further embodiment, the target gene is a viral gene. In another embodiment, the gene is a tumor-associated gene.

In yet another embodiment, the target gene is a gene associated with a disease selected from the group consisting of autoimmune disease, inflammatory diseases, degenerative diseases, infectious diseases, proliferative diseases, metabolic diseases, immune-mediated disorders, allergic diseases, dermatological diseases, malignant diseases, gastrointestinal disorders, respiratory disorders, cardiovascular disorders, renal disorders, rheumatoid disorders, neurological disorders, endocrine disorders, and aging.

The modulating method can also be used for studying drug target in vitro or in vivo.

The present invention provides a reagent comprising the duplex RNA molecule.

The present invention further provides a kit. The kit comprises a first RNA strand and a second RNA strand, wherein the first strand is longer than the second strand, wherein the second strand is substantially complementary to the first strand, and capable of forming a duplex RNA molecule with the first strand, wherein said duplex RNA molecule is capable of effecting sequence-specific gene silencing in a eukaryotic cell.

The present invention also provides a method of preparing the duplex RNA molecule of claim 1 comprising the steps of synthesizing the first strand and the second strand, and combining the synthesized strands under conditions, wherein the duplex RNA molecule is formed, which is capable of effecting sequence-specific gene silencing. In an embodiment, the RNA strands are chemically synthesized, or biologically synthesized. In another embodiment, the first strand and the second strand are synthesized separately or simultaneously.

In an embodiment, the method further comprises a step of introducing at least one modified nucleotide or its analogue into the duplex RNA molecule during the synthesizing step, after the synthesizing and before the combining step, or after the combining step.

The present invention further provides a pharmaceutical composition. The pharmaceutical composition comprises as an active agent at least one duplex RNA molecule and one or more carriers selected from the group consisting of a pharmaceutical carrier, a positive-charge carrier, a liposome, a protein carrier, a polymer, a nanoparticle, a cholesterol, a lipid, and a lipoid.

The present invention also provides a method of treatment. The method comprises administering an effective amount of the pharmaceutical composition to a subject in need. In an embodiment, the pharmaceutical composition is administered via a route selected from the group consisting of iv, sc, inhalation, topical, po, and regional administration.

In an embodiment, the first strand comprises a sequence being substantially complimentary to the target mRNA sequence of a gene selected from the group consisting of a developmental gene, an oncogene, a tumor suppresser gene, and an enzyme gene, and a gene for an adhesion molecule, a cyclin kinase inhibitor, a Wnt family member, a Pax family member, a Winged helix family member, a Hox family member, a cytokine/lymphokine or its receptor, a growth/differentiation factor or its receptor, a neurotransmitter or its receptor, a kinase, a signal transducer, a viral gene, a gene of an infectious disease, ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES, APC, BRCA1, BRCA2, MADH4, MCC, NF1, NF2, RB1, TP53, WT1, an ACP desaturase or hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, a DNA or RNA polymerase, a galactosidase, a glucanase, a glucose oxidase, a GTPase, a helicase, a hemicellulase, an integrase, an invertase, an isomerase, a kinase, a lactase, a lipase, a lipoxygenase, a lysozyme, a pectinesterase, a peroxidase, a phosphatase, a phospholipase, a phosphorylase, a polygalacturonase, a proteinase or peptideases, a pullanase, a recombinase, a reverse transcriptase, a topoisomerase, a xylanase, k-RAS, β-Catenin, Rsk1, PCNA, p70S6K, Survivin, mTOR, PTEN, Parp1, or p21.

In another embodiment, the duplex RNA molecule is selected from the group consisting of

| | |
|---|---|
| aiNbs1 | 5'-AUGCUGUGUUAACUG<br>(SEQ ID NO: 4)<br>UAGUACGACACAAUUGACGAA-5'<br>(SEQ ID NO: 5) |
| aiEF2 | 5'-CCUCUUAUGAUGUAU<br>(SEQ ID NO: 6)<br>CCGGGAGAAUACUACAUAUAA-5'<br>(SEQ ID NO: 7) |
| aiStat3-A | 5'-AGCAAAGAAUCACAU<br>(SEQ ID NO: 8)<br>CGGUCGUUUCUUAGUGUACAA-5'<br>(SEQ ID NO: 9) |
| aiStat3-B | 5'-GAAUCUCAACUUCAG<br>(SEQ ID NO: 10)<br>CGUCUUAGAGUUGAAGUCUAA-5'<br>(SEQ ID NO: 11) |
| aiPTEN | 5'-UAAAGGUGAAGAUAU<br>(SEQ ID NO: 12)<br>UCGAUUUCCACUUCUAUAUAA-5'<br>(SEQ ID NO: 13) |
| aip70S6K | 5'-UGUUUGAUUUGGAUU<br>(SEQ ID NO: 14)<br>GGCACAAACUAAACCUAAAAA-5'<br>(SEQ ID NO: 15) |
| aimTOR | 5'-GAAUUGUCAAGGGAU<br>(SEQ ID NO: 16)<br>CGUCUUAACAGUUCCCUAUAA-5'<br>(SEQ ID NO: 17) |
| aiRskL | 5'-AAUUGGAACACAGUU<br>(SEQ ID NO: 18)<br>CCUUUAACCUUGUGUCAAAAA-5'<br>(SEQ ID NO: 19) |
| aiPCNA | 5'-AGAUGCUGUUGUAAU<br>(SEQ ID NO: 20)<br>ACCUCUACGACAACAUUAAAA-5'<br>(SEQ ID NO: 21) |
| aiParpL | 5'-GCGAAGAAGAAAUCU<br>(SEQ ID NO: 22)<br>CACCGCUUCUUCUUUAGAUAA-5'<br>(SEQ ID NO: 23) |
| aiSurvivin | 5'-AGGAGAUCAACAUUU<br>(SEQ ID NO: 24)<br>dTdTUUCCUCUAGUUGUAAAAGU-5'<br>(SEQ ID NO: 25) |
| aiNQ01 | 5'-GCAGACCUUGUGAUA<br>(SEQ ID NO: 26)<br>CGGCGUCUGGAACACUAUAAA-5'<br>(SEQ ID NO: 27) |
| aip21-A | 5'-CCCGCUCUACAUCUU<br>(SEQ ID NO: 28)<br>UCCGGGCGAGAUGUAGAAGAA-5'<br>(SEQ ID NO: 29) |
| aip21-B | 5'-GGCGGUUGAAUGAGA<br>(SEQ ID NO: 30)<br>GAUCCGCCAACUUACUCUCAA-5'<br>(SEQ ID NO: 31) |
| aik-Ras | 5'-GGAGCUGUUGGCGUA<br>(SEQ ID NO: 32)<br>CAACCUCGACAACCGCAUCAA-5'<br>(SEQ ID NO: 33) |

-continued

| | |
|---|---|
| aiβ-cantenin-1 | 5'-GCUGAUAUUGAUGGA<br>(SEQ ID NO: 34)<br>CAUCGACUAUAACUACCUGAA-5'<br>(SEQ ID NO: 39) |
| aiβ-cantenin-2 | 5'-GAUAUUGAUGGACUU<br>(SEQ ID NO: 36)<br>CAUCGACUAUAACUACCUGAA-5'<br>(SEQ ID NO: 39) |
| aiβ-cantenin-4 | 5'-CUGAUAUUGAUGGAC<br>(SEQ ID NO: 38)<br>CAUCGACUAUAACUACCUGAA-5'<br>(SEQ ID NO: 39) |
| aiβ-catenin-5 | 5'-AGCUGAUAUUGAUGG<br>(SEQ ID NO: 40)<br>CAUCGACUAUAACUACCUGAA-5'<br>(SEQ ID NO: 39) |
| aiβ-catenin-8 | 5'-UAGCUGAUAUUGAUG<br>(SEQ ID NO: 41)<br>CAUCGACUAUAACUACCUGAA-5'<br>(SEQ ID NO: 39) |
| aiβ-catenin-9 | 5'-UGAUAUUGAUGGACU<br>(SEQ ID NO: 42)<br>CAUCGACUAUAACUACCUGAA-5'<br>(SEQ ID NO: 39) |
| aiβ-catenin-10 | 5'-GCUGAUAUUGAUGGA<br>(SEQ ID NO: 34)<br>UCAUCGACUAUAACUACCUGAA-5'<br>(SEQ ID NO: 43) |
| aiβ-catenin-11 | 5'-GCUGAUAUUGAUGGA<br>(SEQ ID NO: 34)<br>CAUCGACUAUAACUACCUGAAA-5'<br>(SEQ ID NO: 35) |
| aiβ-catenin-18 | 5'-GCUGAUAUUGAUGGA<br>(SEQ ID NO: 34)<br>AUCGACUAUAACUACCUGAA-5'<br>(SEQ ID NO: 37) |
| aiβ-catenin-34 | 5'-GCUGAUAUUGAUGGAC<br>(SEQ ID NO: 44)<br>CAUCGACUAUAACUACCUGAA-5'<br>(SEQ ID NO: 39) |
| aiβ-catenin-35 | 5'-AGCUGAUAUUGAUGGA<br>(SEQ ID NO: 45)<br>CAUCGACUAUAACUACCUGAA-5'<br>(SEQ ID NO: 39) |
| aiβ-catenin-36 | 5'-AGCUGAUAUUGAUGGAC<br>(SEQ ID NO: 46)<br>CAUCGACUAUAACUACCUGAA-5'<br>(SEQ ID NO: 39) |
| aiβ-catenin-37 | 5'-AGCUGAUAUUGAUGGACU<br>(SEQ ID NO: 47)<br>CAUCGACUAUAACUACCUGAA-5'<br>(SEQ ID NO: 39) |
| aiβ-catenin-38 | 5'-UAGCUGAUAUUGAUGGAC<br>(SEQ ID NO: 48)<br>CAUCGACUAUAACUACCUGAA-5'<br>(SEQ ID NO: 39) |
| aiβ-catenin-39 | 5'-GCUGAUAUUGAUGGACUU<br>(SEQ ID NO: 49)<br>CAUCGACUAUAACUACCUGAA-5'<br>(SEQ ID NO: 39) |
| aiβ-catenin-40 | 5'-AGCUGAUAUUGAUGGACUU<br>(SEQ ID NO: 50)<br>CAUCGACUAUAACUACCUGAA-5'<br>(SEQ ID NO: 39) |
| aiβ-catenin-42 | 5'-UAGCUGAUAUUGAUGGACU<br>(SEQ ID NO: 51)<br>CAUCGACUAUAACUACCUGAA-5'<br>(SEQ ID NO: 39) |
| aiβ-catenin-43 | 5'-UAGCUGAUAUUGAUGGACUU<br>(SEQ ID NO: 52)<br>CAUCGACUAUAACUACCUGAA-5'<br>(SEQ ID NO: 39) |
| aiβ-catenin-44 | 5'-GUAGCUGAUAUUGAUGGACU<br>(SEQ ID NO: 53)<br>CAUCGACUAUAACUACCUGAA-5'<br>(SEQ ID NO: 39) |
| aiβ-catenin-45 | 5'-GCUGAUAUUGAAGGA<br>(SEQ ID NO: 54)<br>CAUCGACUAUAACUACCUGAA-5'<br>(SEQ ID NO: 39) |
| aiβ-catenin-46 | 5'-GCUGAUAUUGAUGGA<br>(SEQ ID NO: 34)<br>CAUCGACUAUAACUACCUGUC-5'<br>(SEQ ID NO: 55) |
| aiβ-catenin-47 | 5'-GCUGAUAUUGAUGGA<br>(SEQ ID NO: 34)<br>CAUCGACUAUAACUACCUgaa-5'<br>(SEQ ID NO: 56) |
| aiβ-catenin-48 | 5'-GCUGAUAUUGAUGGA<br>(SEQ ID NO: 34)<br>CGACUAUAACUACCUGAA-5'<br>(SEQ ID NO: 57) |
| | 5-gCUGAUAUUGAUGGA<br>(SEQ ID NO: 58)<br>CAUCGACUAUAACUACCUGAA-5'<br>(SEQ ID NO: 39) |
| aiβ-catenin 53 | 5'-GCUGAUAUUGAUGGa<br>(SEQ ID NO: 59)<br>CAUCGACUAUAACUACCUGAA-5'<br>(SEQ ID NO: 39) |
| aiβ-catenin-57 | 5'-gCUGAUAUUGAUGGA<br>(SEQ ID NO: 58)<br>catCGACUAUAACUACCUGAA-5'<br>(SEQ ID NO: 39) |
| aiβ-catenin-59 | 5'-GCUGAUAUUGAUGGa<br>(SEQ ID NO: 59)<br>catCGACUAUAACUACCUGAA-5' and<br>(SEQ ID NO: 57) |
| aiβ-catenin-62 | 5'-UAGCUGAUAUUGAUGGACU<br>(SEQ ID NO: 51)<br>CAUCGACUAUAACUACCUgaa-5'<br>(SEQ ID NO: 56) |

Wherein A, U, G, and C are nucleotides, while a, t, g, and c are deoxynucleotides.

The present invention provides a method of modifying a first duplex RNA molecule with an antisense strand and a sense strand that form a double-stranded region. The method comprises, shortening the length of the sense strand so that the antisense strand has a 3'-overhang from 1-8 nucleotides and a 5'-overhang from 0-8 nucleotides, and forming a second duplex RNA molecule; wherein at least one property of the first duplex RNA molecule is improved. In an embodiment, the property is selected from the group consisting of size, efficacy, potency, the speed of onset, durability, synthesis cost, off-target effects, interferon response, and delivery. In another embodiment, the method further comprises combining the antisense strand and the shortened sense strand under conditions, wherein the second duplex RNA molecule is formed. In a further embodiment, the first duplex RNA molecule is a siRNA, or dicer-substrate siRNA, or a siRNA precursor.

The present invention provides an expression vector. The vector comprises a nucleic acid or nucleic acids encoding the duplex RNA molecule of claim 1 operably linked to at least one expression-control sequence. In an embodiment, the expression vector comprises a first nucleic acid encoding the first strand operably linked to a first expression-control sequence, and a second nucleic acid encoding the second strand operably linked to a second expression-control sequence. In another embodiment, the expression vector is a viral, eukaryotic expression vector, or bacterial expression vector.

The present invention also provides a cell. In an embodiment, the cell comprises the expression, vector. In another embodiment, the cell comprises the duplex RNA molecule. In yet another embodiment, the cell is a mammalian cell, avian cell, or bacterial cell.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

Cells were transfected with aiRNA or aiRNA with sense strand 2'-O-methyl at position 8 (predicted Ago2 cleavage site) or position 9 as a control. RNA was collected at 4 hours post transfection and qRT-PCR performed to determine relative levels of β-catenin mRNA remaining.

Figure 9A:

FIG. 9 shows the aiRNA and siRNA competition analysis. (A) illustrates the siRNA and aiRNA duplex containing $^{32}$P end labeled antisense strands. The (*) marks the location of the label. (B) shows that the cold aiRNA does not compete with labeled siRNA for Ago2. Hela S-10 lysate containing overexpressed Ago2 was incubated with the $^{32}$P end labeled siRNA and cold aiRNA or siRNA duplex prior to Ago2 immunoprecipitation. RNA was then isolated and analyzed on 15% acrylamide gel. (C) shows that the cold siRNA does not compete with labeled aiRNA for Ago2. The same S-10 lysate used in B was incubated with the $^{32}$P end labeled aiRNA and cold aiRNA or siRNA duplex prior to Ago2 immunoprecipitation. RNA was then isolated and analyzed on 15% acrylamide gel.

Figure 10:
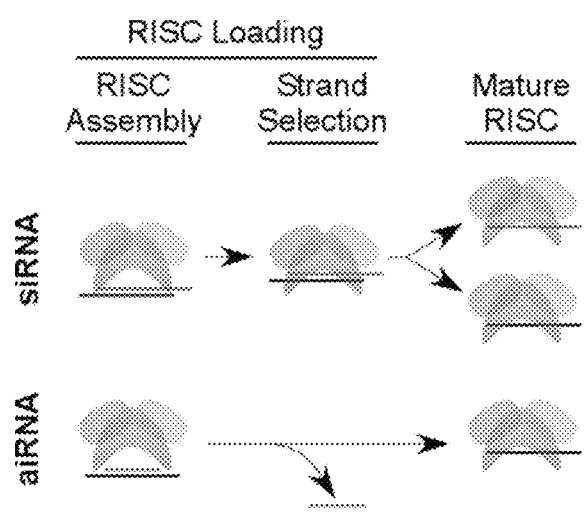

FIG. 10 illustrates the model of aiRNA and siRNA showing observed differences in RISC loading and generation of mature RISC.

FIG. 11 shows asymmetric RNA duplexes of 14-15 bp with antisense overhangs (aiRNA) induced potent, efficacious, rapid, and durable gene silencing. (A) shows the Diagram showing sequence and design of siRNA (SEQ ID NOs:71 and 107) and aiRNA targeting β-catenin (Table 3). (B) shows the induction of gene silencing by aiRNA of various lengths. β-catenin protein levels were analysed by western blot in cells transfected with indicated aiRNA for 48 hours. (C) shows that aiRNA is more potent and efficacious than siRNA in inducing β-catenin protein depletion. Hela cells were transfected with aiRNA or siRNA targeting β-catenin at the indicated concentrations. At 48 hours post-transfection, cell lysates were made and western blot analysis was done. (D) shows that the aiRNA is more efficacious, rapid, and durable than siRNA in reducing β-catenin RNA levels. Cells were transfected with 10 nM 15 bp aiRNA or 21-mer siRNA for the indicated number of days before northern blot analysis.

FIG. 12 shows that aiRNA mediates rapid and potent silencing. (A) shows the sequence and structure of aiRNA (SEQ ID NOs:34 and 39) and siRNA used to target β-catenin (SEQ ID NOs:71 and 107). (B) shows RT-PCR of β-catenin mRNA levels from cells transfected with control aiRNA or aiRNA targeting β-catenin. RNA was collected at the indicated times post transfection. (C) shows the quantitative real-time RT-PCR of β-catenin mRNA levels in cells transfected with control, aiRNA, or siRNA for the indicated number of hours. (D) shows the western blot analysis of β-catenin protein levels in cells transfected with control, aiRNA, or siRNA for the indicated times.

Figure 13:
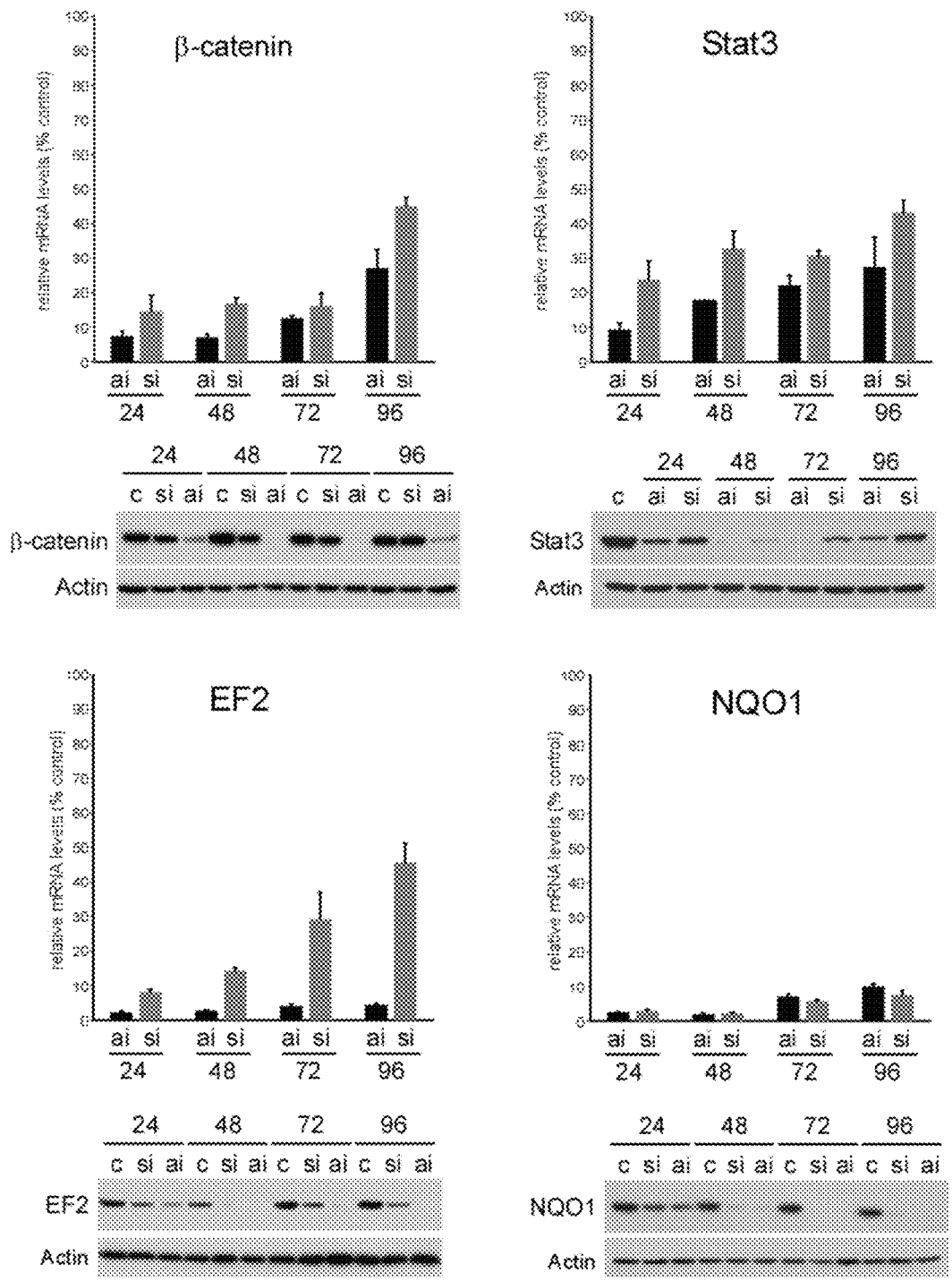

FIG. 13 shows the comparison of aiRNA with siRNA in gene silencing efficacy and durability against multiple targets. Hela cells were transfected with scramble siRNA (c), aiRNA (ai), or siRNA (si) targeting (a) β-catenin at 10 nM, (b) Stat3, (c) EF2, or (d) NQO1 at 20 nM. RNA and protein was purified at the indicated time points and analyzed for mRNA levels by quantitative real time polymerase chain reaction (qRT-PCR) and protein levels by western blot. qRT-PCR data is normalized to siCon transfected cells.

FIG. 14 shows aiRNA mediated gene silencing is effective against various genes in multiple cell lines. (A) shows aiRNA duplex is more efficacious than siRNA in targeting β-catenin in different mammalian cell lines. (B) shows the western blot analysis of Nbs1, Survivin, Parp1, p21 from cells transfected with 20 nM of the indicated aiRNA or siRNA for 48 hours. (C) shows the western blot analysis of Rsk1, PCNA, p70S6K, mTOR, and PTEN from cells transfected with 20 nM of the indicated aiRNA or siRNA for 48 hours. (D) shows the allele-specific gene silencing of k-Ras by aiRNA. aiRNA targeting wildtype k-Ras was tested for silencing of k-Ras in both k-Ras wildtype (DLD1) and k-Ras mutant (SW480) cell lines by western blot analysis.

FIG. 15 show the lack of off-target gene silencing by sense-strand, immunostimulation, and serum stability of aiRNAs. (A) shows RT-PCR analysis of the expression of interferon inducible genes in PBMC mock treated or incubated with β-catenin siRNA or aiRNA duplex for 16 hours. (B) shows RT-PCR analysis of the expression of interferon inducible genes in Hela cells mock transfected or transfected with EF2 or Survivin aiRNA or siRNA for 24 hours. (C) shows the microarray analysis for changes in the expression of known interferon response related genes. Total RNA isolated from aiRNA and siRNA transfected Hela cells was analyzed by microarray. (D) shows that no sense-strand mediated off-target gene silencing is detected for aiRNA. Cells were co-transfected with aiRNA or siRNA and either a plasmid expressing Stat3 (sense RNA) or a plasmid expressing antisense Stat3 (antisense RNA). Cells were harvested and RNA collected at 24 hours post transfection and relative levels of Stat3 sense or antisense RNA were determined by quantitative real time PCR or RT-PCR (inserts). (E) shows the Stability of aiRNA and siRNA duplexes in human serum. aiRNA and siRNA duplexes were incubated in 10% human serum at 37° C. for the indicated amount of time prior to gel electrophoresis. Duplex remaining (% of control) is indicated. (F) illustrates the proposed model for gene specific silencing mediated by the aiRNA duplex.

Figure 16:
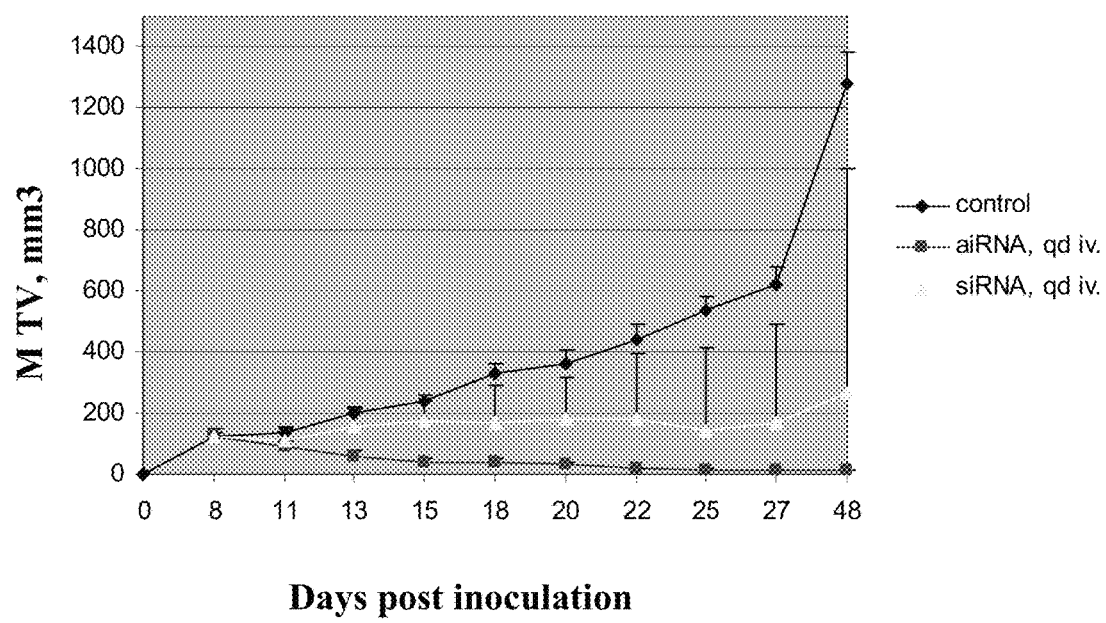

FIG. 16 shows the potent Anti-Tumor Activity of aiRNA against β-catenin in SW480 human colon xenografted mouse model. Immunosuppressed mice with established subcutaneous SW480 human colon cancer were given intravenously (iv) with 0.6 nmol PEI-complexed β-catenin siRNAs, PEI-complexed β-catenin aiRNAs or a PEI-complexed unrelated siRNA as negative control daily. Tumor size was evaluated periodically during treatment. Each point represents the mean±SEM of six tumors.

Figure 17:
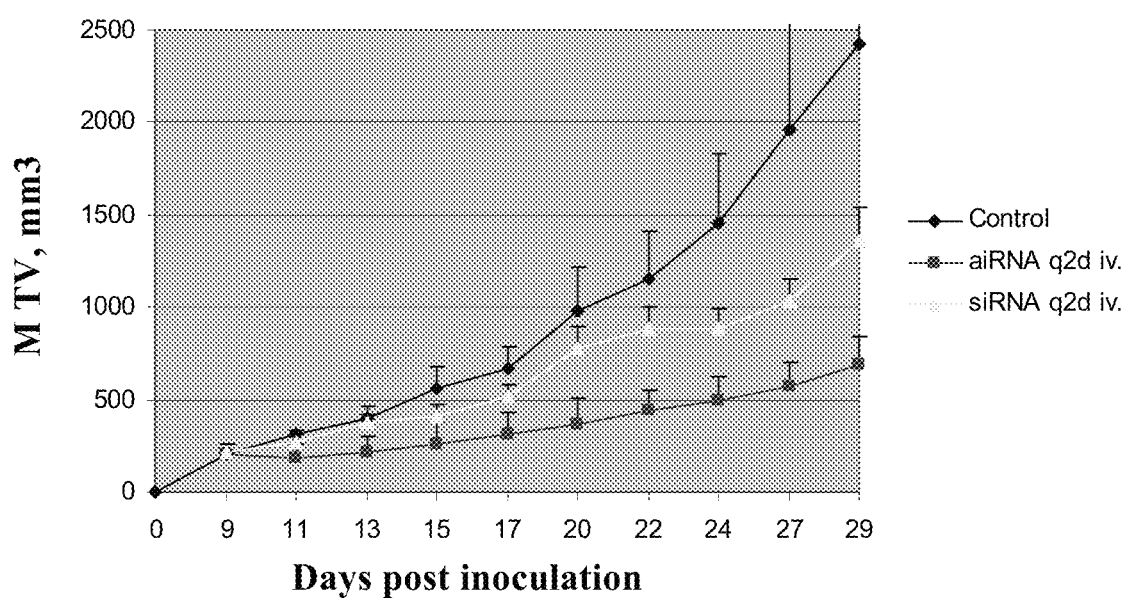

FIG. 17 shows the potent Anti-Tumor Activity of aiRNA against β-catenin in HT29 human colon xenografted mouse model. Immunosuppressed mice with established subcutaneous HT29 human colon cancer were given intravenously (iv) with 0.6 nmol PEI-complexed β-catenin siRNAs, PEI-complexed β-catenin aiRNAs or a PEI-complexed unrelated siRNA as negative control every other day. Tumor size was evaluated periodically during treatment. Each point represents the mean±SEM of five tumors.

DETAILED DESCRIPTION OF THE INVENTION

The present invention relates to an asymmetric duplex RNA molecule that is capable of effecting selective gene silencing in a eukaryotic cell. In an embodiment, the duplex RNA molecule comprises a first strand and a second strand. The first strand is longer than the second strand. The second strand is substantially complementary to the first strand, and forms a double-stranded region with the first strand.

In an embodiment, the duplex RNA molecule has a 3'-overhang from 1-8 nucleotides and a 5'-overhang from 1-8 nucleotides, a 3'-overhang from 1-10 nucleotides and a blunt end, or a 5'-overhang from 1-10 nucleotides and a blunt end. In another embodiment, the duplex RNA molecule has two 5'-overhangs from 1-8 nucleotides or two 3'-overhangs from 1-10 nucleotides. In a further embodiment, the first strand has a 3'-overhang from 1-8 nucleotides and a 5'-overhang from 1-8 nucleotides. In an even further embodiment, the duplex RNA molecule is an isolated duplex RNA molecule.

In an embodiment, the first strand has a 3'-overhang from 1-10 nucleotides, and a 5'-overhang from 1-10 nucleotides or a 5'-blunt end. In another embodiment, the first strand has a 3'-overhang from 1-10 nucleotides, and a 5'-overhang from 1-10 nucleotides. In an alternative embodiment, the first strand has a 3'-overhang from 1-10 nucleotides, and a 5'-blunt end.

In an embodiment, the first strand has a length from 5-100 nucleotides, from 12-30 nucleotides, from 15-28 nucleotides, from 18-27 nucleotides, from 19-23 nucleotides from 20-22 nucleotides, or 21 nucleotides.

In another embodiment, the second strand has a length from 3-30 nucleotides, from 12-26 nucleotides, from 13-20 nucleotides, from 14-23 nucleotides, 14 or 15 nucleotides.

In an embodiment, the first strand has a length from 5-100 nucleotides, and the second strand has a length from 3-30 nucleotides; or the first strand has a length from 10-30 nucleotides, and the second strand has a length from 3-29 nucleotides; or the first strand has a length from 12-30 nucleotides and the second strand has a length from 10-26 nucleotides; or the first strand has a length from 15-28 nucleotides and the second strand has a length from 12-26 nucleotides; or the first strand has a length from 19-27 nucleotides and the second strand has a length from 14-23 nucleotides; or the first strand has a length from 20-22 nucleotides and the second strand has a length from 14-15 nucleotides. In a further embodiment, the first strand has a length of 21 nucleotides and the second strand has a length of 13-20 nucleotides, 14-19 nucleotides, 14-17 nucleotides, 14 or 15 nucleotides.

In an embodiment, the first strand is at least 1, 2, 3, 4, 5, 6, 7, 8, 9, or 10 nucleotides longer than the second strand.

In an embodiment, the duplex RNA molecule further comprises 1-10 unmatched or mismatched nucleotides. In a further embodiment, the unmatched or mismatched nucleotides are at or near the 3' recessed end. In an alternative embodiment, the unmatched or mismatched nucleotides are at or near the 5' recessed end. In an alternative embodiment, the unmatched or mismatched nucleotides are at the double-stranded region. In another embodiment, the unmatched or mismatched nucleotide sequence has a length from 1-5 nucleotides. In an even further embodiment, the unmatched or mismatched nucleotides form a loop structure.

In an embodiment, the first strand or the second strand contains at least one nick, or formed by two nucleotide fragments.

In an embodiment, the gene silencing is achieved through one or two, or all of RNA interference, modulation of translation, and DNA epigenetic modulations.

As used in the specification and claims, the singular form "a", "an", and "the" include plural references unless the context clearly dictate otherwise. For example, the term "a cell" includes a plurality of cells including mixtures thereof.

As used herein, a "double stranded RNA," a "duplex RNA" or a "RNA duplex" refers to an RNA of two strands and with at least one double-stranded region, and includes RNA molecules that have at least one gap, nick, bulge, and/or bubble either within a double-stranded region or between two neighboring double-stranded regions. If one strand has a gap or a single-stranded region of unmatched nucleotides between two double-stranded regions, that strand is considered as having multiple fragments. A double-stranded RNA as used here can have terminal overhangs on either end or both ends. In some embodiments, the two strands of the duplex RNA can be linked through certain chemical linker.

As used herein, an "antisense strand" refers to an RNA strand that has substantial sequence complementarity against a target messenger RNA. An antisense strand can be part of an siRNA molecule, part of a miRNA/miRNA* duplex, or a single-strand mature miRNA.

The term "isolated" or "purified" as used herein refers to a material that is substantially or essentially free from components that normally accompany it in its native state. Purity and homogeneity are typically determined using analytical chemistry techniques such as polyacrylamide gel electrophoresis or high performance liquid chromatography.

As used herein, "modulating" and its grammatical equivalents refer to either increasing or decreasing (e.g., silencing), in other words, either up-regulating or down-regulating. As used herein, "gene silencing" refers to reduction of gene expression, and may refer to a reduction of gene expression about 20%, 30%, 40%, 50%, 60%, 70%, 80%, 90% or 95% of the targeted gene.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Terms such as "treating" or "treatment" or "to treat" or "alleviating" or "to alleviate" as used herein refer to both (1) therapeutic measures that cure, slow down, lessen symptoms of, and/or halt progression of a diagnosed pathologic condition or disorder and (2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life.

As used herein, the terms "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refer to a reduction of about 20%, 30%, 40%, 50%, 60%, 70%, 80%, 90% or 95% of the targeted activity. When used in the context of a disorder or disease, the terms refer to success at preventing the onset of symptoms, alleviating symptoms, or eliminating the disease, condition or disorder.

As used herein, the term "substantially complementary" refers to complementarity in a base-paired, double-stranded region between two nucleic acids and not any single-stranded region such as a terminal overhang or a gap region between two double-stranded regions. The complementarity does not need to be perfect; there may be any number of base pair mismatches, for example, between the two nucleic acids. However, if the number of mismatches is so great that no hybridization can occur under even the least stringent hybridization conditions, the sequence is not a substantially complementary sequence. When two sequences are referred to as "substantially complementary" herein, it means that the sequences are sufficiently complementary to each other to hybridize under the selected reaction conditions. The relationship of nucleic acid complementarity and stringency of hybridization sufficient to achieve specificity is well known in the art. Two substantially complementary strands can be, for example, perfectly complementary or can contain from 1 to many mismatches so long as the hybridization conditions are sufficient to allow, for example discrimination between a pairing sequence and a non-pairing sequence. Accordingly, substantially complementary sequences can refer to sequences with base-pair complementarity of 100, 95, 90, 80, 75, 70, 60, 50 percent or less, or any number in between, in a double-stranded region.

As used herein, antagomirs are miRNA inhibitors, and can be used in silencing endogenous miRNAs. As used herein, mimetics or mimics are miRNA agonists, and can be used to replace endogenous miRNAs as functional equivalents and thereby upregulating pathways affected by such endogenous miRNAs.

1. RNA Interference

RNA interference (abbreviated as RNAi) is a cellular process for the targeted destruction of single-stranded RNA (ssRNA) induced by double-stranded RNA (dsRNA). The ssRNA is gene transcript such as a messenger RNA (mRNA). RNAi is a form of post-transcriptional gene silencing in which the dsRNA can specifically interfere with the expression of genes with sequences that are complementary to the dsRNA. The antisense RNA strand of the dsRNA targets a complementary gene transcript such as a messenger RNA (mRNA) for cleavage by a ribonuclease.

In RNAi process, long dsRNA is processed by a ribonuclease protein Dicer to short forms called small interfering RNA (siRNA). The siRNA is separated into guide (or antisense) strand and passenger (or sense) strand. The guide strand is integrated into RNA-induced-silencing-complex (RISC), which is a ribonuclease-containing multi-protein complex. The complex then specifically targets complementary gene transcripts for destruction.

RNAi has been shown to be a common cellular process in many eukaryotes. RISC, as well as Dicer, is conserved across the eukaryotic domain. RNAi is believed to play a role in the immune response to virus and other foreign genetic material.

Small interfering RNAs (siRNAs) are a class of short double-stranded RNA (dsRNA) molecules that play a variety of roles in biology. Most notably, it is involved in the RNA interference (RNAi) pathway where the siRNA interferes with the expression of a specific gene. In addition, siRNAs also play roles in the processes such as an antiviral mechanism or shaping the chromatin structure of a genome. In an embodiment, siRNA has a short (19-21 nt) double-strand RNA (dsRNA) region with 2-3 nucleotide 3' overhangs with 5'-phosphate and 3'-hydroxyl termini.

MicroRNAs (miRNAs) are a class of endogenous, single or double-stranded, about 22 nucleotide-long RNA molecules that regulate as much as 30% of mammalian genes (Czech, 2006; Eulalio et al., 2008; Mack, 2007). MiRNA represses protein production by blocking translation or causing transcript degradation. A miRNA may target 250-500 different mRNAs. MiRNA is the product of the Dicer digestion of pre-miRNA, which is the product of primary miRNA (pri-miRNA).

As used herein, antagomirs are miRNA inhibitors, and can be used in the silencing of endogenous miRNAs. As used herein, mimetics are miRNA agonists, and can be used to replace the miRNAs and downregulate mRNAs.

Dicer is a member of RNase III ribonuclease family. Dicer cleaves long double-stranded RNA (dsRNA), pre-micro-RNA (miRNA), and short hairpin RNA (shRNA) into short double-stranded RNA fragments called small interfering RNA (siRNA) about 20-25 nucleotides long, usually with a two-base overhang on the 3' end. Dicer catalyzes the first step in the RNA interference pathway and initiates formation of the RNA-induced silencing complex (RISC), whose catalytic component argonaute is an endonuclease capable of degrading messenger RNA (mRNA) whose sequence is complementary to that of the siRNA guide strand.

As used herein, an effective siRNA sequence is a siRNA that is effective in triggering RNAi to degrade the transcripts of a target gene. Not every siRNA complementary to the target gene is effective in triggering RNAi to degrade the transcripts of the gene. Indeed, time-consuming screening is usually necessary to identify an effective siRNA sequence. In an embodiment, the effective siRNA sequence is capable of reducing the expression of the target gene by more than 90%, more than 80%, more than 70%, more than 60%, more than 50%, more than 40%, or more than 30%.

The present invention provides a novel structural scaffold called asymmetric interfering RNA (aiRNA) that can be used to effect siRNA-like results, and also to modulate miRNA pathway activities (described in detail in co-owned PCT and U.S. applications filed on the same day as the present application under the title "Composition of Asymmetric RNA Duplex as MicroRNA Mimetic or Inhibitor" the entire content of which is incorporated herein by reference).

The novel structural design of aiRNA is not only functionally potent in effecting gene regulation, but also offers several advantages over the current state-of-art, RNAi regulators (mainly antisense, siRNA). Among the advantages, aiRNA can have RNA duplex structure of much shorter length than the current siRNA constructs, which should reduce the cost of synthesis and abrogate or reduce length-dependent triggering of nonspecific interferon-like immune responses from host cells. The shorter length of the passenger strand in aiRNA should also eliminate or reduce the passenger strand's unintended incorporation in RISC, and in turn, reduce off-target effects observed in miRNA-mediated gene silencing. AiRNA can be used in all areas that current miRNA-based technologies are being applied or contemplated to be applied, including biology research, R&D in biotechnology and pharmaceutical industries, and miRNA-based diagnostics and therapies.

2. The aiRNA Structural Scaffold

Elbashir, et al, tested several asymmetrical duplex RNA molecules as well as symmetrical siRNA molecules (Elbashir et al., 2001c). The asymmetrical duplex RNA molecules are listed in table 1 together with the corresponding siRNA molecules.

TABLE 1

B

5'-CGUACGCGGAAUACUUCG-5' (SEQ ID NO: 60)

UGCAUGCGCCUUAUGAAGCUU-5' (SEQ ID NO: 61)

5'-CGUACGCGGAAUACUUCGA (SEQ ID NO: 64)

UGCAUGCGCCUUAUGAAGCUU-5' (SEQ ID NO: 61)

TABLE 1-continued

```
                                   (SEQ ID NO: 65)
5'-CGUACGCGGAAUACUUCGAA
                                   (SEQ ID NO: 61)
   UGCAUGCGCCUUAUGAAGCUU-5'

(SEQ ID NO: 66)
5'-CGUACGCGGAAUACUUCGAAA
                                   (SEQ ID NO: 61)
   UGCAUGCGCCUUAUGAAGCUU-5'

(SEQ ID NO: 67)
5'-CGUACGCGGAAUACUUCGAAAU
                                   (SEQ ID NO: 61)
   UGCAUGCGCCUUAUGAAGCUU-5'

(SEQ ID NO: 68)
5'-CGUACGCGGAAUACUUCGAAAUG
                                   (SEQ ID NO: 61)
   UGCAUGCGCCUUAUGAAGCUU-5'

(SEQ ID NO: 69)
5'-CGUACGCGGAAUACUUCGAAAUGU
                                   (SEQ ID NO: 61)
   UGCAUGCGCCUUAUGAAGCUU-5'

(SEQ ID NO: 70)
5'-CGUACGCGGAAUACUUCGAAAUGUC
                                   (SEQ ID NO: 61)
   UGCAUGCGCCUUAUGAAGCUU-5'
```

C

```
                                   (SEQ ID NO: 60)
5'-CGUACGCGGAAUACUUCG
                                   (SEQ ID NO: 62)
   GUGCAUGCGCCUUAUGAAGCU-5'

(SEQ ID NO: 64)
5'-CGUACGCGGAAUACUUCGA
                                   (SEQ ID NO: 62)
   GUGCAUGCGCCUUAUGAAGCU-5'

(SEQ ID NO: 65)
5'-CGUACGCGGAAUACUUCGAA
                                   (SEQ ID NO: 62)
   GUGCAUGCGCCUUAUGAAGCU-5'

(SEQ ID NO: 66)
5'-CGUACGCGGAAUACUUCGAAA
                                   (SEQ ID NO: 62)
   GUGCAUGCGCCUUAUGAAGCU-5'

(SEQ ID NO: 67)
5'-CGUACGCGGAAUACUUCGAAAU
                                   (SEQ ID NO: 62)
   GUGCAUGCGCCUUAUGAAGCU-5'

(SEQ ID NO: 68)
5'-CGUACGCGGAAUACUUCGAAAUG
                                   (SEQ ID NO: 62)
   GUGCAUGCGCCUUAUGAAGCU-5'

(SEQ ID NO: 69)
5'-CGUACGCGGAAUACUUCGAAAUGU
                                   (SEQ ID NO: 62)
   GUGCAUGCGCCUUAUGAAGCU-5'

(SEQ ID NO: 70)
5'-CGUACGCGGAAUACUUCGAAAUGUC
                                   (SEQ ID NO: 62)
   GUGCAUGCGCCUUAUGAAGCU-5'
```

D

```
                                   (SEQ ID NO: 60)
5'-CGUACGCGGAAUACUUCG
                                   (SEQ ID NO: 63)
   AGUGCAUGCGCCUUAUGAAGC-5'
```

TABLE 1-continued

```
                                   (SEQ ID NO: 64)
5'-CGUACGCGGAAUACUUCGA
                                   (SEQ ID NO: 63)
   AGUGCAUGCGCCUUAUGAAGC-5'

(SEQ ID NO: 65)
5'-CGUACGCGGAAUACUUCGAA
                                   (SEQ ID NO: 63)
   AGUGCAUGCGCCUUAUGAAGC-5'

(SEQ ID NO: 66)
5'-CGUACGCGGAAUACUUCGAAA
                                   (SEQ ID NO: 63)
   AGUGCAUGCGCCUUAUGAAGC-5'

(SEQ ID NO: 67)
5'-CGUACGCGGAAUACUUCGAAAU
                                   (SEQ ID NO: 63)
   AGUGCAUGCGCCUUAUGAAGC-5'

(SEQ ID NO: 68)
5'-CGUACGCGGAAUACUUCGAAAUG
                                   (SEQ ID NO: 63)
   AGUGCAUGCGCCUUAUGAAGC-5'

(SEQ ID NO: 69)
5'-CGUACGCGGAAUACUUCGAAAUGU
                                   (SEQ ID NO: 63)
   AGUGCAUGCGCCUUAUGAAGC-5'

(SEQ ID NO: 70)
5'-CGUACGCGGAAUACUUCGAAAUGUC
                                   (SEQ ID NO: 63)
   AGUGCAUGCGCCUUAUGAAGC-5'
```

In comparison with corresponding symmetrical siRNA molecules, however, the asymmetrical duplex RNA molecules are incapable of effecting selective gene silencing (ibid).

The present invention is pertinent to asymmetrical duplex RNA molecules that are capable of effecting sequence-specific gene silencing. In an embodiment, a RNA molecule of the present invention comprises a first strand and a second strand, wherein the second strand is substantially complementary to the first strand, and forms a double-stranded region with the first strand, wherein the first strand is longer than the second strand; excluding the asymmetrical duplex RNA molecules disclosed in Elbashir (Elbashir et al., 2001c), specifically the asymmetrical duplex RNA molecules listed in Table 1. The RNA molecule comprises a double-stranded region, and two ends independently selected from the group consisting of a 5'-overhang, a 3'-overhang, and a blunt end. The RNA strand can have unmatched or imperfectly matched nucleotides.

In an embodiment, the first strand is at least 1 nt longer than the second strand. In a further embodiment, the first strand is at least 2, 3, 4, 5, 6, 7, 8, 9, 10, 11, 12, 13, 14, 15, 16, 17, 18, 19, or 20 nt longer than the second strand. In another embodiment, the first strand is 20-100 nt longer than the second strand. In a further embodiment, the first strand is 2-12 nt longer than the second strand. In an even further embodiment, the first strand is 3-10 nt longer than the second strand.

In an embodiment, the double-stranded region has a length of 3-98 bp. In a further embodiment, the double-stranded region has a length of 5-28 bp. In an even further embodiment, the double-stranded region has a length of 10-19 bp. The length of the double-stranded region can be 3, 4, 5, 6, 7, 8, 9, 10, 11, 12, 13, 14, 15, 18, 19, 20, 21, 22, 23, 24, 25, 26, 27, 28, 29, or 30 bp.

In an embodiment, the double-stranded region of the RNA molecule does not contain any mismatch or bulge. In another embodiment, the double-stranded region of the RNA molecule contains mismatch and/or bulge.

In an embodiment, when the first strand is

```
                                        (SEQ ID NO: 1)
5'-UUCGAAGUAUUCCGCGUACGU (SEQ ID NO: 2)
5'-UCGAAGUAUUCCGCGUACGUG
or
                                        (SEQ ID NO: 3)
5'-CGAAGUAUUCCGCGUACGUGA,
``` the second strand has a length of at most 17 nucleotides, or contains at least one mismatch with the first strand, or contains at least one modification.

In an alternative embodiment, the first strand is not

```
                                        (SEQ ID NO: 1)
5'-UUCGAAGUAUUCCGCGUACGU (SEQ ID NO: 2)
5'-UCGAAGUAUUCCGCGUACGUG
or
                                        (SEQ ID NO: 3)
5'-CGAAGUAUUCCGCGUACGUGA.
```

In an embodiment, the first strand comprises a sequence being substantially complimentary to a target mRNA sequence. In another embodiment, the second strand comprises a sequence being substantially complimentary to a target mRNA sequence.

The present invention is pertinent to asymmetrical double stranded RNA molecules that are capable of effecting gene silencing. In an embodiment, an RNA molecule of the present invention comprises a first strand and a second strand, wherein the second strand is substantially complementary, or partially complementary to the first strand, and the first strand and the second strand form at least one double-stranded region, wherein the first strand is longer than the second strand (length asymmetry). The RNA molecule of the present invention has at least one double-stranded region, and two ends independently selected from the group consisting of a 5'-overhang, a 3'-overhang, and a blunt end (e.g., see FIGS. 1A, 2A-2D).

In the field of making small RNA regulators where changes, additions and deletions of a single nucleotide can critically affect the functionality of the molecule (Elbashir et al., 2001c), the aiRNA scaffold provides a structural platform distinct from the classic siRNA structure of 21-nt double-strand RNA which is symmetric in each strand and their respective 3' overhangs. Further, the aiRNA of the present invention provides a much-needed new approach in designing a new class of small molecule regulators that, as shown by data included in the examples below, can overcome obstacles currently encountered in RNAi-based researches and drug development. For example, data from aiRNAs that structurally mimic siRNAs show that aiRNAs are more efficacious, potent, rapid-onset, durable, and specific than siRNAs in inducing gene silencing.

Figure 1A:
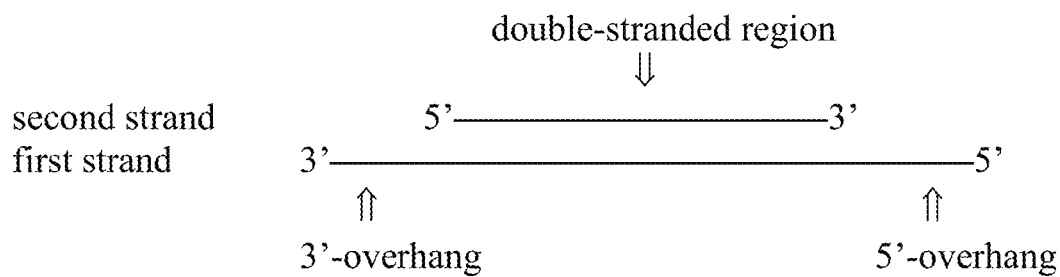
FIG. 1: (A) shows the structure of a duplex RNA molecule that has both a 3'-overhang and a 5'-overhang on the first strand. (B) shows the structure of a duplex RNA molecule that has both a 3'-overhang and a 5'-overhang on the first strand, and a nick in the duplex. (C) shows the structure of a duplex RNA molecule that has both a 3'-overhang and a 5'-overhang on the first strand, and a gap in the second strand.
Figure 1B:
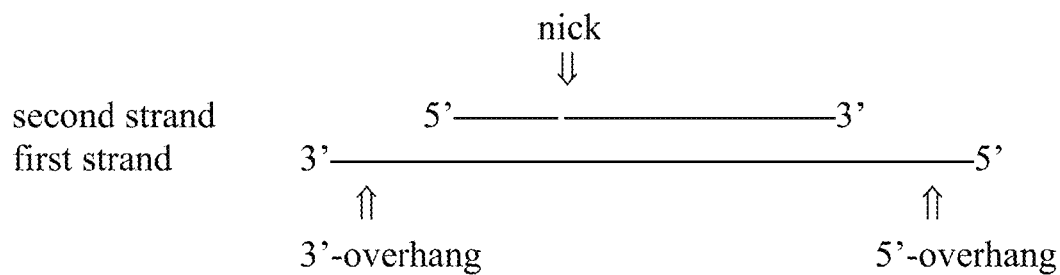
Figure 1C:
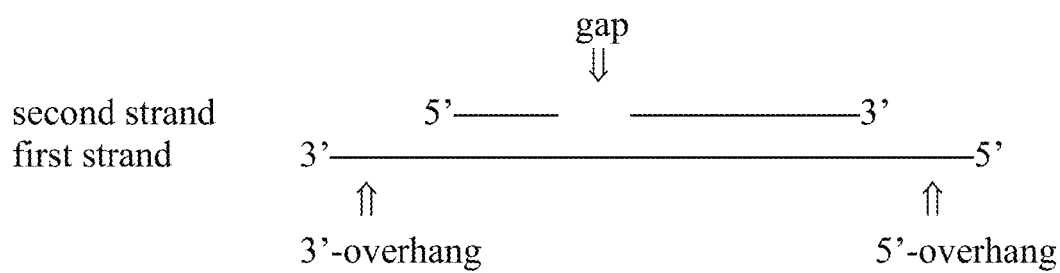

Any single-stranded region of the RNA molecule of the invention, including any terminal overhangs and gaps in between two double-stranded regions, can be stabilized against degradation, either through chemical modification or secondary structure. The RNA strands can have unmatched or imperfectly matched nucleotides. Each strand may have one or more nicks (a cut in the nucleic acid backbone, e.g., see FIG. 18), gaps (a fragmented strand with one or more missing nucleotides, e.g, see FIG. 1C), and modified nucleotides or nucleotide analogues. Not only can any or all of the nucleotides in the RNA molecule chemically modified, each strand may be conjugated with one or more moieties to enhance its functionality, for example, with moieties such as one or more peptides, antibodies, antibody fragments, aptamers, polymers and so on.

In an embodiment, the first strand is at least 1 nt longer than the second strand. In a further embodiment, the first strand is at least 2, 3, 4, 5, 6, 7, 8, 9, 10, 11, 12, 13, 14, 15, 16, 17, 18, 19, or 20 nt longer than the second strand. In another embodiment, the first strand is 20-100 nt longer than the second strand. In a further embodiment, the first strand is 2-12 nt longer than the second strand. In an even further embodiment, the first strand is 3-10 nt longer than the second strand.

In an embodiment, the first strand, or the long strand, has a length of 5-100 nt, or preferably 10-30 or 12-30 nt, or more preferably 15-28 nt. In one embodiment, the first strand is 21 nucleotides in length. In an embodiment, the second strand, or the short strand, has a length of 3-30 nt, or preferably 3-29 nt or 10-26 nt, or more preferably 12-26 nt. In an embodiment, the second strand has a length of 15 nucleotides.

In an embodiment, the double-stranded region has a length of 3-98 bp. In a further embodiment, the double-stranded region has a length of 5-28 bp. In an even further embodiment, the double-stranded region has a length of 10-19 bp. The length of the double-stranded region can be 3, 4, 5, 6, 7, 8, 9, 10, 11, 12, 13, 14, 15, 16, 17, 18, 19, 20, 21, 22, 23, 24, 25, 26, 27, 28, 29, or 30 bp.

In an embodiment, the double-stranded region of the RNA molecule does not contain any mismatch or bulge, and the two strands are perfectly complementary to each other in the double-stranded region. In another embodiment, the double-stranded region of the RNA molecule contains mismatch and/or bulge.

In an embodiment, the terminal overhang is 1-10 nucleotides. In a further embodiment, the terminal overhang is 1-8 nucleotides. In another embodiment, the terminal overhang is 3 nt.

2.1. The Duplex RNA Molecule with Both a 5'-Overhang and a 3'-Overhang on the First Strand Referring to FIG. 1A, in one embodiment of the present invention, the double stranded RNA molecule has both a 5'-overhang and a 3'-overhang on the first strand. The RNA molecule comprises a first strand and a second strand; the first strand and the second strand form at least one double-stranded region with substantially complementary sequences, wherein the first strand is longer than the second strand. On the first strand, flanking the double-stranded region, there is an unmatched overhang on both the 5' and 3' termini.

In an embodiment, the first strand is at least 2 nt longer than the second strand. In a further embodiment, the first strand is at least 3, 4, 5, 6, 7, 8, 9, 10, 11, 12, 13, 14, 15, 16, 17, 18, 19, or 20 nt longer than the second strand. In another embodiment, the first strand is 20-100 nt longer than the second strand. In a further embodiment, the first strand is 2-12 nt longer than the second strand. In an even further embodiment, the first strand is 3-10 nt longer than the second strand.

In an embodiment, the first strand has a length of 5-100 nt. In a further embodiment, the first strand has a length of 5-100 nt, and the second strand has a length from 3-30 nucleotides. In an even further embodiment, the first strand has a length of 5-100 nt, and the second strand has a length from 3-18 nucleotides.

In an embodiment, the first strand has a length from 10-30 nucleotides. In a further embodiment, the first strand has a length from 10-30 nucleotides, and the second strand has a length from 3-28 nucleotides. In an even further embodiment, the first strand has a length from 10-30 nucleotides, and the second strand has a length from 3-19 nucleotides.

In an embodiment, the first strand has a length from 12-26 nucleotides. In a further embodiment, the first strand has a length from 12-26 nucleotides, and the second strand has a length from 10-24 nucleotides. In an even further embodiment, the first strand has a length from 12-26 nucleotides, and the second strand has a length from 10-19 nucleotides.

In an embodiment, the first strand has a length of 5, 6, 7, 8, 9, 10, 11, 12, 13, 14, 15, 16, 17, 18, 19, 20, 21, 22, 23, 24, 25, 26, 27, 28, 29, or 30 nt. In another embodiment, the second strand has a length of 3, 4, 5, 6, 7, 8, 9, 10, 11, 12, 13, 14, 15, 16, 17, 18, 19, 20, 21, 22, 23, 24, 25, 26, 27, or 28 nt.

In an embodiment, the first strand has a length of 21 nt, and the second strand has a length of 15 nt.

In an embodiment, the 3'-overhang has a length of 1-10 nt. In a further embodiment, the 3'-overhang has a length of 1-8 nt. In an even further embodiment, the 3'-overhang has a length of 2-6 nt. In one embodiment, the 3'-overhang has a length of 1, 2, 3, 4, 5, 6, 7, 8, 9, or 10 nt.

In an embodiment, the 5'-overhang has a length of 1-10 nt. In a further embodiment, the 5'-overhang has a length of 1-6 nt. In an even further embodiment, the 5'-overhang has a length of 2-4 nt. In one embodiment, the 5'-overhang has a length of 1, 2, 3, 4, 5, 6, 7, 8, 9, or 10 nt.

In an embodiment, the length of the 3'-overhang is equal to that of the 5'-overhang. In another embodiment, the 3'-overhang is longer than the 5'-overhang. In an alternative embodiment, the 3'-overhang is shorter than the 5'-overhang.

In an embodiment, the duplex RNA molecule comprises a double-stranded region of substantially complementary sequences of about 15 nt, a 3-nt 3'-overhang, and a 3-nt 5'-overhang. The first strand is 21 nt and the second strand is 15 nt. In one feature, the double-stranded region of various embodiments consists of perfectly complementary sequences. In an alternative feature, the double strand region includes at least one nick (FIG. 1B), gap (FIG. 1C), or mismatch (bulge or loop).

In an embodiment, the double-stranded region has a length of 3-98 bp. In a further embodiment, the double-stranded region has a length of 5-28 bp. In an even further embodiment, the double-stranded region has a length of 10-19 bp. The length of the double-stranded region can be 3, 4, 5, 6, 7, 8, 9, 10, 11, 12, 13, 14, 15, 18, 19, 20, 21, 22, 23, 24, 25, 26, 27, 28, 29, or 30 bp. There can be more than one double-stranded region.

In an embodiment, the first strand is the antisense strand, which is capable of targeting a substantially complementary gene transcript such as a messenger RNA (mRNA) for gene silencing either by cleavage or by translation repression.

The present invention also provides a duplex RNA molecule comprising a first strand with a length from 18-23 nucleotides and a second strand with a length from 12-17 nucleotides, wherein the second strand is substantially complementary to the first strand, and forms a double-stranded region with the first strand, wherein the first strand has a 3'-overhang from 1-9 nucleotides, and a 5'-overhang from 1-8 nucleotides, wherein said duplex RNA molecule is capable of effecting selective gene silencing in a eukaryotic cell. In an embodiment, the first strand comprises a sequence being substantially complementary to a target mRNA sequence.

In an embodiment, the first strand has a length of 20, 21, or 22 nucleotides. In another embodiment, the second strand has a length of 14, 15, or 16 nucleotides.

I an embodiment, the first strand has a length of 21 nucleotides, and the second strand has a length of 15 nucleotides. In a further embodiment, the first strand has a 3'-overhang of 1, 2, 3, 4, 5, or 6 nucleotides. In an even further embodiment, the first strand has a 3'-overhang of 3 nucleotides.

2.2. The Duplex RNA Molecule with a Blunt End and a 5'-Overhang or a 3'-Overhang on the First Strand In one embodiment, the duplex RNA molecule comprises a double-stranded region, a blunt end, and a 5'-overhang or a 3'-overhang (see, e.g., FIGS. 2A and 2B). The RNA molecule comprises a first strand and a second strand, wherein the first strand and the second strand form a double-stranded region, wherein the first strand is longer than the second strand.

In an embodiment, the double-stranded region has a length of 3-98 bp. In a further embodiment, the double-stranded region has a length of 5-28 bp. In an even further embodiment, the double-stranded region has a length of 10-18 bp. The length of the double-stranded region can be 3, 4, 5, 6, 7, 8, 9, 10, 11, 12, 13, 14, 15, 18, 19, 20, 21, 22, 23, 24, 25, 26, 27, 28, 29, or 30 bp. The double-stranded region can have features similar to those described with regard to other embodiments and are not necessarily repeated here. For example, the double-stranded region can consist of perfectly complementary sequences or include at least one nick, gap, or mismatch (bulge or loop).

In an embodiment, the first strand is at least 1 nt longer than the second strand. In a further embodiment, the first strand is at least 1, 2, 3, 4, 5, 6, 7, 8, 9, 10, 11, 12, 13, 14, 15, 16, 17, 18, 19, or 20 nt longer than the second strand. In another embodiment, the first strand is 20-100 nt longer than the second strand. In a further embodiment, the first strand is 2-12 nt longer than the second strand. In an even further embodiment, the first strand is 4-10 nt longer than the second strand.

In an embodiment, the first strand has a length of 5-100 nt. In a further embodiment, the first strand has a length of 5-100 nt, and the second strand has a length from 3-30 nucleotides. In an even further embodiment, the first strand has a length of 10-30 nt, and the second strand has a length from 3-19 nucleotides. In another embodiment, the first strand has a length from 12-26 nucleotides, and the second strand has a length from 10-19 nucleotides.

Figure 2A:
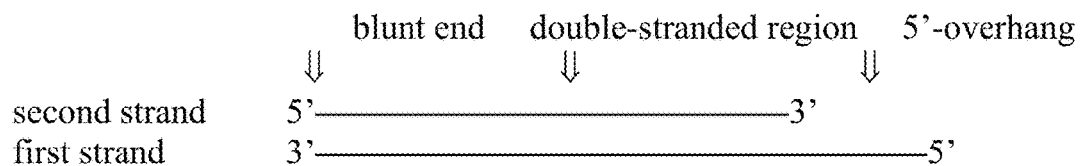
FIG. 2: (A) shows the structure of a duplex RNA molecule that has a blunt end, and a 5'-overhang on the first strand. (B) shows the structure of a duplex RNA molecule that has a blunt end, and a 3'-overhang on the first strand. (C) shows the structure of a duplex RNA molecule that has 3'-overhangs on both ends of the duplex and that the first strand is longer than the second strand. (D) shows the structure of a duplex RNA molecule that has 5'-overhangs on both ends of the duplex and that the first strand is longer than the second strand.
Figure 2B:
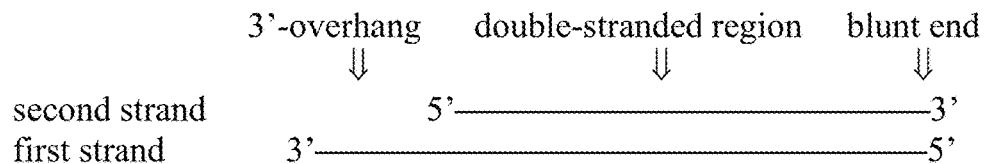

In an embodiment, the duplex RNA molecule comprises a double-stranded region, a blunt end, and a 3'-overhang (see, e.g., FIG. 2B).

In an embodiment, the 3'-overhang has a length of 1-10 nt. In a further embodiment, the 3'-overhang has a length of 1-8 nt. In an even further embodiment, the 3'-overhang has a length of 2-6 nt. In one embodiment, the 3'-overhang has a length of 1, 2, 3, 4, 5, 6, 7, 8, 9, or 10 nt.

In an alternative embodiment, the duplex RNA molecule comprises a double-stranded region, a blunt end, and a 5'-overhang (see, e.g., FIG. 2A).

In an embodiment, the 5'-overhang has a length of 1-10 nt. In a further embodiment, the 5'-overhang has a length of 1-6 nt. In an even further embodiment, the 5'-overhang has a length of 2-4 nt. In one embodiment, the 5'-overhang has a length of 1, 2, 3, 4, 5, 6, 7, 8, 9, or 10 nt.

2.3. The Duplex RNA Molecule with Two 5'-Overhangs or Two 3'-Overhangs

Figure 2C:
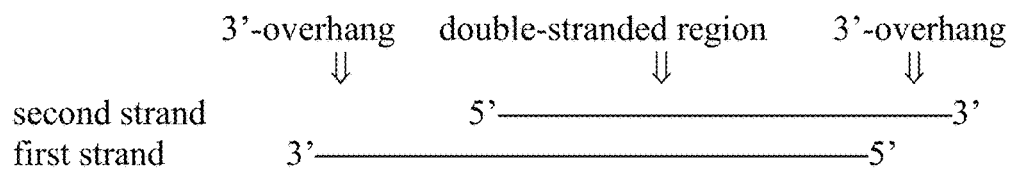
Figure 2D:
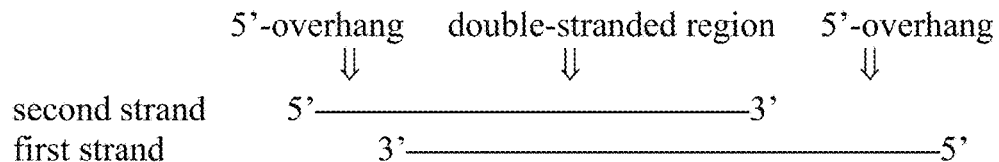

In one embodiment, the duplex RNA molecule comprises a double-stranded region, and two 3'-overhangs or two 5'-overhangs (see, e.g., FIGS. 2C and 2D). The RNA molecule comprises a first strand and a second strand, wherein the first strand and the second strand form a double-stranded region, wherein the first strand is longer than the second strand.

In an embodiment, the double-stranded region has a length of 3-98 bp. In a further embodiment, the double-stranded region has a length of 5-28 bp. In an even further embodiment, the double-stranded region has a length of 10-18 bp. The length of the double-stranded region can be 3, 4, 5, 6, 7, 8, 9, 10, 11, 12, 13, 14, 15, 18, 19, 20, 21, 22, 23, 24, 25, 26, 27, 28, 29, or 30 bp.

In an embodiment, the first strand is at least 1 nt longer than the second strand. In a further embodiment, the first strand is at least 1, 2, 3, 4, 5, 6, 7, 8, 9, 10, 11, 12, 13, 14, 15, 16, 17, 18, 19, or 20 nt longer than the second strand. In another embodiment, the first strand is 20-100 nt longer than the second strand. In a further embodiment, the first strand is 2-12 nt longer than the second strand. In an even further embodiment, the first strand is 4-10 nt longer than the second strand.

In an embodiment, the first strand has a length of 5-100 nt. In a further embodiment, the first strand has a length of 5-100 nt, and the second strand has a length from 3-30 nucleotides. In an even further embodiment, the first strand has a length of 10-30 nt, and the second strand has a length from 3-18 nucleotides. In another embodiment, the first strand has a length from 12-26 nucleotides, and the second strand has a length from 10-16 nucleotides.

In an alternative embodiment, the duplex RNA molecule comprises a double-stranded region, and two 3'-overhangs (see, e.g., FIG. 2C). The double-stranded region shares similar features as described with regard to other embodiments.

In an embodiment, the 3'-overhang has a length of 1-10 nt. In a further embodiment, the 3'-overhang has a length of 1-6 nt. In an even further embodiment, the 3'-overhang has a length of 2-4 nt. In one embodiment, the 3'-overhang has a length of 1, 2, 3, 4, 5, 6, 7, 8, 9, or 10 nt.

In an embodiment, the duplex RNA molecule comprises a double-stranded region, and two 5'-overhangs (see, e.g., FIG. 2D).

In an embodiment, the 5'-overhang has a length of 1-10 nt. In a further embodiment, the 5'-overhang has a length of 1-6 nt. In an even further embodiment, the 5'-overhang has a length of 2-4 nt. In one embodiment, the 3'-overhang has a length of 1, 2, 3, 4, 5, 6, 7, 8, 9, or 10 nt.

3. The Design of aiRNAs siRNAs and miRNAs are widely used as research tools, and developed as drug candidates. (see, e.g., Dykxhoorn, Novina & Sharp. *Nat. Rev. Mol. cell Biol.* 4:457-467 (2003); Kim & Rossi, *Nature Rev. Genet.* 8:173-184 (2007); de Fougerolles, et al. Nature Rev. Drug Discov. 6:443-453 (2007); Czech, NEJM 354:1194-1195 (2006); and Mack, Nature Biotech. 25:631-638 (2007)). The duplex RNA molecules of the present invention, i.e., aiRNAs, can be derived from siRNAs and miRNAs known in the field.

The present invention provides a method of converting an siRNA or a miRNA into an aiRNA. The conversion results in a new duplex RNA molecule that has at least one property improved in comparison to the original molecule. The property can be size, efficacy, potency, the speed of onset, durability, synthesis cost, off-target effects, interferon response, or delivery.

In an embodiment, the original molecule is a duplex RNA molecule, such as an siRNA. The duplex RNA molecule comprises an antisense strand (e.g., a guide strand) and a sense strand (e.g. a passenger strand) that form at least one double-stranded region. The method comprises changing the length of one or both strands so that the antisense strand is longer than the sense strand. In an embodiment, sense passenger strand is shortened. In another embodiment, the antisense strand is elongated. In an even further embodiment, the sense strand is shortened and the antisense strand is elongated. The antisense and sense RNA strands, intact or with changed size, can be synthesized, and then combined under conditions, wherein an aiRNA molecule is formed.

In a further embodiment, the method comprises changing the length of the antisene and/or sense strand so that the duplex RNA molecule is formed having at least one of a 3'-overhang of 1-6 nucleotides and a 5'-overhang of 1-6 nucleotides.

Alternatively, the duplex RNA molecules of the present invention can be designed de novo. A duplex RNA molecule of the present invention can be designed taking advantage of the design methods for siRNAs and miRNAs, such as the method of gene walk.

An RNA molecule of the present invention can be designed with bioinformatics approaches, and then tested in vitro and in vivo to determine its modulating efficacy against the target gene and the existence of any off-target effects. Based on these studies, the sequences of the RNA molecules can then be selected and modified to improve modulating efficacy against the target gene, and to minimize off-target effects. (see e.g., Patzel, *Drug Discovery Today* 12:139-148 (2007)).

3.1. Unmatched or Mismatched Region in the Duplex RNA Molecule

The two single strands of the aiRNA duplex can have at least one unmatched or imperfectly matched region containing, e.g., one or more mismatches. In one embodiment, the unmatched or imperfectly matched region is at least one end region of the RNA molecule, including an end region with a blunt end, an end region with a 3'-recess or a 5' overhang, and an end region with a 5' recess or a 3' overhang. As used herein, the end region is a region of the RNA molecule including one end and the neighboring area.

In an embodiment, the unmatched or imperfectly matched region is in a double-stranded region of the aiRNA molecule. In a further embodiment, the asymmetric RNA duplex has an unmatched bulge or loop structure.

3.2. Sequence Motifs in the Duplex RNA Molecule

In the design of an aiRNA molecule of the invention, the overall GC content may vary. In an embodiment, the GC content of the double-stranded region is 20-70%. In a further embodiment, the GC content of the double-stranded region is less than 50%, or preferably 30-50%, to make it easier for strand separation as the G-C pairing is stronger than the A-U pairing.

The nucleotide sequence at a terminal overhang, in some embodiments, e.g., the 5' terminal, can be designed independently from any template sequence (e.g., a target mRNA sequence), i.e., does not have to be substantially complementary to a target mRNA (in the case of an siRNA or miRNA mimetic) or a target miRNA (in the case of miRNA inhibitor). In one embodiment, the overhang, e.g., at the 5' or the 3', of the longer or antisense strand, is an "AA", "UU" or "dTdT" motif, which have exhibited increased efficacy in comparison to some other motifs. In an embodiment, the 5' overhang of the longer or antisense strand has an "AA" motif. In another embodiment, the 3' overhang of the longer or antisense strand has a "UU" motif.

3.3. Nucleotide Substitution

One or more of the nucleotides in the RNA molecule of the invention can be substituted with deoxynucleotides or modified nucleotides or nucleotide analogues. The substitution can take place anywhere in the RNA molecule, e.g., one or both of the overhang regions, and/or a double-stranded region. In some cases, the substitution enhances a physical property of the RNA molecule such as strand affinity, solubility and resistance to RNase degradation or enhanced stability otherwise.

In one embodiment, the modified nucleotide or analogue is a sugar-, backbone-, and/or base-modified ribonucleotide. The backbone-modified ribonucleotide may have a modification in a phosphodiester linkage with another ribonucleotide. In an embodiment, the phosphodiester linkage in the RNA molecule is modified to include at least a nitrogen and/or sulphur heteroatom. In an embodiment, the modified nucleotide or analogue is an unusual base or a modified base. In an embodiment, the modified nucleotide or analogue is inosine, or a tritylated base.

In a further embodiment, the nucleotide analogue is a sugar-modified ribonucleotide in which the 2'-OH group is replaced by a group selected from the group consisting of H, OR, R, halo, SH, SR, $NH_2$, NHR, $NR_2$, and CN, wherein each R is independently selected from the group consisting of C1-C6 alkyl, alkenyl and alkynyl, and halo is selected from the group consisting of F, Cl, Br and I.

In one embodiment, the nucleotide analogue is a backbone-modified ribonucleotide containing a phosphothioate group.

4. The Utilities

The present invention also provides a method of modulating gene expression in a cell or an organism (silencing method). The method comprises the steps of contacting said cell or organism with the duplex RNA molecule under conditions wherein selective gene silencing can occur, and mediating a selective gene silencing effected by the said duplex RNA molecule towards a target nucleic acid having a sequence portion substantially corresponding to the double-stranded RNA.

In an embodiment, the contacting step comprises the step of introducing said duplex RNA molecule into a target cell in culture or in an organism in which the selective gene silencing can occur. In a further embodiment, the introducing step comprises transfection, lipofection, infection, electroporation, or other delivery technologies.

In an embodiment, the silencing method is used for determining the function or utility of a gene in a cell or an organism.

The silencing method can be used for modulating the expression of a gene in a cell or an organism. In an embodiment, the gene is associated with a disease, e.g., a human disease or an animal disease, a pathological condition, or an undesirable condition. In a further embodiment, the gene is a gene of a pathogenic microorganism. In an even further embodiment, the gene is a viral gene. In another embodiment, the gene is a tumor-associated gene.

In an alternative embodiment, the gene is a gene associated with autoimmune disease, inflammatory diseases, degenerative diseases, infectious diseases, proliferative diseases, metabolic diseases, immune-mediated disorders, allergic diseases, dermatological diseases, malignant diseases, gastrointestinal disorders, respiratory disorders, cardiovascular disorders, renal disorders, rheumatoid disorders, neurological disorders, endocrine disorders, and aging.

4.1. Research Tools

The RNA molecules of the present invention can be used to create gene "knockdown" in animal models as opposed to genetically engineered knockout models to discover gene functions. The methods can also be used to silence genes in vitro. For example, aiRNA can be transfected to cells. AiRNA can be used to 1 as a research tool in drug target/pathway identification and validation, and other biomedical research in drug research and development.

4.2 Therapeutic Uses

The RNA molecules of the present invention can be used for the treatment and or prevention of various diseases or undesirable conditions, including the diseases summarized (Czech, 2006; de Fougerolles et al., 2007; Dykxhoorn et al., 2003; Kim and Rossi, 2007; Mack, 2007).

In an embodiment, the present invention can be used as a cancer therapy or to prevent cancer. The RNA molecules of the present invention can be used to silence or knock down genes involved with cell proliferation or other cancer phenotypes. Examples of these genes are k-Ras, β-catenin, Nbs1, EF2, Stat3, PTEN, p70S6K, mTOR, Rsk1, PCNA, Parp1, Survivin, NQO1, and p21. Specifically, k-Ras and β-catenin are therapeutic genes of colon cancer. These oncogenes are active and relevant in the majority of clinical cases.

These RNA molecules can also be used to silence or knockdown non-cancer gene targets. The RNA molecules of the invention can also be used to treat or prevent ocular diseases, (e.g., age-related macular degeneration (AMD) and diabetic retinopathy (DR)); infectious diseases (e.g. HIV/AIDS, hepatitis B virus (HBV), hepatitis C virus (HCV), human papillomavirus (HPV), herpes simplex virus (HSV), RCV, cytomegalovirus (CMV), dengue fever, west Nile virus); respiratory diseases (e.g., respiratory syncytial virus (RSV), asthma, cystic fibrosis); neurological diseases (e.g., Huntingdon's disease (HD), amyotrophic lateral sclerosis (ALS), spinal cord injury, Parkinson's disease, Alzheimer's disease, pain); cardiovascular diseases; metabolic disorders (e.g., diabetes); genetic disorders; and inflammatory conditions (e.g., inflammatory bowel disease (IBD), arthritis, rheumatoid disease, autoimmune disorders), dermatological diseases.

Various genes can be silenced using the asymmetrical duplex RNA molecule of the present invention. In an embodiment, the first strand comprises a sequence being substantially complimentary to the target mRNA sequence of a gene selected from the group consisting of a developmental gene, an oncogene, a tumor suppresser gene, and an enzyme gene, and a gene for an adhesion molecule, a cyclin kinase inhibitor, a Wnt family member, a Pax family member, a Winged helix family member, a Hox family member, a cytokine/lymphokine or its receptor, a growth/differentiation factor or its receptor, a neurotransmitter or its receptor, ABLI, BCL1, BCL2, BCL6, CBFA2, CBL, CSFIR, ERBA, ERBB, EBRB2, ETS1, ETS1, ETV6, FGR, FOS, FYN, HCR, HRAS, JUN, KRAS, LCK, LYN, MDM2, MLL, MYB, MYC, MYCL1, MYCN, NRAS, PIM1, PML, RET, SRC, TAL1, TCL3 and YES) (e. g., APC, BRCA1, BRCA2, MADH4, MCC, NF1, NF2, RB1, TP53, WT1, an ACP desaturase or hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, a DNA or RNA polymerase, a galactosidase, a glucanase, a glucose oxidase, a GTPase, a helicase, a hemicellulase, an integrase, an invertase, an isomerase, a kinase, a lactase, a lipase, a lipoxygenase, a lysozyme, a pectinesterase, a peroxidase, a phosphatase, a phospholipase, a phosphorylase, a polygalacturonase, a proteinase or peptideases, a pullanase, a recombinase, a reverse transcriptase, a topoisomerase, a xylanase, k-RAS, β-Catenin, Rsk1, PCNA, p70S6K, Survivin, mTOR, PTEN, Parp1, or p21.

The present invention provides a method to treat a disease or undesirable condition. The method comprises using the asymmetrical duplex RNA molecule to effect gene silencing of a gene associated with the disease or undesirable condition.

4.3. Converting the RNA Molecules (aiRNA) into Drugs 4.3.1. Modifications of the RNA Molecules Naked RNA molecules are relatively unstable and can be degraded in vivo relatively quickly. Chemical modifications can be introduced to the RNA molecules of the present invention to improve their half-life and to further reduce the risk of non-specific effects of gene targeting, without reducing their biological activities.

The modifications of RNA molecules have been investigated to improve the stability of various RNA molecules, including antisense RNA, ribozyme, aptamer, and RNAi (Chiu and Rana, 2003; Czauderna et al., 2003; de Fougerolles et al., 2007; Kim and Rossi, 2007; Mack, 2007; Zhang et al., 2006; and Schmidt, *Nature Biotech.* 25:273-275 (2007))

Any stabilizing modification known to a skill in the art can be used to improve the stability of the RNA molecules of the present invention. Within the RNA molecules of the present invention, chemical modifications can be introduced to the phosphate backbone (e.g., phosphorothioate linkages), the ribose (e.g., locked nucleic acids, 2'-deoxy-2'-fluorouridine, 2'-O-methyl), and/or the base (e.g., 2'-fluoropyrimidines). Several examples of such chemical modifications are summarized in the following.

Chemical modifications at the 2' position of the ribose, such as 2'-O-methylpurines and 2'-fluoropyrimidines, which increase resistance to endonuclease activity in serum, can be adopted to the stabilize the RNA molecules of the present invention. The position for the introduction of the modification should be carefully selected to avoid significantly reducing the silencing potency of the RNA molecule. For example, the modifications on 5' end of the guide strand can reduce the silencing activity. On the other hand, 2'-O-methyl modifications can be staggered between the two RNA strands at the double-stranded region to improve the stability while reserving the gene silencing potency. The 2'-O-methyl modifications can also eliminate or reduce the interferon induction.

Another stabilizing modification is phosphorothioate (P=S) linkage. The introduction of phosphorothioate (P=S) linkage into the RNA molecules, e.g., at the 3'-overhang, can provide protection against exonuclease.

The introduction of deoxyribonucleotides into the RNA molecules can also reduce the manufacture cost, and increase stability.

In an embodiment, the 3'-overhang, 5'-overhang, or both are stabilized against degradation.

In an embodiment, the RNA molecule contains at least one modified nucleotide or its analogue. In a further embodiment, the modified ribonucleotide is modified at its sugar, backbone, base, or any combination of the three.

In an embodiment, the nucleotide analogue is a sugar-modified ribonucleotide. In a further embodiment, the 2'-OH group of the nucleotide analogue is replaced by a group selected from H, OR, R, halo, SH, SR, $NH_2$, NHR, $NR_2$, or CN, wherein each R is independently C1-C6 alkyl, alkenyl or alkynyl, and halo is F, Cl, Br or I.

In an alternative embodiment, the nucleotide analogue is a backbone-modified ribonucleotide containing a phosphothioate group.

In an embodiment, the duplex RNA molecule contains at least one deoxynucleotide. In a further embodiment, the first strand comprises 1-6 deoxynucleotides. In an even further embodiment, the first strand comprises 1-3 deoxynucleotides. In another embodiment, the 3'-overhang comprises 1-3 deoxynucleotides. In a further embodiment, the 5'-overhang comprises 1-3 deoxynucleotides. In an alternative embodiment, the second strand comprises 1-5 deoxynucleotides.

In an embodiment, the duplex RNA molecule comprises a 3'-overhang or 5'-overhang that contains at least one deoxynucleotide. In another embodiment, the RNA the 3'-overhang and/or 5'-overhang consists of deoxynucleotides.

In an embodiment, the duplex RNA molecule is conjugated to an entity. In a further embodiment, the entity is selected from the group consisting of peptide, antibody, polymer, lipid, oligonucleotide, and aptamer.

In another embodiment, the first strand and the second strand are joined by a chemical linker.

4.4. In Vivo Delivery of the RNA Molecules

One major obstacle for the therapeutic use of RNAi is the delivery of siRNA to the target cell (Zamore and Aronin, 2003). Various approaches have been developed for the delivery of RNA molecules, especially siRNA molecules (de Fougerolles et al., 2007; Dykxhoom et al., 2003; Kim and Rossi, 2007). Any delivery approach known to a skill of the art can be used for the delivery of the RNA molecules of the present invention.

Major issues in delivery include instability in senim, non-specific distribution, tissue barriers, and non-specific interferon response (Lu & Woodle, *Methods in Mol Biology* 437: 93-107 (2008)). Compared to their siRNA and miRNA counterparts, aiRNA molecules possess several advantages that should make a wider ranger of methods available for delivery purpose. First, aiRNAs can be designed to be smaller than their siRNA and miRNA counterparts, therefore, reducing or eliminating any interferon responses. Second, aiRNAs are more potent, faster-onsetting, more efficacious and lasts longer, therefore, less amount/dosage of aiRNAs is required to achieve a therapeutic goal. Third, aiRNA are double stranded and more stable than single-stranded antisense oligos and miRNAs, and they can be further modified chemically to enhance stability. Therefore, the RNA molecules of the invention can be delivered into a subject via a variety of systemic or local delivery routes. In some embodiments, molecules of the invention are delivered through systemic delivery routes include intra-venous (I.V.) and intraperitoneal (ip). In other embodiments, molecules of the invention are delivered through local delivery routes, e.g., intra-nasal, intra-vitreous, intra-tracheal, intra-cerebral, intra-muscle, intra-articular, and intra-tumor.

Examples of the delivery technologies include direct injection of naked RNA molecules, conjugation of the RNA molecules to a natural ligand such as cholesterol, or an aptamer, liposome-formulated delivery, and non-covalently binding to antibody-protamine fusion proteins. Other carrier choices include positive charged carriers (e.g., cationic lipids and polymers) and various protein carriers. In one embodiment, the delivery of the molecules of the invention uses a ligand-targeted delivery system based on the cationic liposome complex or polymer complex systems (Woodle, et al. *J Control Release* 74: 309-311; Song, et al. *Nat Biotechnol.* 23(6): 709-717 (2005); Morrissey et al. *Nat Biotechnol.* 23(8): 1002-1007 (2005)). In one embodiment, molecules of the invention is formulated with a collagen carrier, e.g., atelocollagen, for in vivo delivery. Atelocollagen has been reported to protect siRNA from being digested by RNase and to enable sustained release (Minakuchi, et al. *Nucleic Acids Res.* 32: e109 (2004); Takei et al. *Cancer Res.* 64: 3365-3370 (2004)). In another embodiment, molecules of the invention are formulated with nanoparticles or form a nanoemulsion, e.g., RGD peptide ligand targeted nanoparticles. It has been shown that different siRNA oligos can be combined in the same RGD ligand targeted nanoparticle to target several genes at the same time (Woodle et al. *Materials Today* 8 (suppl 1): 34-41 (2005)).

Viral vectors can also be used for the delivery of the RNA molecules of the present invention. In an embodiment, lentiviral vectors are used to deliver the RNA molecule transgenes that integrate into the genome for stable expression. In another embodiment, adenoviral and adeno-associated virus (AAV) are used to deliver the RNA molecule transgenes that do not integrate into the genome and have episomal expression.

Moreover, bacteria can be used for the delivery of the RNA molecules of the present invention (Xiang et al., 2006).

5. The Pharmaceutical Compositions and Formulations

The present invention further provided a pharmaceutical composition. The pharmaceutical comprises as an active agent at least one asymmetrical duplex RNA molecule and one or more carriers selected from the group consisting of a pharmaceutical carrier, a positive-charge carrier, a liposome, a protein carrier, a polymer, a nanoparticle, a nanoemulsion, a lipid, and a lipoid. In an embodiment, the composition is for diagnostic applications, or for therapeutic applications.

The pharmaceutical compositions and formulations of the present invention can be the same or similar to the pharmaceutical compositions and formulations developed for siRNA, miRNA, and antisense RNA (de Fougerolles et al., 2007; Kim and Rossi, 2007), except for the RNA ingredient. The siRNA, miRNA, and antisense RNA in the pharmaceutical compositions and formulations can be replaced by the duplex RNA molecules of the present information. The pharmaceutical compositions and formulations can also be further modified to accommodate the duplex RNA molecules of the present information.

A "pharmaceutically acceptable salt" or "salt" of the disclosed duplex RNA molecule is a product of the disclosed duplex RNA molecule that contains an ionic bond, and is typically produced by reacting the disclosed duplex RNA molecule with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed duplex RNA molecules in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed duplex RNA molecule or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a duplex RNA molecule of this invention include powders, sprays, ointments, pastes, creams, lotions, gels, solutions, patches and inhalants. In one embodiment, the active duplex RNA molecule is mixed under sterile conditions with a pharmaceutically acceptable carrier, and with any preservatives, buffers, or propellants that are required.

The present invention provides a method of treatment comprising administering an effective amount of the pharmaceutical composition to a subject in need. In an embodiment, the pharmaceutical composition is administered via a route selected from the group consisting of iv, sc, topical, po, and ip. In another embodiment, the effective amount is 1 ng to 1 g per day, 100 ng to 1 g per day, or 1 µg to 1 mg per day.

The present invention also provides pharmaceutical formulations comprising a duplex RNA molecule of the present invention in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active duplex RNA molecule, use thereof in the compositions is contemplated. Supplementary active duplex RNA molecules can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A duplex RNA molecule of the present invention is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a duplex RNA molecule of the present invention (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a duplex RNA molecule of the present invention is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active duplex RNA molecules of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active duplex RNA molecules into preparations that can be used pharmaceutically. Of course, the appropriate formulation is dependent upon the route of administration chosen.

A duplex RNA molecule or pharmaceutical composition of the invention can be administered to a subject in many of the well-known methods currently used for chemotherapeutic treatment. For example, for treatment of cancers, a duplex RNA molecule of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not as high as to cause unacceptable side effects. The state of the disease condition (e.g., cancer, psoriasis, and the like) and the health of the patient should be closely monitored during and for a reasonable period after treatment.

EXAMPLES

Examples are provided below to further illustrate different features of the present invention. The examples also illustrate useful methodology for practicing the invention. These examples do not limit the claimed invention.

RNA interference (RNAi) is a catalytic mechanism of gene-specific silencing in eukaryotic organisms with profound implications for biology and medicine (Fire et al., 1998), 12. RNAi is mediated by the RNA-induced silencing complex (RISC) (Hammond et al., 2000; Martinez and Tuschl, 2004; Rana, 2007) upon incorporating with small interfering RNAs (siRNA) of 19-21 base pairs (bp) with 3' overhangs, the smallest RNA duplex known to enter RISC and mediate RNAi (Elbashir et al., 2001a; Elbashir et al., 2001b; Elbashir et al., 2001c; Fire et al., 1998; Zamore et al., 2000). As the natural substrate of the RISC enzyme complex, siRNA can be chemically synthesized or generated through Dicer-catalyzed processing of its various precursors (Donze and Picard, 2002; Hammond et al., 2000; Kim et al., 2005; Paddison et al., 2002). While being used widely for gene silencing, siRNA has limited efficiency in gene silencing with low silencing efficacy for numerous genes in mammalian cells (de Fougerolles et al., 2007; Iorns et al., 2007). Here we investigate structural scaffold requirements for an efficient RNAi mediator in mammalian cells. To our surprise, we found that asymmetric RNA duplexes of 14-15 bp with dual antisense overhangs mediate potent and efficacious gene silencing in mammalian cells. The asymmetric interfering RNA (aiRNA), structurally characterized by duplex RNA of 14-15 by with 3' and 5' antisense overhangs, was incorporated into RISC with higher efficiency than siRNA. The aiRNA caused sequence-specific cleavage of the mRNA and targeted gene silencing in mammalian cells. When the identical sequence of β-catenin mRNA was targeted, the aiRNA was more efficacious (near 100%), potent (picoM), rapid-onset (less than 24 h) and durable (up to 1 week) than siRNA in mediating gene silencing in vitro. These results suggest aiRNA as the smallest RNA duplex scaffold incorporated into RISC and non-siRNA type of RNAi mediators that silence genes with better efficiency than siRNA in mammalian cells. Therefore, aiRNA may have significant potential for broad RNAi application.

Methods and Materials

Cell Culture and Reagents

Hela, SW480, DLD1, HT29, and H1299 cells were obtained from ATCC, and cultured in Dulbecco's modified Eagle's medium (DMEM) containing 10% fetal bovine serum (FBS), 100 units/ml penicillin, 100 μg/ml streptomycin and 2 mM L-glutamine (Invitrogen). Fresh peripheral blood mononuclear cells (PBMC) were obtained from AllCells LLC and maintained in RPMI-1640 medium containing 10% FBS and pen/strep (Invitrogen). Small RNAs described in this study were synthesized by Dharmacon, Qiagen, or Integrated DNA technologies (Table 2) and annealed following the manufacturer's instructions (FIG. 3a). siRNAs targeting human Ago2, and Dicer (Ambion) were used at 100 nM. Transfections of the RNAs were performed using DharmaFECT1 (Dharmacon) at the indicated concentrations. Human Argonaute2 (Ago2) expression vector (OriGene) was transfected using Lipofectamine 2000 (Invitrogen). Serum stability was determined by incubation of aiRNA or siRNA duplex with 10% human serum (Sigma) for the indicated amount of time followed by non-denaturing TBE-acrylamide gel electrophoresis and ethidium bromide staining.

Northern Blot Analysis.

To determine levels of β-catenin, total RNA was extracted with TRIZOL (Invitrogen) from siRNA or aiRNA transfected Hela cells at various time points. 20 μg of total cellular RNA was loaded to each lane of a denaturing agarose gel. After electrophoresis, RNA was transferred to Hybond-XL Nylon membrane (Amersham Biosciences), UV crosslinked, and baked at 80° C. for 30 min. Probes detecting β-catenin and actin mRNA was prepared using Prime-It II Random Primer Labeling Kit (Stratagene) from β-catenin cDNA fragment (1-568 nt) and actin cDNA fragment (1-500 nt). To analyze small RNA RISC loading, siRNA or aiRNA were transfected into Hela cells 48 hours after transfection with pCMV-Ago2. Cells were lysed at the indicated timepoints and immunoprecipitated with Ago2 antibody. Immunoprecipitates were washed, RNA isolated from the complex by TRIZOL extraction, and loaded on a 15% TBE-Urea PAGE gel (Bio-Rad). Following electrophoreses, RNA was transferred to Hybond-XL Nylon membrane. mirVana miRNA Probe Kit (Ambion) was used to generate 5' $^{32}$P labeled RNA probes. Antisense probe (5'-GUAGCUGAUAUUGAUGGACUU-3' (SEQ ID NO:71)). Sense probe (5'-UCCAUCAAUAUCAGC-3' (SEQ ID NO:72))

In Vitro Ago2-RISC Loading.

aiRNA or siRNA sense and anti-sense strands were $^{32}$P end labeled using T4 kinase (Promega). End labeled RNAs were purified by phenol/chloroform/isoamyl alcohol, precipitated with EtOH, and resuspended in water. Labeled RNAs were then annealed to siRNA or aiRNA anti-sense strands as described. For in vitro lysates, Hela cells were transfected for 24 hours with human Ago2 expression vector, and S10 lysates generated essentially as described (Dignam et al., 1983). 5' sense strand or anti-sense strand labeled duplex aiRNA or siRNA was then added to the Ago2-S10 lysate. Following a 5 min incubation at 37° C., Ago2 was immunoprecipitated as described, and Ago2-associated (pellet) and non-Ago2 associated (supernatant) fractions were separated on a 20% TBE-acrylamide gel and gel exposed to film to detect sense strand-Ago2 association. For aiRNA and siRNA competition experiments, up to 100 folds cold aiRNA and siRNA were used to compete with $^{32}$P labeled aiRNA or siRNA to load to RISC. Briefly, S10 lysates were generated from Hela cells transfected with Ago2 expression vector as described. Labeled aiRNA or siRNA was then added to the S10 lysates followed immediately by addition of unlabeled aiRNA or siRNA. Reaction was incubated for 5 min at 37° C. and processed as described above.

qRT-PCR.

Cells transfected with the indicated aiRNA or siRNA were harvested at the indicated time points following transfection. RNA was isolated with TRIZOL, and qRT-PCR performed using TaqMan one-step RT-PCR reagents and primer probe sets for the indicated mRNA (Applied Biosystems). Data is presented relative to control transfected cells and each sample is normalized to actin mRNA levels. For the experiment in FIG. 14d, Stat3 constructs were created by cloning Stat3 cDNA (Origene) into either pcDNA3.1$^+$ or pcDNA3.1$^-$ at the HindIII-Xho1 sites. Stat3 forward or reverse expression vectors were then co-transfected into Hela cells with aiStat3 or siStat3 for 24 hours. Cells were then harvested, RNA isolated by TRIZOL, and qRT-PCR performed using TaqMan one-step RT-PCR reagents and primer probe sets for Stat3 or actin (Applied Biosystems). RT-PCR was performed on the same RNA samples using Superscript One-Step RT-PCR kit (Invitrogen) and Stat3 forward (5'-GGATCTAGAATCAGCTACAGCAGC-3' (SEQ ID NO:73)) and Stat3 reverse (5% TCCTCTA-GAGGGCAATCTCCATTG-3' (SEQ ID NO:74)) primers and actin forward (5'-CCATGGATGATGATATCGCC-3' (SEQ ID NO:75)) and actin reverse (5% TAGAAGCATTT-GCGGTGGAC-3' (SEQ ID NO:76)) primers.

RT-PCR.

Total RNA was prepared using the TRIZOL, and cDNA was synthesized using random primers with Thermoscript RT-PCR System (Invitrogen). PCR was run for 20 cycles using Pfx polymerase. Primers: ACTIN-1, 5' CCATGGAT-GATGATATCGCC-3' (SEQ ID NO:75); ACTIN-2, 5'-TAGAAGCATTTGCGGTGGAC-3' (SEQ ID NO:76); β-catenin-0.1, 5'-GACAATGGCTACTCAAGCTG-3'(SEQ ID NO:77); β-catenin-2, 5'-CAGGTCAGTATCAAAC-CAGG-3' (SEQ ID NO:78).

Western Blot.

Cells were washed twice with ice-cold phosphate-buffered saline and lysed in lysis buffer (50 mM HEPES, pH 7.5, 0.5% Nonidet P-40, 150 mM NaCl, 1 mM EDTA, 1 mM EGTA, 1 mM sodium orthovanadate, 1 mM dithiothreitol, 1 mM NaF, 2 mM phenylmethylsulfonyl fluoride, and 10 µg/ml each of pepstatin, leupeptin, and aprotinin). 20 µg of soluble protein was separated by SDS-PAGE and transferred to PVDF membranes. Primary Antibodies against β-catenin, Nbs1, Survivin, p21, Rsk1, k-Ras, Stat3, PCNA, NQO1, Actin (Santa Cruz), EF2, p70S6K, mTOR, PTEN (Cell Signaling Technology), Ago2 (Wako), Dicer (Novas), and Parp1 (EMD Biosciences) were used in this study. The antigen-antibody complexes were visualized by enhanced chemiluminescence (GE Biosciences).

5'-RACE Analysis

Total RNA (5 µg) from Hela cells treated with non-silencing aiRNA or aiRNA was ligated to GeneRacer™ RNA adaptor (Invitrogen, 5'-CGACUGGAGCACGAGGA-CACUGACAUGGACUGAAGGAGUAGAAA-3' (SEQ ID NO:79)) without any prior processing. Ligated RNA was reverse transcribed into cDNA using a random primer. To detect cleavage product, PCR was performed using primers complementary to the RNA adaptor (GeneRace™ 5' Nested Primer: 5'-GGACACTGACATGGACTGAAGGAGTA-3' (SEQ ID NO:80)) and β-catenin specific primer (GSP: 5'-CGCATGATAGCGTGTCTGGAAGCTT-3' (SEQ ID NO:81)). Amplification fragments were resolved on 1.4% agarose gel and sized using a 1-kb Plus DNA Ladder (Invitrogen). Specific cleavage site was further confirmed by DNA sequencing.

Interferon-Response Detection.

Figure 15A:
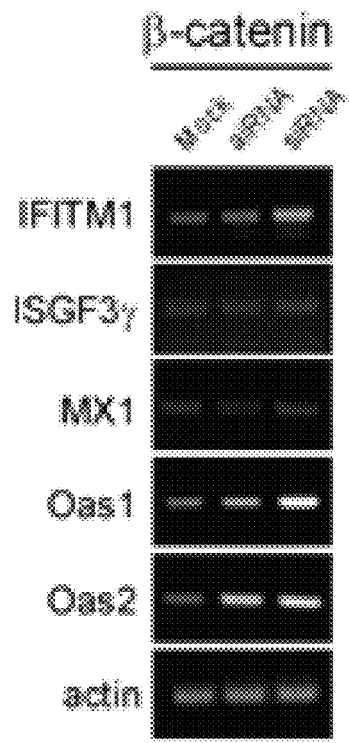

For the experiment in FIG. 15a, PBMC were incubated directly with 100 nM β-catenin siRNA or aiRNA. Total RNA was purified at 16 hours using TRIZOL, and levels of interferon responsive gene expression were determined by RT-PCR as described by the manufacturer (System Biosciences). For the experiment in FIG. 15b, Hela cells were mock transfected or transfected with 100 nM of the indicated aiRNA or siRNA for 24 hours. Total RNA was purified using TRIZOL and levels of interferon responsive gene expression were determined by RT-PCR. For microarray analysis, Hela cells were transfected with 100 nM aiRNA or siRNA. Total RNA was purified at 24 hours using TRIZOL, and RNA was used for hybridization to Human Genome U133 Plus 2.0 GeneChip (Affymetrix) according to the manufacturer's protocol (ExpressionAnalysis, Inc.). RNA from DharmaFECT 1 treated cells was used as control. To calculate transcript expression values, Microarray Suite 5.0 was used with quantile normalization, and transcripts with sufficient hybridization signals to be called present (P) were used in this study.

aiRNA and siRNA Sequences

Sequence and structure of aiRNA and siRNA duplexes were listed in Table 2. Location of point mutation is framed in the k-Ras aiRNA.

TABLE 2 siβ-catenin    G U A G C U G A U A U U G A U G G A C U U    SEQ ID NO: 117
               | | | | | | | | | | | | | | | | | | |
               | | | | | | | | | | | | | | | | | | |
               U U C A U C G A C U A U A A C U A C C U G    SEQ ID NO: 118

TABLE 2-continued

| Name | Sequence | SEQ ID NO |
|---|---|---|
| aiβ-catenin | G C U G A U A U U G A U G G A | SEQ ID NO: 119 |
| | C A U C G A C U A U A A C U A C C U G A A | SEQ ID NO: 120 |
| siNbs1 | A U C A U G C U G U G U U A A C U G C U U | SEQ ID NO: 121 |
| | U U U A G U A C G A C A C A A U U G A C G | SEQ ID NO: 122 |
| aiNbs1 | A U G C U G U G U U A A C U G | SEQ ID NO: 123 |
| | U A G U A C G A C A C A A U U G A C G A A | SEQ ID NO: 124 |
| siEF2 | G G C C C U C U U A U G A U G U A U A U U | SEQ ID NO: 125 |
| | U U C C G G G A G A A U A C U A C A U A U | SEQ ID NO: 126 |
| aiEF2 | C C U C U U A U G A U G U A U | SEQ ID NO: 127 |
| | C C G G G A G A A U A C U A C A U A U A A | SEQ ID NO: 128 |
| siStat3 | G C C A G C A A A G A A U C A C A U G U U | SEQ ID NO: 129 |
| | U U C G G U C G U U U C U U A G U G U A C | SEQ ID NO: 130 |
| aiStat3 | A G C A A A G A A U C A C A U | SEQ ID NO: 131 |
| | C G G U C G U U U C U U A G U G U A C A A | SEQ ID NO: 132 |
| siPTEN | A G C U A A A G G U G A A G A U A U A U U | SEQ ID NO: 133 |
| | U U U C G A U U U C C A C U U C U A U A U | SEQ ID NO: 134 |
| aiPTEN | U A A A G G U G A A G A U A U | SEQ ID NO: 135 |
| | U C G A U U U C C A C U U C U A U A U A A | SEQ ID NO: 136 |
| sip70S6K | C C G U G U U U G A U U U G G A U U U U U | SEQ ID NO: 137 |
| | U U G G C A C A A A C U A A A C C U A A A | SEQ ID NO: 138 |
| aip70S6K | U G U U U G A U U U G G A U U | SEQ ID NO: 139 |
| | G G C A C A A A C U A A A C C U A A A A A | SEQ ID NO: 140 |
| simTOR | G C A G A A U U G U C A A G G G A U A U U | SEQ ID NO: 141 |
| | U U C G U C U U A A C A G U U C C C U A U | SEQ ID NO: 142 |
| aimTOR | G A A U U G U C A A G G G A U | SEQ ID NO: 143 |
| | C G U C U U A A C A G U U C C C U A U A A | SEQ ID NO: 144 |
| siRsk1 | G G A A A U U G G A A C A C A G U U U U U | SEQ ID NO: 145 |
| | U U C C U U U A A C C U U G U G U C A A A | SEQ ID NO: 146 |
| aiRsk1 | A A U U G G A A C A C A G U U | SEQ ID NO: 147 |
| | C C U U U A A C C U U G U G U C A A A A A | SEQ ID NO: 148 |
| siPCNA | U G G A G A U G C U G U U G U A A U U U U | SEQ ID NO: 149 |
| | U U A C C U C U A C G A C A A C A U U A A | SEQ ID NO: 150 |

TABLE 2-continued

| Name | Sense (top) / Antisense (bottom) | SEQ ID NO |
|---|---|---|
| aiPCNA | A G A U G C U G U U G U A A U | 151 |
| | A C C U C U A C G A C A A C A U U A A A A | 152 |
| siParp1 | G U G G C G A A G A A G A A A U C U A U U | 153 |
| | U U C A C C G C U U C U U C U U U A G A U | 154 |
| aiParp1 | G C G A A G A A G A A A U C U | 155 |
| | C A C C G C U U C U U C U U U A G A U A A | 156 |
| siSurvivin | A A G G A G A U C A A C A U U U U C A dTdT | 157 |
| | dTDT U U C C U C U A G U U G U A A A A G U | 158 |
| aiSurvivin | A G G A G A U C A A C A U U U | 159 |
| | dTdT U U C C U C U A G U U G U A A A A G U | 160 |
| siNQO1 | G C C G C A G A C C U U G U G A U A U dTdT | 161 |
| | dTdT C G G C G U C U G G A A C A C U A U A | 162 |
| aiNQO1 | G C A G A C C U U G U G A U A | 163 |
| | C G G C G U C U G G A A C A C U A U A A A | 164 |
| sip21 | A G G C C C G C U C U A C A U C U U C U U | 165 |
| | U U U C C G G G C G A G A U G U A G A A G | 166 |
| aip21 | C C C G C U C U A C A U C U U | 167 |
| | U C C G G G C G A G A U G U A G A A G A A | 168 |
| aik-Ras | G G A G C U G [U] U G G C G U A | 169 |
| | C A A C C U C G A C [A] C C G C A U C A A | 170 |

In Life Evaluations

Daily examinations into the health status of each animal were also conducted. Body weights were checked every three days. Food and water was supplied daily according to the animal husbandry procedures of the facility. Treatment producing >20% lethality and or >20% net body weight loss were considered toxic. Results are expressed as mean tumor volume (mm$^3$)±SE. P Values <0.05 are considered to be statistically relevant.

Animal Husbandry

Male or female athymic nude mice 4-5 weeks (Charles River Laboratories, Wilmington, Mass.), were acclimated to the animal housing facility for at least 1 week before study initiation. All of the experimental procedures utilized were consistent with the guidelines outlined by the American Physiology Society and the Guide for the Care and Use of Laboratory Animals and were also approved by the Institutional Animal Care and Use Committee of Boston Biomedical Inc. The animals were housed in groups of four in wood chip bedded cages in a room having controlled temperature (68° F.-72° F.), light (12-h light-dark cycle), and humidity (45-55%). The animals were allowed free access to water and food during the experiment.

Example 1. Asymmetric Interfering RNA (aiRNA) Causes Gene-Specific Silencing in Mammalian Cells The siRNA structural scaffold is considered the essential configuration for incorporating into RISC and mediating RNAi (Elbashir et al., 2001a; Elbashir et al., 2001 b; Elbashir et al., 2001c; Rana, 2007; Zamore et al., 2000). However, very little is known about RNA duplex scaffold requirements for RISC incorporation and gene silencing. To investigate the structural scaffold requirements for an efficient RNAi mediator and RISC substrate, we first determined if RNA duplexes shorter than siRNAs could mediate gene silencing. The length of double stranded (ds) RNA is an important determinant of its propensity in activating protein kinase R (PKR)-mediated non-specific interferon responses, increased synthesis cost, and delivery challenges (Elbashir et al., 2001b; Sledz et al., 2003). We designed a series of short dsRNAs ranging from 12 to 21 bp with 2 nucleotide 3' overhangs or blunt ends targeting different mammalian genes. No gene silencing was detected after the length was reduced below 19 bp (data not shown), which is consistent with previous reports in *Drosophila Melanogaster* cell lysate (Elbashir et al., 2001b) and the notion that 19-21 bp is the shortest siRNA duplex that mediates RNAi (Elbashir et al., 2001a; Elbashir et al., 2001b; Elbashir et al., 2001c; Rana, 2007; Zamore et al., 2000).

We next tested if RNA duplexes of non-siRNA scaffold with an asymmetric configuration of overhangs can mediate gene silencing. The siRNA duplex contains a symmetrical sense strand and an antisense strand. While the duplex siRNA structure containing a 3' overhang is required for incorporation into the RISC complex, following Argonaute (Ago) mediated cleavage of the sense strand, the antisense strand directs cleavage of the target mRNA (Hammond et al., 2001; Matranga et al., 2005; Tabara et al., 1999). We sought to make asymmetric RNA duplexes of various lengths with overhangs at the 3' and 5' ends of the antisense strand.

Figure 3A:
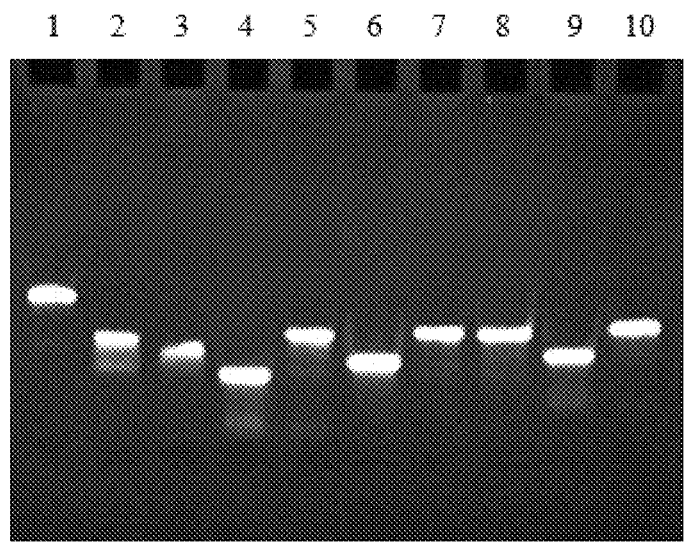
FIG. 3 shows the induction of gene silencing of β-catenin by aiRNA (asymmetric interfering RNAs). (A) shows the confirmation of the oligos. After annealing, the oligos were confirmed by 20% polyacrylamide gel. Lane 1, 21 nt/21 nt; lane 2, 12 nt (a)/21 nt; lane 3, 12 nt (b)/21 nt; lane 4, 13 nt/13 nt; lane 5, 13 nt/21 nt; lane 6, 14 nt/14 nt; lane 7, 14 nt(a)/21 nt; lane 8, 14 nt(b)/21 nt; lane 9, 15 nt/15 nt; lane 10, 15 nt/21 nt. (B) shows the effects of the oligos in gene silencing. HeLa cells were plated at 200,000 cells/well into a 6 well culture plate. 24 hours later they were transfected with scramble siRNA (lane 1), 21-bp siRNA targeted E2F1 (lane 2, as a control for specificity) or 21-bp siRNA targeted beta-catenin (lane 3, as a positive control), or the same concentration of aiRNA of different length mix: 12 nt(a)/21 nt (lane 4); 12 nt (b)/21 nt (lane 5); 13 nt/21 nt (lane 6); 14 nt (a)/21 nt (lane 7); 14 nt (b)/21 nt (lane 8); 15 nt/21 nt (lane 9). Cells were harvested 48 hours after transfection. Expression of β-catenin was determined by Western blot. E2F1 and actin are used as controls.

Oligos with sequences shown in Table 3 were confirmed by 20% polyacrylamide gel after annealing. As shown in FIG. 3A, each lane was loaded as follows: lane 1, 21 nt/21 nt; lane 2, 12 nt (a)/21 nt; lane 3, 12 nt (b)/21 nt; lane 4, 13 nt/13 nt; lane 5, 13 nt/21 nt; lane 6, 14 nt/14 nt; lane 7, 14 nt(a)/21 nt; lane 8, 14 nt(b)/21 nt; lane 9, 15 nt/15 nt; lane 10, 15 nt/21 nt.

TABLE 3

| Oligos | Sequences |
|---|---|
| 21 nt/21 nt | 5'-GUAGCUGAUAUUGAUGGACTT-3' (SEQ ID NO: 82)<br>3'-TTCAUCGACUAUAACUACCUG-5' (SEQ ID NO: 83) |
| 12nt/21nt (a) | 5'-UGAUAUUGAUGG-3' (SEQ ID NO: 84)<br>3'-CAUCGACUAUAACUACCUGAA-5' (SEQ ID NO: 39) |
| 12nt/21nt (b) | 5'-CUGAUAUUGAUG-3' (SEQ ID NO: 85)<br>3'-CAUCGACUAUAACUACCUGAA-5' (SEQ ID NO: 39) |
| 13nt/21nt | 5'-CUGAUAUUGAUGG-3' (SEQ ID NO: 86)<br>3'-CAUCGACUAUAACUACCUGAA-5' (SEQ ID NO: 39) |
| 14nt/21nt (a) | 5'-GCUGAUAUUGAUGG-3' (SEQ ID NO: 87)<br>3'-CAUCGACUAUAACUACCUGAA-5' (SEQ ID NO: 39) |
| 14nt/21nt (b) | 5'-CUGAUAUUGAUGGA-3' (SEQ ID NO: 88)<br>3'-CAUCGACUAUAACUACCUGAA-5' (SEQ ID NO: 39) |
| 15nt/21nt | 5'-GCUGAUAUUGAUGGA-3' (SEQ ID NO: 34)<br>3'-CAUCGACUAUAACUACCUGAA-5' (SEQ ID NO: 39) |

Figure 3B:
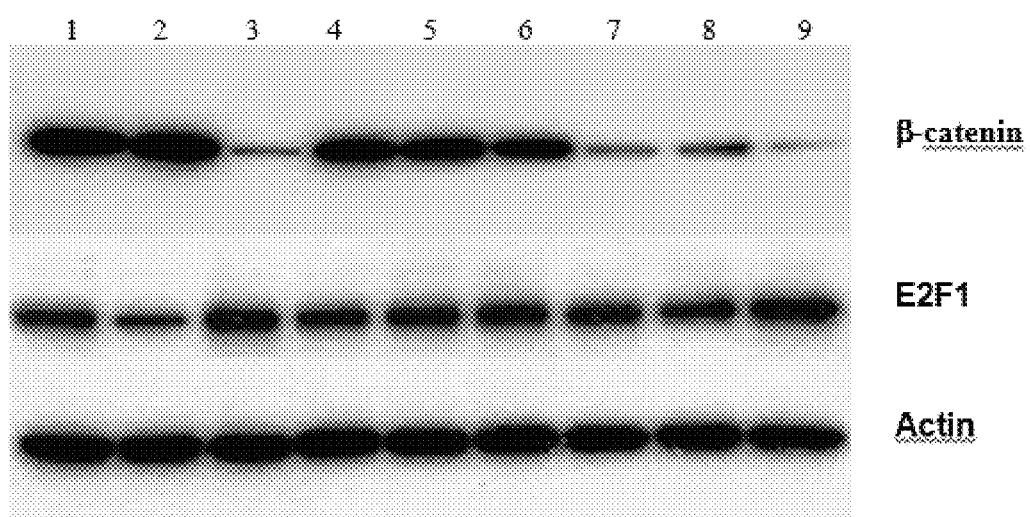

HeLa cells were plated at 200,000 cells/well into a 6 well culture plate. As shown in FIG. 3B, 24 hours later they were transfected with scramble siRNA (lane 1), 21-bp siRNA targeted E2F1 (lane 2, as a control for specificity) or 21-bp siRNA targeted beta-catenin (lane 3, as a positive control), or the same concentration of aiRNA of different length mix: 12 nt(a)/21 nt (lane 4); 12 nt (b)/21 nt (lane 5); 13 nt/21 nt (lane 6); 14 nt (a)/21 nt (lane 7); 14 nt (b)/21 nt (lane 8); 15 nt/21 nt (lane 9). Cells were harvested 48 hours after transfection. Expression of β-catenin was determined by Western blot. E2F1 and actin are used as controls. The results demonstrate that asymmetric interfering RNA (aiRNA) causes gene-specific silencing in mammalian cells.

In order to determine the structural features of aiRNA important in aiRNA function, we generated multiple aiRNA oligonucleotides based on modification of the core 15/21 dual anti-sense overhang structure (Table 4). The aiRNAs, summarized in Table 4, contained modifications including, but not limited to, length of the sense and anti-sense strands, degree of sense and anti-sense overhangs, and RNA-DNA hybrid oligonucleotides.

Modification to the parental 15/21 aiRNA structure was done by altering the sense strand, anti-sense strand, or both (Table 4). Modified aiRNA duplexes were transfected into Hela cells at 50 nM for 48 hours. Western blots for β-catenin and actin were used to examine the degree of gene silencing compared to the parental 15/21 aiRNA and to the traditional siRNA structure. aiRNA modifications were also tested which contained dual sense strand overhangs. These oligonucleotides contain a 21 base sense strand paired to differing length anti-sense strands. In addition, we also examined the activity of aiRNA oligonucleotides that have been modified with DNA bases. DNA substitutions were done on both the anti-sense and sense strands (Table 3). RNA-DNA hybrid oligonucleotides tested contained 1 or more DNA substitutions in either the sense or anti-sense strand, or contained 21 base anti-sense RNA paired with indicated length of DNA sense strand. The gene silencing results of these various aiRNAs were shown in FIGS. 4 and 5.

Taken together, these data provide structural clues to aiRNA function.

Regarding the sense strand, our data indicate that the length of 15 bases works well, while lengths between 14 and 19 bases remain functional. The sense strand can match any part of the anti-sense strand, provided that the anti-sense overhang rules are met. Replacement of a single RNA base with DNA at either the 5' or 3' end of the sense strand is tolerated and may even provide increased activity.

With respect to the anti-sense strand length, the length of 21 bases works well, 19-22 bases retains activity, and activity is decreased when the length falls below 19 bases or increases above 22 bases. The 3' end of the anti-sense strand requires an overhang of 1-5 bases with a 2-3 base overhang being preferred, blunt end shows a decrease in activity. Base pairing with the target RNA sequence is preferred, and DNA base replacement up to 3 bases is tolerated without concurrent 5' DNA base replacement. The 5' end of the anti-sense strand prefers a 0-4 base overhang, and does not require an overhang to remain active. The 5' end of the anti-sense strand can tolerate 2 bases not matching the target RNA sequence, and can tolerate DNA base replacement up to 3 bases without concurrent 3' DNA base replacement.

With respect to mismatched or chemically modified bases, we find that both mismatches and one or more chemically modified bases in either the sense or anti-sense strand is tolerated by the aiRNA structure.

Figure 4:
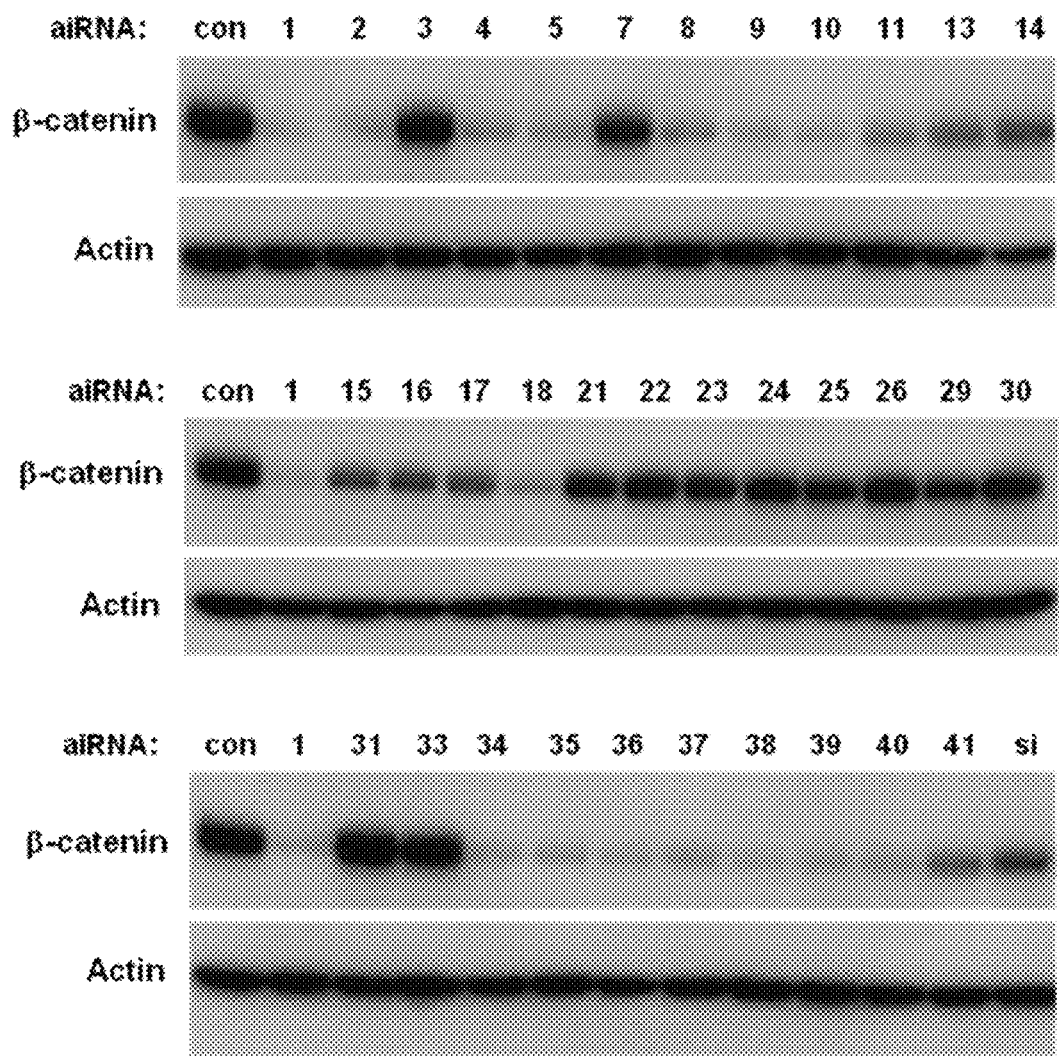
FIG. 4: shows the structure-activity relationship of aiRNA oligos, with or without base substitutions, in mediating gene silencing. Hela cells were transfected with the indicated aiRNA. Cells were harvested and lysates generated at 48 hours post transfection. Western blots were performed to detect levels of β-catenin and actin. si stands for β-catenin siRNA oligonucleotide. The numerical labeling above each lane corresponds to the aiRNA oligos in Table 3.
Figure 5:
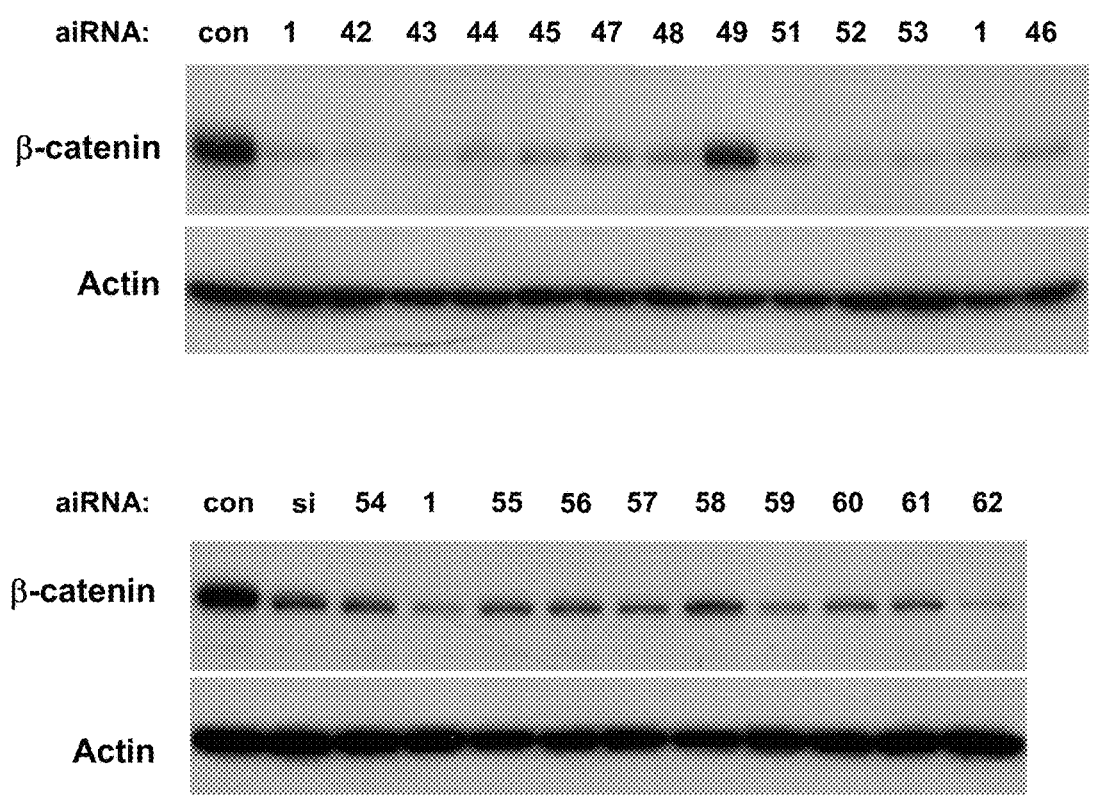
FIG. 5: shows the structure-activity relationship of aiRNA oligos, with or without base substitutions, in mediating gene silencing. Hela cells were transfected with the indicated aiRNA. Cells were harvested and lysates generated at 48 hours post transfection. Western blots were performed to detect levels of β-catenin and actin. si stands for β-catenin siRNA oligonucleotide. The numerical labeling above each lane corresponds to the aiRNA oligos in Table 3.

TABLE 4 aiRNA sequences used for figures 4-5

| aiRNA # | Generic Structure | Sequence |
|---|---|---|
| 1 | 15-21 (NNN--NNN) | 5'-GCUGAUAUUGAUGGA (SEQ ID NO: 34)<br>CAUCGACUAUAACUACCUGAA-5' (SEQ ID NO: 39) |
| 2 | 15-21a (NNNNNN---blunt) | 5'-GAUAUUGAUGGACUU (SEQ ID NO: 36)<br>CAUCGACUAUAACUACCUGAA-5' (SEQ ID NO: 39) |
| 3 | 15-21b (blunt---NNNNNN) | 5'-GUAGCUGAUAUUGAU (SEQ ID NO: 89)<br>CAUCGACUAUAACUACCUGAA-5' (SEQ ID NO: 39) |
| 4 | 15-21c (NNNN---NN) | 5'-CUGAUAUUGAUGGAC (SEQ ID NO: 38)<br>CAUCGACUAUAACUACCUGAA-5' (SEQ ID NO: 39) |
| 5 | 15-21d (NN---NNNN) | 5'-AGCUGAUAUUGAUGG (SEQ ID NO: 40)<br>CAUCGACUAUAACUACCUGAA-5' (SEQ ID NO: 39) |
| 7 | 15-18b (blunt cut 3'---NNN) | 5'-GCUGAUAUUGAUGGA (SEQ ID NO: 34)<br>CGACUAUAACUACCUGAA-5' (SEQ ID NO: 90) |
| 8 | 15-21d (N---NNNNN) | 5'-UAGCUGAUAUUGAUG (SEQ ID NO: 41)<br>CAUCGACUAUAACUACCUGAA-5' (SEQ ID NO: 39) |
| 9 | 15-21c (NNNNN---N) | 5'-UGAUAUUGAUGGACU (SEQ ID NO: 42)<br>CAUCGACUAUAACUACCUGAA-5' (SEQ ID NO: 39) |
| 10 | 15-22a (NNNN---NNN) | 5'-GCUGAUAUUGAUGGA (SEQ ID NO: 34)<br>UCAUCGACUAUAACUACCUGAA-5' (SEQ ID NO: 43) |
| 11 | 15-22b (NNN---NNNN) | 5'-GCUGAUAUUGAUGGA (SEQ ID NO: 34)<br>CAUCGACUAUAACUACCUGAAA-5' (SEQ ID NO: 35) |
| 13 | 15-24a (NNNNN---NNNN) | -GCUGAUAUUGAUGGA (SEQ ID NO: 34)<br>UUCAUCGACUAUAACUACCUGUAA-5' (SEQ ID NO: 91) |
| 14 | 15-24b (NNNN---NNNNN) | 5'-GCUGAUAUUGAUGGA (SEQ ID NO: 34)<br>UCAUCGACUAUAACUACCUGUCAA-5' (SEQ ID NO: 92) |
| 15 | 15-27(WW101--NNNNNN) | 5'-GCUGAUAUUGAUGGA (SEQ ID NO: 34)<br>GUUCAUCGACUAUAACUACCUGUCAUA-5' (SEQ ID NO: 93) |
| 16 | 15-20a (NNN---NN) | 5'-GCUGAUAUUGAUGGA (SEQ ID NO: 34)<br>CAUCGACUAUAACUACCUGA-5' (SEQ ID NO: 94) |
| 17 | 15-20b (NNNN---N) | 5'-GCUGAUAUUGAUGGA (SEQ ID NO: 34)<br>UCAUCGACUAUAACUACCUG-5' (SEQ ID NO: 95) |
| 18 | 15-20c (NN---NNN) | 5'-GCUGAUAUUGAUGGA (SEQ ID NO: 34)<br>AUCGACUAUAACUACCUGAA-5' (SEQ ID NO: 37) |
| 21 | 15-190 (01101-bluM) | 5'-GCUGAUAUUGAUGGA (SEQ ID NO: 34)<br>UCAUCGACUAUAACUACCU-5' (SEQ ID NO: 96) |
| 22 | 15-18a (NN---N) | 5'-GCUGAUAUUGAUGGA (SEQ ID NO: 34)<br>AUCGACUAUAACUACCUG-5' (SEQ ID NO: 97) |
| 23 | 15-18b (NNN-blunt) | 5'-GCUGAUAUUGAUGGA (SEQ ID NO: 34)<br>CAUCGACUAUAACUACCU-5 (SEQ ID NO: 98) |
| 24 | 15-18e (blunt---NNN) | 5'-GCUGAUAUUGAUGGA (SEQ ID NO: 34)<br>CGACUAUAACUACCUGAA-5' (SEQ ID NO: 90) |
| 25 | 15-17a (NN---blunt) | 5'-GCUGAUAUUGAUGGA (SEQ ID NO: 34)<br>AUCGACUAUAACUACCU-5' (SEQ ID NO: 99) |
| 26 | 15-17b (blunt---NN) | 5 -GCUGAUAUUGAUGGA (SEQ ID NO: 34)<br>CGACUAUAACUACCUGA-5' (SEQ ID NO: 100) |
| 29 | 14-20 (NNN---NNN) | 5'-GCUGAUAUUGAUGG (SEQ ID NO: 87)<br>CAUCGACUAUAACUACCUGA-5' (SEQ ID NO: 94) |
| 30 | 14-19a (NNN---NN) | 5'-GCUGAUAUUGAUGG (SEQ ID NO: 87)<br>CAUCGACUAUAACUACCUG-5' (SEQ ID NO: 101) |
| 31 | 14-19b (NN---NNN) | 5'-GCUGAUAUUGAUGG (SEQ ID NO: 87)<br>AUCGACUAUAACUACCUGA-5' (SEQ ID NO: 102) |

TABLE 4-continued aiRNA sequences used for figures 4-5

| aiRNA # | Generic Structure | Sequence |
|---|---|---|
| 33 | 14-18b (NNN--N) | 5'-GCUGAUAUUGAUGG (SEQ ID NO: 87)<br>CAUCGACUAUAACUACCU-5' (SEQ ID NO: 98) |
| 34 | 16-21a (NNN--NN) | 5'-GCUGAUAUUGAUGGAC (SEQ ID NO: 44)<br>CAUCGACUAUAACUACCUGAA-5' (SEQ ID NO: 39) |
| 35 | 16-21b (NN--NNN) | 5'-AGCUGAUAUUGAUGGA (SEQ ID NO: 45)<br>CAUCGACUAUAACUACCUGAA-' (SEQ ID NO: 39) |
| 36 | 17-21 (NN---NN) | 5'-AGCUGAUAUUGAUGGAC (SEQ ID NO: 46)<br>CAUCGACUAUAACUACCUGAA-5' (SEQ ID NO: 39) |
| 37 | 18-21a(NN---N) | 5'-AGCUGAUAUUGAUGGACU (SEQ ID NO: 47)<br>CAUCGACUAUAACUACCUGAA-5' (SEQ ID NO: 39) |
| 38 | 18-21b (N---NN) | 5'-UAGCUGAUAUUGAUGGAC (SEQ ID NO: 48)<br>CAUCGACUAUAACUACCUGAA-5' (SEQ ID NO: 39) |
| 39 | 18-21c (NNN---blunt) | 5'-GCUGAUAUUGAUGGACUU (SEQ ID NO: 49)<br>CAUCGACUAUAACUACCUGAA-5' (SEQ ID NO: 39) |
| 40 | 19-21a (NN---blunt) | 5'-AGCUGAUAUUGAUGGACUU (SEQ ID NO: 50)<br>CAUCGACUAUAACUACCUGA-5' (SEQ ID NO: 39) |
| 41 | 18-21b (blunt---NNN) | 5'-GUAGCUGAUAUUGAUGGA (SEQ ID NO: 103)<br>CAUCGUCUAUAACUACCUGA-5' (SEQ ID NO: 104) |
| 42 | 19-21c(N--N) | 5'-UAGCUGAUAUUGAUGGACU (SEQ ID NO: 51)<br>CAUCGACUAUAACUACCUGAA-5' (SEQ ID NO: 39) |
| 43 | 20-21a (N--blunt) | 5'-UAGCUGAUAUUGAUGGACUU (SEQ ID NO: 52)<br>CAUCGACUAUAACUACCUGAA-5' (SEQ ID NO: 39) |
| 44 | 20-21b (blunt---N) | 5'-GUAGCUGAUAUUGAUGGACU (SEQ ID NO: 53)<br>CAUCGACUAUAACUACCUGAA-5' (SEQ ID NO: 39) |
| 45 | Mismatch and miRNA | 5'-GCUGAUAUUGAAGGA (SEQ ID NO: 54)<br>CAUCGACUAUAACUACCUGAA-5' (SEQ ID NO: 39) |
| 46 | 5' end homologous to target | 5'-GCUGAUAUUGAUGGA (SEQ ID NO: 34)<br>CAUCGACUAUAACUACCUGUC-5' (SEQ ID NO: 55) |
| 47 | NNNNNNNNNNNNNNN (SEQ ID NO: 108)<br>3'NNNNNNNNNNNNNNNNNNNDDD-5' (SEQ ID NO: 108) | 5'-GCUGAUAUUGAUGGA (SEQ ID NO: 34)<br>CAUCGACUAUAACUACCUgaa-5' (SEQ ID NO: 56) |
| 48 | NNNNNNNNNNNNNNN (SEQ ID NO: 108)<br>3'DDDNNNNNNNNNNNNNNNNNNN-5' | 5'-GCUGAUAUUGAUGGA (SEQ ID NO: 34)<br>catCGACUAUAACUACCUGAA-5' (SEQ ID NO: 57) |
| 49 | NNNNNNNNNNNNNNN (SEQ ID NO: 108)<br>3'DDDNNNNNNNNNNNNNNNNDDD-5' (SEQ ID NO: 110) | 5'-GCUGAUAUUGAUGGA (SEQ ID NO: 34)<br>caCGACUAUAACUACCUgaa-5' (SEQ ID NO: 105) |
| 51 | DNDNNNNNNNDNDND (SEQ ID NO: 116)<br>3'NNNNNNNNNNNNNNNNNNNNN-5' (SEQ ID NO: 111) | 5'-gCtGAUAUUGaUgGa (SEQ ID NO: 106)<br>CAUCGACUAUAACUACCUGAA-5' (SEQ ID NO: 39) |
| 52 | DNNNNNNNNNNNNNN (SEQ ID NO: 114)<br>3'NNNNNNNNNNNNNNNNNNNNN-5' (SEQ ID NO: 111) | 5'-gCUGAUAUUGAUGGA (SEQ ID NO: 58)<br>CAUCGACUAUAACUACCUGAA-5' (SEQ ID NO: 39) |
| 53 | NNNNNNNNNNNNNND (SEQ ID NO: 115)<br>3'NNNNNNNNNNNNNNNNNNNNN-5' (SEQ ID NO: 113) | 5'-GCUGAUAUUGAUGGa (SEQ ID NO: 59)<br>CAUCGACUAUAACUACCUGAA-5' (SEQ ID NO: 39) |
| 54 |  | 5'-UAGCUGAUAUUGAUG (SEQ ID NO: 41)<br>UUCAUCGACUAUAACUACCUG-5' (SEQ ID NO: 107) |

TABLE 4-continued aiRNA sequences used for figures 4-5

| aiRNA # | Generic Structure | Sequence |
|---|---|---|
| 55 | | 5'-GUAGCUGAUAUUGAUGGA (SEQ ID NO: 103)<br>UUCAUCGACUAUAACUACCUG-5' (SEQ ID NO: 107) |
| 56 | | 5'-AGCUGAUAUUGAUGGA (SEQ ID NO: 45)<br>UUCAUCGACUAUAACUACCUG-5' (SEQ ID NO: 107) |
| 57 | DNNNNNNNNNNNNNN (SEQ ID NO: 114)<br>3'DDDNNNNNNNNNNNNNNNNNNN-5' (SEQ ID NO: 112) | 5'-gCUGAUAUUGAUGGA (SEQ ID NO: 58)<br>caCGACUAUAACUACCUGAA-5' (SEQ ID NO: 57) |
| 58 | DNNNNNNNNNNNNNN (SEQ ID NO: 114)<br>3'NNNNNNNNNNNNNNNNNNDDD-5' (SEQ ID NO: 109) | 5'-gCUGAUAUUGAUGGA (SEQ ID NO: 58)<br>CAUCGACUAUAACUACCUGaa-5' (SEQ ID NO: 56) |
| 59 | NNNNNNNNNNNNNND (SEQ ID NO: 115)<br>3'DDDNNNNNNNNNNNNNNNNNNN-5' (SEQ ID NO: 112) | 5'-GCUGAUAUUGAUGGa (SEQ ID NO: 59)<br>caCGACUAUAACUACCUGAA-5' (SEQ ID NO: 57) |
| 60 | NNNNNNNNNNNNNND (SEQ ID NO: 115)<br>3'DDDNNNNNNNNNNNNNNNNNNN-5' (SEQ ID NO: 109) | 5'-GCUGAUAUUGAUGGa (SEQ ID NO: 59)<br>CAUCGACUAUAACUACCUGAA-5' (SEQ ID NO: 56) |
| 61 | NNNNNNNNNNNNNNNNNN (SEQ ID NO: 111)<br>3'DDDNNNNNNNNNNNNNNNNNNN-5 (SEQ ID NO: 112) | 5'-UAGCUGAUAUUGAUGGACU (SEQ ID NO: 51)<br>caCGACUAUAACUACCUGAA-5' (SEQ ID NO: 57) |
| 62 | NNNNNNNNNNNNNNNNNN (SEQ ID NO: 111)<br>3'DDDNNNNNNNNNNNNNNNNNNN-5' (SEQ ID NO: 109) | 5'-UAGCUGAUAUUGAUGGACU (SEQ ID NO: 51)<br>CAUCGACUAUAACUACCUGaa-5' (SEQ ID NO: 56) |

In table 4, A, U, G, C represent nucleotides, while a, t, g, c represent deoxynucleotides.

Example 2. Mechanism of Gene Silencing Triggered by aiRNA

Figure 6A:
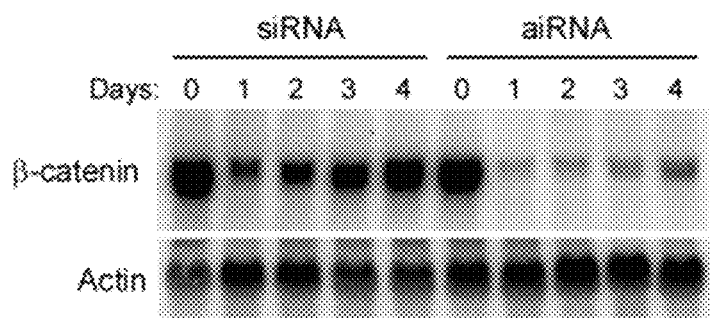
FIG. 6 shows the analysis of the mechanism of gene silencing triggered by aiRNA. (A) shows the northern blot analysis of β-catenin mRNA levels in cells transfected with aiRNA or siRNA for the indicated number of days. (B) shows the schematic of 5'-RACE-PCR for β-catenin showing cleavage of mRNA and expected PCR product. (C) shows β-catenin cleavage products mediated by aiRNA were amplified by 5'-RACE-PCR from cells transfected with aiRNA for 4 or 8 hours. (D) shows the schematic of β-catenin mRNA cleavage site confirmed by sequencing the 5'-RACE-PCR fragment (SEQ ID NOs:34 and 39). (E) shows differential RISC loading efficiency of aiRNA and siRNA. aiRNA or siRNA duplexes were transfected into Hela cells 48 hours after transfection with pCMV-Ago2. Ago2 was immunoprecipitated at the indicated time points following aiRNA or siRNA transfection, and northern blot analysis was performed to determine levels of Ago2/RISC associated small RNAs. Levels of Ago2 (shown below) were determined by western blot following IP. (F) shows the effects of knocking down Ago2 or Dicer on gene silencing activity of aiRNA and siRNA. Cells were transfected with scramble siRNA (siCon), or siRNA targeting Ago2 (siAgo2), or Dicer (siDicer) 24 hours prior to transfection with scramble aiRNA (Con) or aiRNA targeting Stat3 (ai). Cells were harvested and western blot analysis was performed at 48 hours following aiStat3 transfection.
Figure 6B:
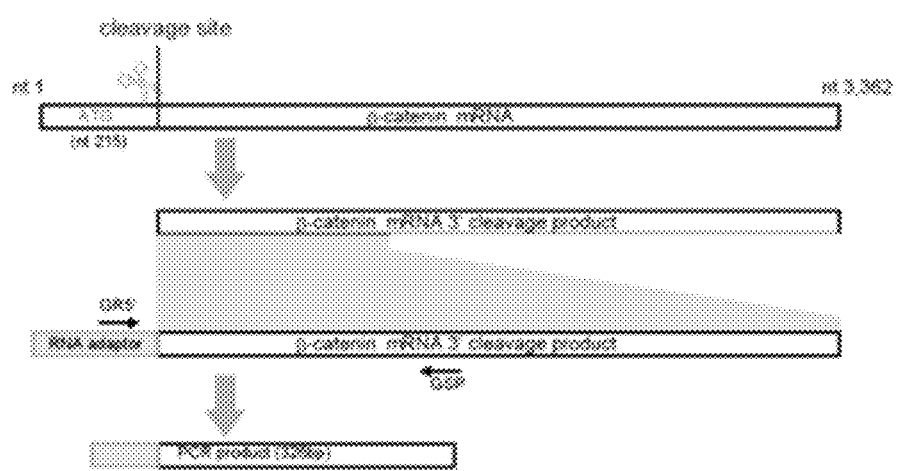
Figure 6C:
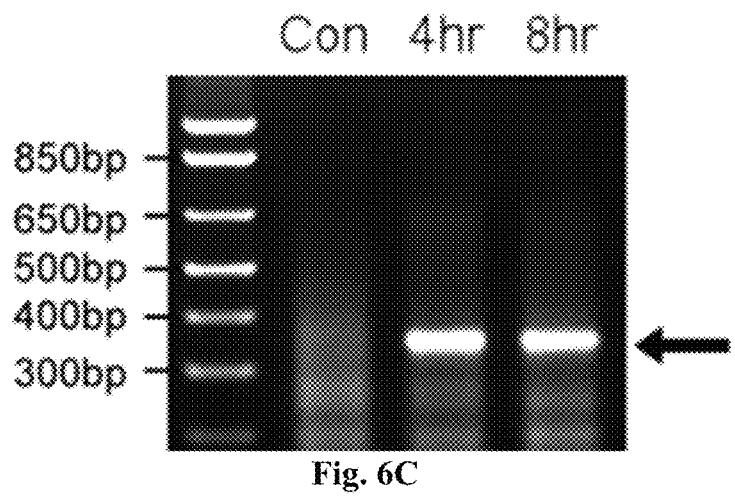
Figure 6D:
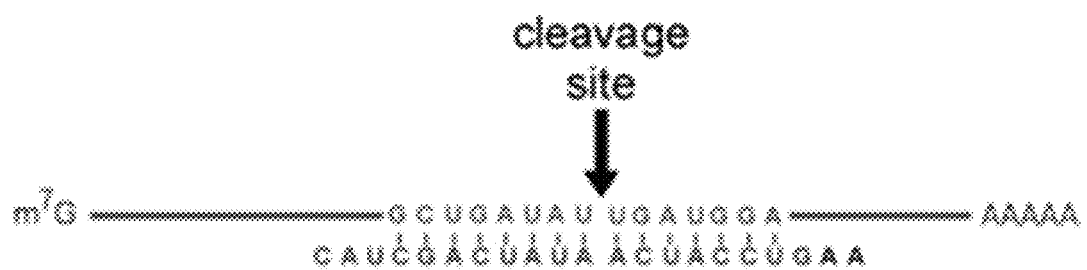

To investigated the mechanism of gene knockdown induced by aiRNA, we first determined if the gene silencing by aiRNA occurs at translational or mRNA level. Northern blot analysis of β-catenin in cells transfected with 10 nM of the 15 bp aiRNA showed that the aiRNA reduced mRNA levels by over 95% within 24 hours and the decrease lasted more than 4 days (FIG. 6a), suggesting that aiRNA mediates gene silencing at the mRNA level. The reduction of β-catenin mRNA induced by aiRNA was substantially more rapid, efficacious and durable than by siRNA (FIG. 6a). We further determined if the 15 bp aiRNA catalyzed the site-specific cleavage of β-catenin mRNA. Total RNA isolated from cells transfected with the 15 bp aiRNA was examined by rapid amplification of cDNA ends (5'-RACE) and PCR for the presence of the β-catenin mRNA cleavage fragments (FIG. 6b). We detected β-catenin cleavage fragments at 4 and 8 hours following aiRNA transfection (FIG. 6c). Sequence analysis showed that cleavage was taking place within the aiRNA target sequence between bases 10 and 11 relative to the 5' end of the aiRNA antisense strand (FIG. 6d). No such cleavage fragments were observed following transfection with a scrambled aiRNA (FIG. 6c). These results demonstrate that aiRNA induced potent and efficacious gene silencing through sequence-specific cleavage of the target mRNA.

Figure 6E:
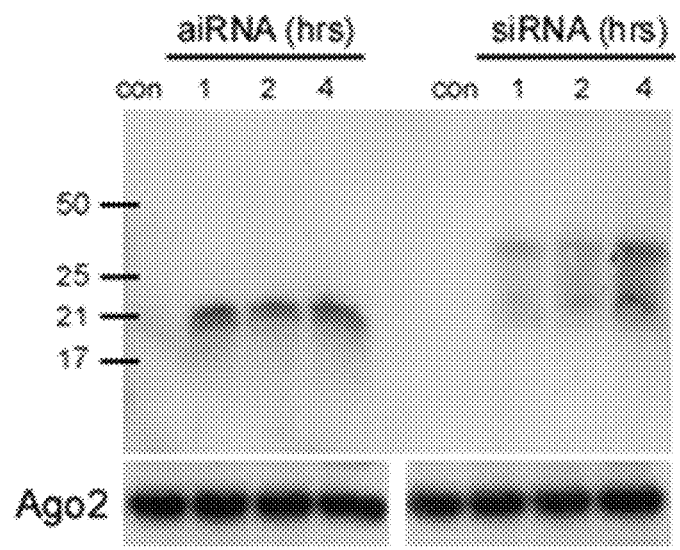
Figure 6F:
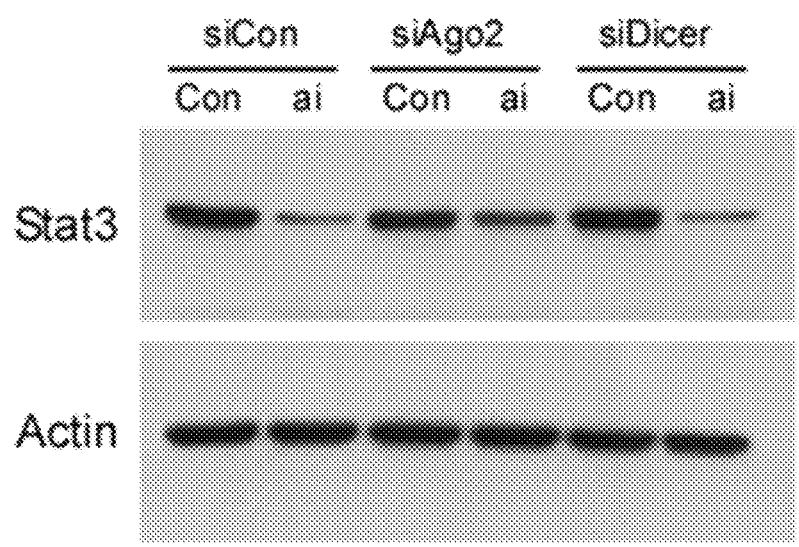

We next determined whether the novel asymmetric scaffold of aiRNA can be incorporated into the RISC. RNAi is catalyzed by RISC enzyme complex with an Argonaute protein (Ago) as the catalytic unit of the complex (Liu et al., 2004; Matranga et al., 2005). To determine if aiRNA is incorporated into the Ago/RISC complex, we immunoprecipitated myc-tagged human Ago1 from cells expressing myc-tagged Ago1 (Siolas et al., 2005) after cells were transfected with aiRNA. Small RNAs associated with the RISC complex were detected by northern blotting of Ago immunoprecipitates. Northern blot analysis revealed that the aiRNA entered the RISC complex with high efficiency (FIG. 6e). These data suggest the asymmetric scaffold of aiRNA can be efficiently incorporated into RISC.

Figure 7A:
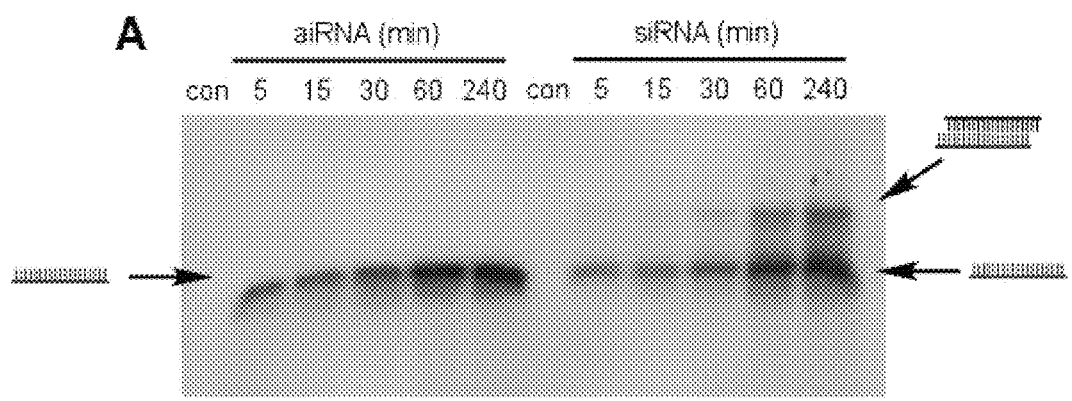
FIG. 7 shows the advantages of incorporation of aiRNA into RISC compared to siRNA. (A) shows that aiRNA enters RISC with better efficiency than siRNA. Cells transfected with Ago2 expression plasmid were transfected with aiRNA or siRNA for the indicated times. Following cell lysis, Ago2 was immunoprecipitated, RNA extracted from the immunoprecipitate, and separated on a 15% acrylamide gel. Following transfer, the membrane was hybridized to a probe to detect the 21 mer antisense strand of the aiRNA or siRNA. IgG control lane shows lack of signal compared to Ago2 immunoprecipitate. (B) shows that the sense strand of aiRNA does not stay in RISC. Membrane from (A) was stripped and re-probed to detect the sense strand of the transfected oligo. Cartoons in (A) and (B) illustrate the position of the sense strand (upper strand), the antisense strand (lower strand), or the duplex on the membrane.

Since aiRNA induced more efficient gene silencing than siRNA, we tested if aiRNA can give rise to RISC complex more efficiently than siRNA. As shown in FIG. 6e, aiRNA-Ago2/RISC complexes formed faster and more efficient than the siRNA-Ago2/RISC complexes, with more aiRNA contained in the RISC complex than the corresponding siRNA (FIG. 6e and FIG. 7A). Of note, siRNA displayed a typical pattern (21) that is consistent with formation of secondary structures by siRNA (FIG. 6e and FIG. 7). In contrast, aiRNA displayed a single band, suggesting that the shorter length of aiRNA may reduce or eliminate the secondary structure formation as occurred with siRNA.

Figure 7B:
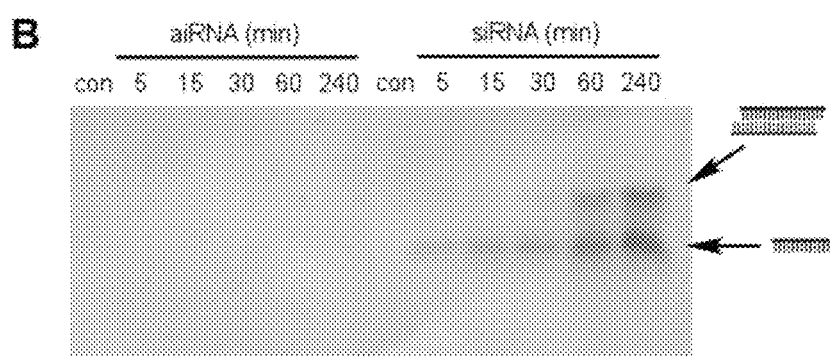
Figure 8A:
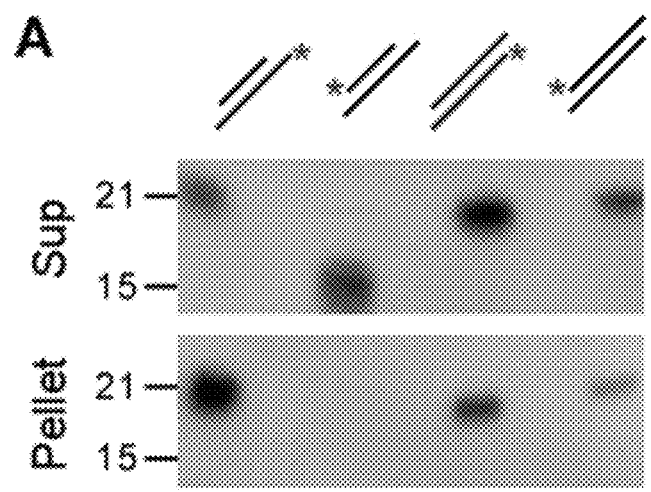
FIG. 8 shows that the mechanism of RISC loading by aiRNA. (A) shows the immunoprecipitation analysis of the interaction between different strands of aiRNA or siRNA and Ago2. Hela S-10 lysate containing overexpressed Ago2 was incubated with the indicated aiRNA or siRNA duplex containing $^{32}$P end labeled sense or antisense strands. The (*) marks the location of the label. Following Ago2 immunoprecipitation, the RNA was isolated and separated on a 15% acrylamide gel and exposed to film. The Ago2-associated RNAs are shown in the pellet fraction, while the non-Ago2 bound RNAs remain in the supernatant (Sup). (B) shows the role of sense strand cleavage in aiRNA activity.

Further, the asymmetric configuration of aiRNA may facilitate the formation of active RISC with antisense strand and reduce the ineffective RISC formed with the sense strand (Ref. 16). Our data proved this is true as shown in FIG. 7B, no sense strand can be detected in the RISC complex. FIG. 8A also demonstrates that while the antisense strand of the aiRNA strongly associates with Ago 2, the sense-strand does not. In contrast, both the anti-sense and sense strand of the siRNA associate with Ago 2. These data suggest that aiRNA has higher efficiency in forming RISC than siRNA in cells, which may underlie the superior gene silencing efficiency of aiRNA.

Figure 8B:
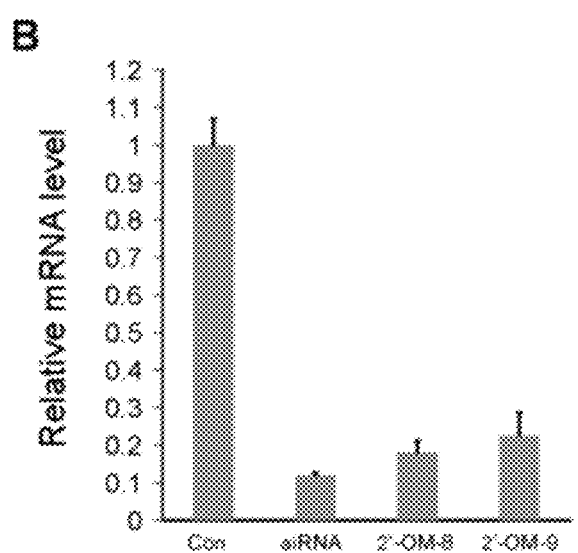

In addition, it has been shown that the sense strand of siRNA is required to be cleaved in order to be functional. Therefore, we tested if the same requirement is true for aiRNA. To do that, the nucleotide at position 8 or 9 of the aiRNA sense strand was modified with 2'-O-methyl to make it uncleavable. Our results show that the aiRNAs with the uncleavable sense strand are still functional (FIG. 8B), demonstrating aiRNA is quite different than siRNA in terms of their mechanism.

Figure 9B:
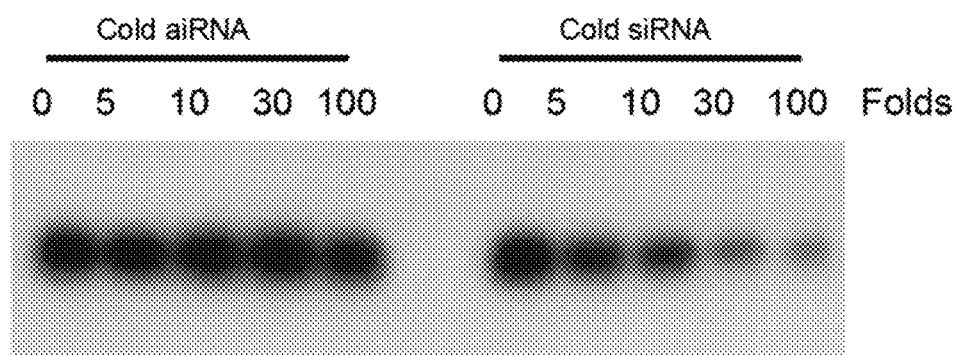
Figure 9C:
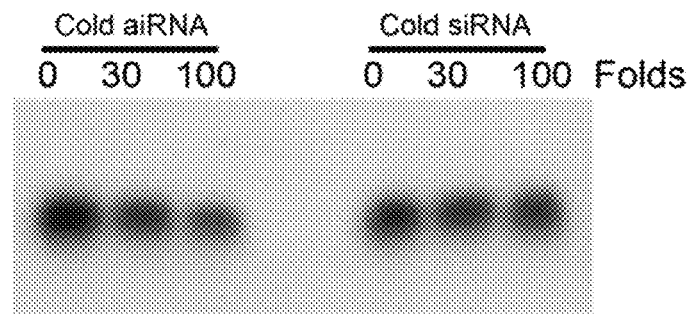

Further we asked if there is any different loading pocket for aiRNA and siRNA. We used cold aiRNA or siRNA to compete with the radioactively labelled siRNA or aiRNA for the RISC complex (FIG. 9). Surprisingly, the results show that cold aiRNA does not compete with the siRNA for RISC complex (FIG. 9B) and cold siRNA does not compete with aiRNA for the RISC complex either (FIG. 9C). These data indicate that aiRNA and siRNA may load to different pockets of RISC complex.

Together, the data above suggest that aiRNA represents the first non-siRNA scaffold that is incorporated into RISC, providing a novel structural scaffold that interacts with RISC. The difference of the RISC loading of aiRNA and siRNA is illustrated in our model shown in FIG. 10. Briefly, because of the asymmetric property, only the anti-sense strand is selected to stay in the RISC complex and results in a 100% efficiency in strand selection. In contrast, siRNA is structurally symmetric. Both anti-sense strand and sense strand of the siRNA has a chance to be selected to stay in the RISC complex and therefore siRNA has an inefficient strand selection and at the same time may cause non-specific gene silencing due to the sense strand RISC complex.

Example 3. aiRNA Mediates a More Rapid, Potent, Efficacious, and Durable Gene Silencing than siRNA To compare aiRNA with siRNA in gene silencing properties, we first determined the optimal aiRNA structure for gene silencing.

Figure 11A:
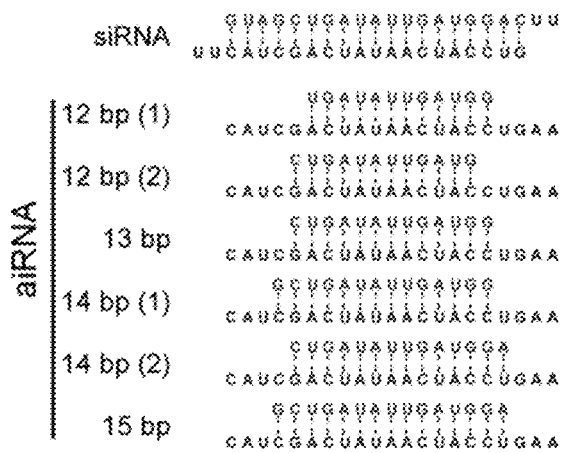
Figure 11B:
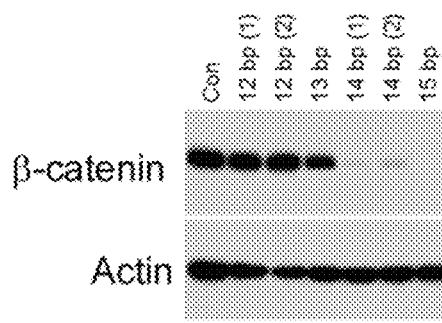

The siRNA duplex contains a symmetrical sense strand and an antisense strand. While the duplex siRNA structure containing a 3' overhang is required for incorporation into the RISC complex, following Argonaute (Ago) mediated cleavage of the sense strand, the antisense strand directs cleavage of the target mRNA (Hammond et al., 2001; Matranga et al., 2005; Tabara et al., 1999). We sought to make asymmetric RNA duplexes of various lengths with overhangs at the 3' and 5' ends of the antisense strand. We designed one set of such asymmetrical RNA duplexes of 12 to 15 bp with 3' and 5' antisense overhangs to target β-catenin (FIG. 11A), an endogenous gene implicated in cancer and stem cells (Clevers, 2006). An optimized siRNA of the standard configuration has been designed to target β-catenin for triggering RNAi (Xiang et al., 2006). All aiRNAs against β-catenin were designed within the same sequence targeted by the siRNA (FIG. 11A). The results showed that the optimal gene silencing achieved was with the 15 bp aiRNA (FIG. 11B). Therefore, we used 15 bp aiRNA to be compared with 21-mer siRNA duplex in the subsequent experiments.

Figure 11C:
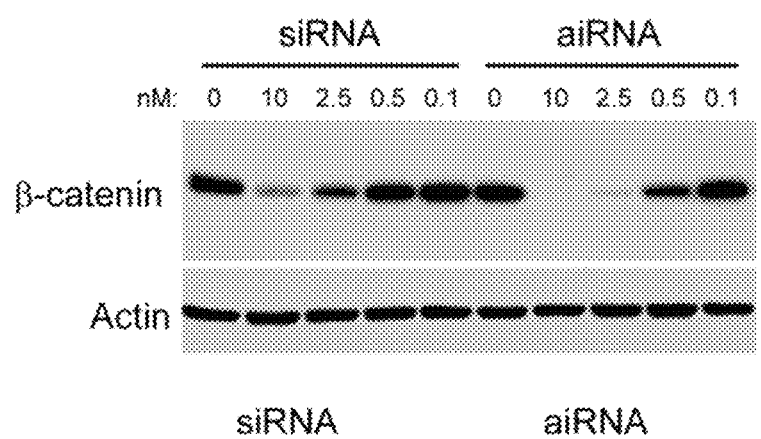
Figure 11D:
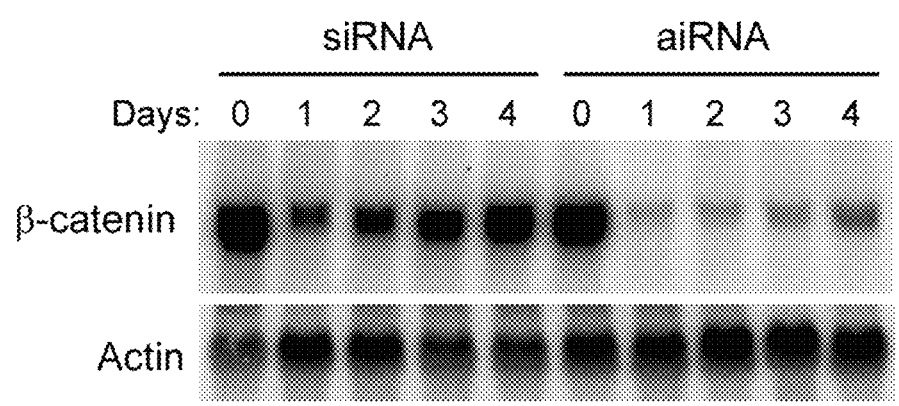

To our surprise, we found that aiRNA induced potent and highly efficacious reduction of β-catenin protein while sparing the non-targeted control genes actin (FIG. 11C).

Figures 12A, 12B:
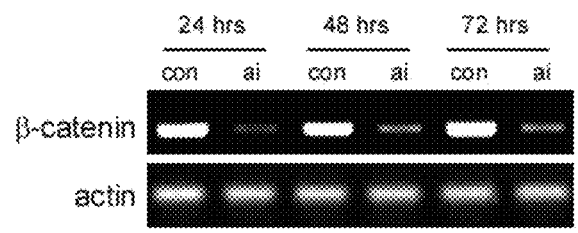
Figure 12C:
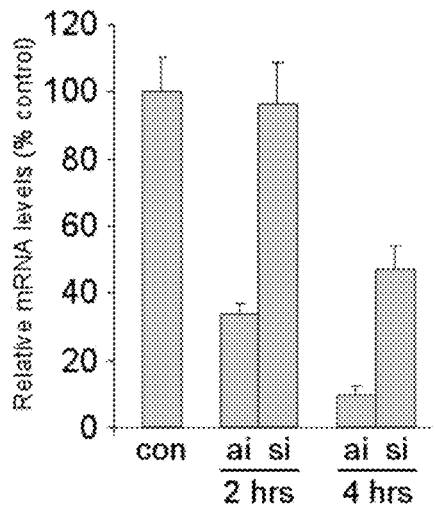
Figure 12D:
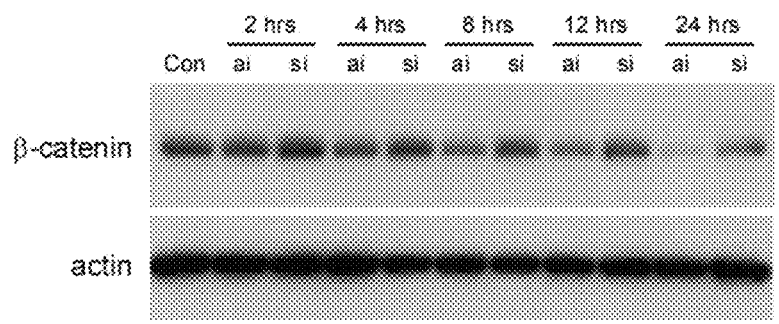

We next examined the onset of gene silencing by aiRNA and siRNA targeting β-catenin. The sequence of the aiRNA and siRNA used is shown in FIG. 11A. As shown in FIG. 12, aiRNA has a more rapid onset (FIGS. 12C and D) and also a better efficacy (FIGS. 12B and D).

Figure 14A:
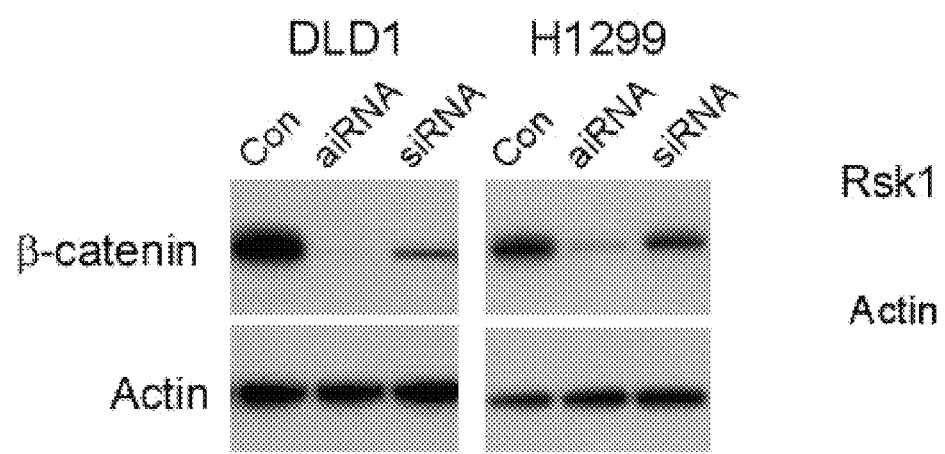
Figure 14B:
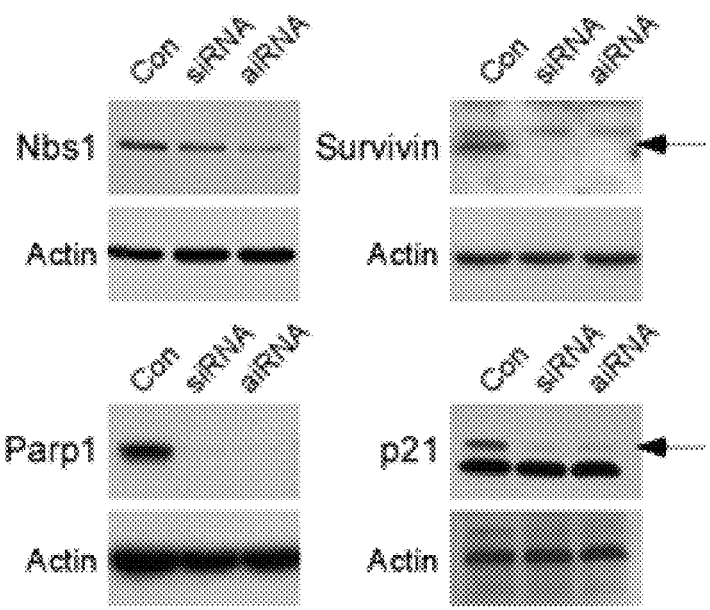
Figure 14C:
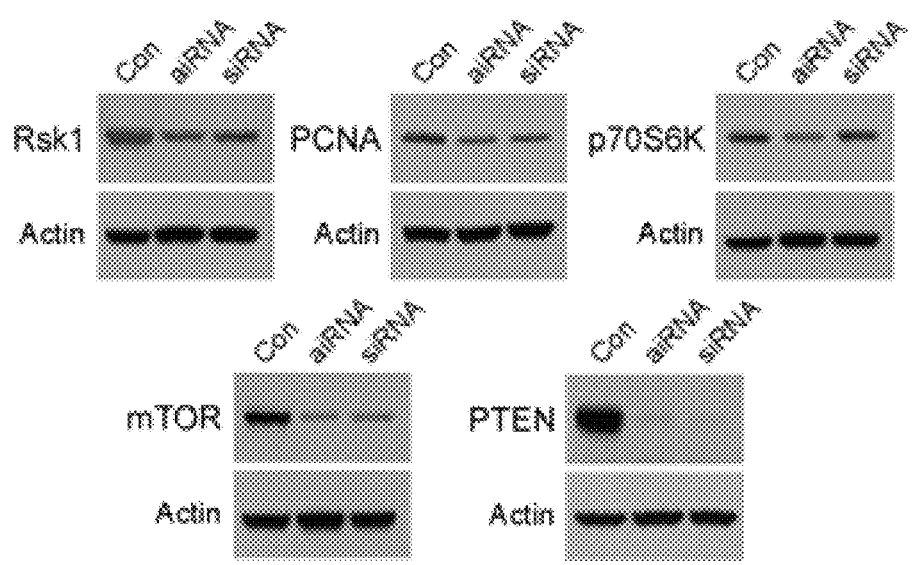

We also compared the gene silencing effects of aiRNA and siRNA on various targets and multiple human cell lines. The aiRNAs were designed to target genes of different functional categories including Stat3 (FIG. 13b), NQO1 (FIG. 12d), elongation factor 2 (EF2) (FIG. 13c), Nbs1 (FIG. 14b), Survivin (FIG. 14b), Parp1 (FIG. 14b), p21 (FIG. 14b), Rsk1 (FIG. 14c), PCNA (FIG. 14c), p70S6K (FIG. 14c), mTOR (FIG. 14c), and PTEN (FIG. 14c), besides β-catenin (FIG. 13a) at the same sequences that have been targeted with siRNA with low efficiency (Rogoff et al., 2004). As shown in FIGS. 13 and 14, aiRNA is more efficacious than siRNA in silencing Stat3, β-catenin, Rsk1, p70S6K, Nbs1, mTOR, and EF2, and is as efficacious as siRNA in silencing NQO1, PCNA, Survivin, PTEN, Parp1, and p21. Since the target sequences were chosen based on the optimization for siRNA, it is possible that the efficacy and potency of aiRNA can be further increased by targeting sites that are optimized for aiRNA. In addition, our data also shows that aiRNA is more efficacious than siRNA against b-catenin in multiple cell lines including Hela (FIG. 13a), H1299 (FIG. 14a, left panel) and Dld1 (FIG. 14a, right panel).

Taken together, these data demonstrate that aiRNA is more efficacious, potent, rapid-onset, and durable than siRNA in mediating gene silencing in mammalian cells.

Example 4. Specificity of Gene Silencing Mediated by aiRNA

Figure 14D:
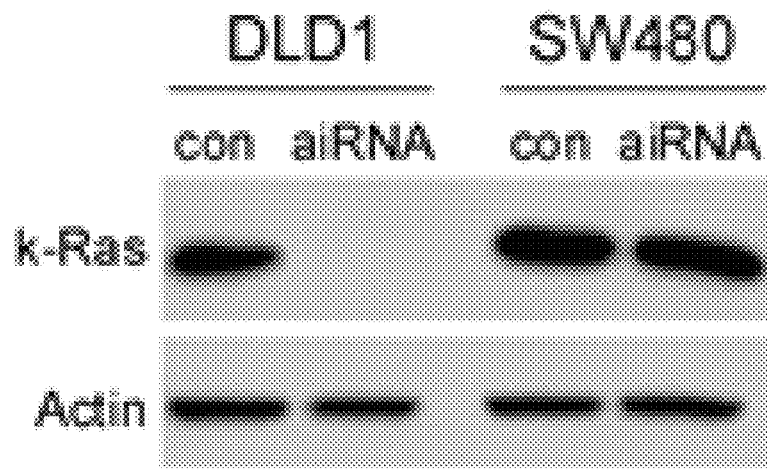

We next investigated the specificity of gene silencing mediated by aiRNAs. We first analyzed aiRNAs that target the wildtype k-Ras allele. DLD1 cells contain wild-type k-Ras while SW480 cells contain mutant k-Ras that has a single base pair substitution (FIG. 14d). Transfection of DLD1 cells with aiRNA targeting wildtype k-Ras showed effective silencing, but no silencing of mutant k-Ras was observed in the SW480 cells. These data demonstrate that aiRNA mediates allele specific gene silencing.

Figures 15B, 15C:
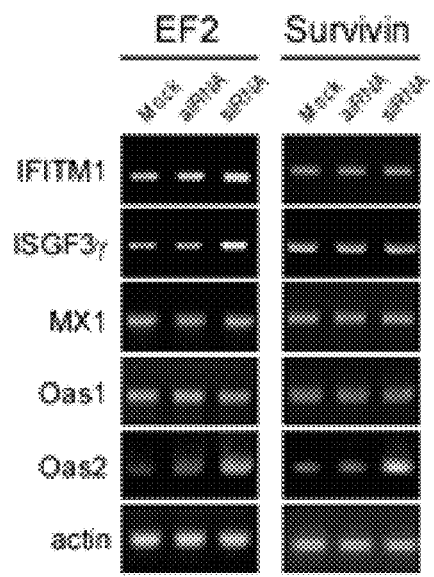

The activation of an interferon-like response is a major non-specific mechanism of gene silencing. A primary reason that siRNAs are used for gene silencing is that the dsRNA of shorter than 30 bp has reduced ability to activate the interferon-like response in mammalian cells (Bernstein et al., 2001; Martinez and Tuschl, 2004; Sledz et al., 2003). We tested if aiRNA showed any signs of activating the interferon-like response in mammalian cells. RNA collected from PBMC cells transfected with aiRNA against β-catenin and Hela cells transfected with aiRNA against EF2 or Survivin was analyzed by RT-PCR for interferon inducible genes. We found that aiRNA transfection showed no increase by RT-PCR of any of the interferon inducible genes tested, while levels of targeted mRNAs were reduced relative to control transfected cells (FIGS. 15a and b). Microarray analysis was also performed to compare the changes in the expression of known interferon response related genes induced by aiRNA and miRNA. As shown in FIG. 15c, much less changes were observed for aiRNA compared to siRNA.

Figure 15D:
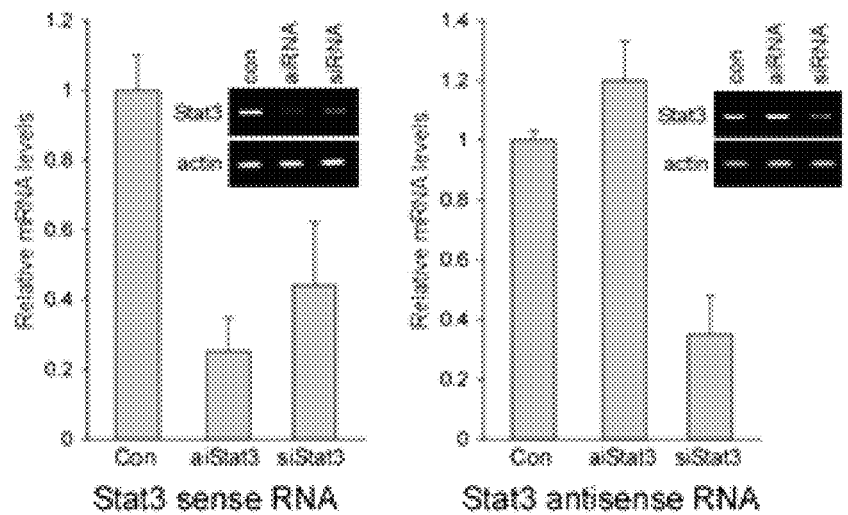
Figure 15E:
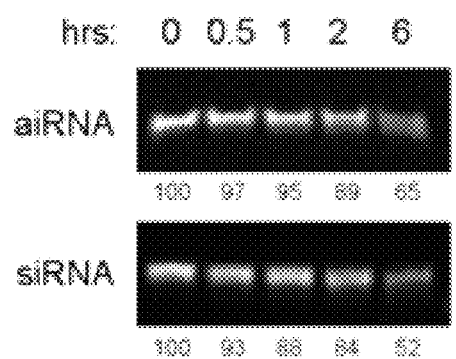

In addition, as mentioned above, sense strand-RISC complex may cause non-specific gene silencing. To compare aiRNA and siRNA on the non-specific gene silencing mediated by sense-strand-RISC complex, cells were co-transfected with aiRNA or siRNA and either a plasmid expressing Stat3 (sense RNA) or a plasmid expressing antisense Stat3 (antisense RNA). Cells were harvested and RNA collected at 24 hours post transfection and relative levels of Stat3 sense or antisense RNA were determined by quantitative real time PCR or RT-PCR (inserts). The results show that aiRNA has no effect on the antisense Stat3 mRNAs while siRNA does (FIG. 15d). This result demonstrate aiRNA completely abolish the undesired non-specific gene-silencing mediated by the sense strand-RISC complex.

Figure 15F:
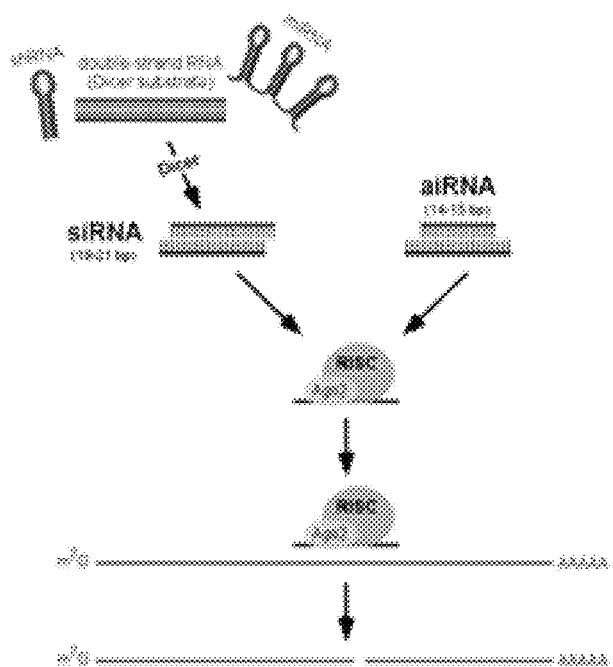

In summary, we have shown that aiRNA is a novel class of gene-silencing inducers, the non-siRNA type and the smallest structural scaffold for RISC substrates and RNAi mediators (FIG. 15f). Our data suggest that aiRNA works through RISC, the cellular RNAi machinery. After incorporation into RISC, aiRNA mediates sequence-specific cleavage of the mRNA between base 10 and 11 relative to the 5' end of the aiRNA antisense strand. The asymmetrical configuration of aiRNA can interact more efficiently with RISC than siRNA. Consistent with high RISC binding efficiency, aiRNA is more potent, efficacious, rapid-onset, and durable than siRNA in mediating gene-specific silencing against genes tested in our study. While previous studies have proposed a role of Dicer in facilitating efficient RISC formation, our data suggest aiRNA can give rise to active RISC complexes with high efficiency independent of Dicer-mediated processing.

The key feature of this novel RNA duplex scaffold is antisense overhangs at the 3' and 5' ends. The 12-15 bp aiRNA are the shortest RNA duplex known to induce RNAi. While long dsRNAs triggered potent gene silencing in C. elegans and Drosophila Melanogaster, gene-specific silencing in mammalian cells was not possible until siRNA duplexes were used. The siRNA scaffold, as defined by Dicer digestion, is characterized by symmetry in strand lengths of 19-21 bp and 3' overhangs (Bernstein et al., 2001), which has been considered the essential structure for incorporating into RISC to mediate RNAi. Therefore, optimization efforts for RNAi inducers have been focused on siRNA precursors, which are invariably larger than siRNA (Soutschek et al., 2004; Zhang and Farwell, 2007). Our data suggest that siRNA is not the essential scaffold for incorporating into RISC to mediate RNAi. The aiRNAs of different lengths displayed a spectrum of gene silencing efficacy and RISC incorporation efficiency, offering unique opportunity for understanding the mechanism of RISC incorporation and activation. Research is needed to further understand the structure-activity relationship of aiRNAs in RISC incorporation and RNAi induction, which should help establish a rational basis for optimizing aiRNAs with regards to target sequence selection, length, structure, chemical composition and modifications for various RNAi applications.

Example 5. aiRNA is More Efficacious than siRNA In Vivo

To investigate if aiRNA is efficacious in vivo and to compare it with siRNA, we tested the effects of aiRNA and siRNA in human colon cancer xenograft models.

Human Colon Cancer is the second leading cause of cancer death in the U.S. The Wnt β-catenin signaling pathway is tightly regulated and has important functions in development, tissue homeostasis, and regeneration. Deregulation of Wnt/β-catenin signaling is frequently found in various human cancers. Eighty percent of colorectal cancers alone reveal activation of this pathway by either inactivation of the tumor-suppressor gene adenomatous polyposis coli or mutation of the proto-oncogene β-catenin.

Activation of Wnt/β-catenin signaling has been found to be important for both initiation and progression of cancers of different tissues. Therefore, targeted inhibition of Wnt/β-catenin signaling is a rational and promising new approach for the therapy of cancers of various origins.

In vitro, by ribozyme-targeting we have demonstrated the reduction of β-catenin expression in human colon cancer SW480 cells and associated induction of cell death, indicating that β-catenin expression is rate-limiting for tumor growth in vitro.

SW480 human colon cancer cells were inoculated subcutaneously into female athymic nude mice ($8 \times 10^6$ cells/mouse) and allowed to form palpable tumors. In this study, dosing began when the tumors reached approximately 120 mm$^3$. Animals were treated intravenously (iv) with 0.6 nmol PEI-complexed β-catenin siRNAs, PEI-complexed β-catenin aiRNAs or a PEI-complexed unrelated siRNA as a negative control daily. The animals received a total of 10 doses of siRNA, aiRNA or control. Tumors were measured throughout treatment. As shown in FIG. 16, intravenous treatment with siRNA and aiRNA as a monotherapy at 0.6 nmol mg/kg significantly inhibited tumor growth. The % T/C value of siRNA was calculated to be 48.8% with a p value of 0.0286. The treatment with the β-catenin-specific aiRNAs, however, resulted in a much more potent reduction in tumor growth. The % T/C value was calculated to be 9.9% with a p value of 0.0024. There was no significant change in body weight due to iv administration of the siRNA, aiRNA or control. These data suggest that the systemic in vivo application of aiRNAs through PEI complexation upon targeting of the β-catenin offers an avenue for the development of highly efficient, specific and safe agents for therapeutic applications for patients with colon cancer.

In addition, we also tested the effects of aiRNA and siRNA in HT29 human colon cancer xenograft model. HT29 human colon cancer cells were inoculated subcutaneously into female athymic nude mice ($6 \times 10^6$ cells/mouse) and allowed to form palpable tumors. In this study, dosing began when the tumors reached approximately 200 mm$^3$. Animals were treated intravenously (iv) with 0.6 nmol PEI-complexed β-catenin siRNAs, PEI-complexed β-catenin aiRNAs or a PEI-complexed unrelated siRNA as a negative control every other day. The animals received a total of 8 doses of siRNA, aiRNA or control. Tumors were measured throughout treatment. As shown in FIG. 17, intravenous treatment with siRNA and aiRNA as a monotherapy at 0.6 nmol mg/kg significantly inhibited tumor growth. The % T/C value of siRNA was calculated to be 78% with a p value of 0.21. Again, the treatment with the β-catenin-specific aiRNAs resulted in an even more potent reduction in tumor growth. The % T/C value was calculated to be 41% with a p value of 0.016. There was no significant change in body weight due to iv administration of the siRNA, aiRNA or control. These data second that the systemic in vivo application of aiRNAs through PEI complexation upon targeting of the β-catenin offers an avenue for the development of highly efficient, specific and safe agents for therapeutic applications for patients with colon cancer.

Together, the aiRNA may significantly improve broad RNAi applications. The siRNA-based therapeutics have met with challenges, including limited efficacy, delivery difficulty, interferon-like responses and manufacture cost (de Fougerolles et al., 2007; Iorns et al., 2007; Rana, 2007). The improved efficacy, potency, durability, and smaller size of aiRNAs may help or overcome these challenges since aiRNA is smaller and may need less material for its delivery. Therefore, aiRNA represents new and smallest RNA duplexes that enter RISC and mediates gene silencing of better efficacy, potency, onset of action, and durability than siRNA in mammalian cells, holding significant potential for broad RNAi applications in gene function study and RNAi-based therapies.

Other embodiments are within the following claims. While several embodiments have been shown and described, various modifications may be made without departing from the spirit and scope of the present invention. Sequence listings and related materials in the ASCII text file named "2018-0430_SEQ_GHI-012US2_ST25.txt" and created on Apr. 30, 2018 with a size of about 38 kilobytes, is hereby incorporated by reference.

REFERENCES

Bernstein, E., Caudy, A. A., Hammond, S. M., and Hannon, G. J. (2001). Role for a bidentate ribonuclease in the initiation step of RNA interference. Nature 409, 363-366.

Chiu, Y. L., and Rana, T. M. (2003). siRNA function in RNAi: a chemical modification analysis. RNA (New York, N.Y. 9, 1034-1048.

Clevers, H. (2006). Wnt/beta-catenin signaling in development and disease. Cell 127, 469-480.

Czauderna, F., Fechtner, M., Dames, S., Aygun, H., Klippel, A., Pronk, G. J., Giese, K., and Kaufmann, J. (2003). Structural variations and stabilising modifications of synthetic siRNAs in mammalian cells. Nucleic acids research 31, 2705-2716.

Czech, M. P. (2006). MicroRNAs as therapeutic targets. The New England journal of medicine 354, 1194-1195.

de Fougerolles, A., Vornlocher, H. P., Maraganore, J., and Lieberman, J. (2007). Interfering with disease: a progress report on siRNA-based therapeutics. Nat Rev Drug Discov 6, 443-453.

Dignam, J. D., Lebovitz, R. M., and Roeder, R. G. (1983). Accurate transcription initiation by RNA polymerase II in a soluble extract from isolated mammalian nuclei. Nucleic acids research 11, 1475-1489.

Donze, O., and Picard, D. (2002). RNA interference in mammalian cells using siRNAs synthesized with T7 RNA polymerase. Nucleic Acids Res 30, e46.

Dykxhoorn, D. M., Novina, C. D., and Sharp, P. A. (2003). Killing the messenger: short RNAs that silence gene expression. Nat Rev Mol Cell Biol 4, 457-467.

Elbashir, S. M., Harborth, J., Lendeckel, W., Yalcin, A., Weber, K., and Tuschl, T. (2001a). Duplexes of 21-nucleotide RNAs mediate RNA interference in cultured mammalian cells. Nature 411, 494-498.

Elbashir, S. M., Lendeckel, W., and Tuschl, T. (2001b). RNA interference is mediated by 21- and 22-nucleotide RNAs. Genes Dev 15, 188-200.

Elbashir, S. M., Martinez, J., Patkaniowska, A., Lendeckel, W., and Tuschl, T. (2001c). Functional anatomy of siRNAs for mediating efficient RNAi in Drosophila melanogaster embryo lysate. Embo J 20, 6877-6888.

Eulalio, A., Huntzinger, E., and Izaurralde, E. (2008). Getting to the root of miRNA-mediated gene silencing. Cell 132, 9-14.

Fire, A., Xu, S., Montgomery, M. K., Kostas, S. A., Driver, S. E., and Mello, C. C. (1998). Potent and specific genetic interference by double-stranded RNA in Caenorhabditis elegans. Nature 391, 806-811.

Hammond, S. M., Bernstein, E., Beach, D., and Hannon, G. J. (2000). An RNA-directed nuclease mediates post-transcriptional gene silencing in Drosophila cells. Nature 404, 293-296.

Hammond, S. M., Boettcher, S., Caudy, A. A., Kobayashi, R., and Hannon, G. J. (2001). Argonaute2, a link between genetic and biochemical analyses of RNAi. Science 293, 1146-1150.

Iorns, E., Lord, C. J., Turner, N., and Ashworth, A. (2007). Utilizing RNA interference to enhance cancer drug discovery. Nature reviews 6, 556-568.

Kim, D. H., Behlke, M. A., Rose, S. D., Chang, M. S., Choi, S., and Rossi, J. J. (2005). Synthetic dsRNA Dicer substrates enhance RNAi potency and efficacy. Nat Biotechnol 23, 222-226.

Kim, D. H., and Rossi, J. J. (2007). Strategies for silencing human disease using RNA interference. Nature reviews 8, 173-184.

Liu, J., Carmell, M. A., Rivas, F. V., Marsden, C. G., Thomson, J. M., Song, J. J., Hammond, S. M., Joshua-Tor, L., and Hannon, G. J. (2004). Argonaute2 is the catalytic engine of mammalian RNAi. Science 305, 1437-1441.

Mack, G. S. (2007). MicroRNA gets down to business. Nature biotechnology 25, 631-638.

Martinez, J., and Tuschl, T. (2004). RISC is a 5' phosphomonoester-producing RNA endonuclease. Genes Dev 18, 975-980.

Matranga, C., Tomari, Y., Shin, C., Bartel, D. P., and Zamore, P. D. (2005). Passenger-strand cleavage facilitates assembly of siRNA into Ago2-containing RNAi enzyme complexes. Cell 123, 607-620.

Paddison, P. J., Caudy, A. A., Bernstein, E., Hannon, G. J., and Conklin, D. S. (2002). Short hairpin RNAs (shRNAs) induce sequence-specific silencing in mammalian cells. Genes Dev 16, 948-958.

Patzel, V. (2007). In silico selection of active siRNA. Drug discovery today 12, 139-148.

Rana, T. M. (2007). Illuminating the silence: understanding the structure and function of small RNAs. Nat Rev Mol Cell Biol 8, 23-36.

Rogoff, H. A., Pickering, M. T., Frame, F. M., Debatis, M. E., Sanchez, Y., Jones, S., and Kowalik, T. F. (2004). Apoptosis associated with deregulated E2F activity is dependent on E2F1 and Atm/Nbs1/Chk2. Mol Cell Biol 24, 2968-2977.

Siolas, D., Lerner, C., Burchard, J., Ge, W., Linsley, P. S., Paddison, P. J., Hannon, G. J., and Cleary, M. A. (2005). Synthetic shRNAs as potent RNAi triggers. Nat Biotechnol 23, 227-231.

Sledz, C. A., Holko, M., de Veer, M. J., Silverman, R. H., and Williams, B. R. (2003). Activation of the interferon system by short-interfering RNAs. Nat Cell Biol 5, 834-839.

Soutschek, J., Akinc, A., Bramlage, B., Charisse, K., Constien, R., Donoghue, M., Elbashir, S., Geick, A., Hadwiger, P., Harborth, J., et al. (2004). Therapeutic silencing of an endogenous gene by systemic administration of modified siRNAs. Nature 432, 173-178.

Tabara, H., Sarkissian, M., Kelly, W. G., Fleenor, J., Grishok, A., Timmons, L., Fire, A., and Mello, C. C. (1999). The rde-1 gene, RNA interference, and transposon silencing in *C. elegans*. Cell 99, 123-132.

Xiang, S., Fruehauf, J., and Li, C. J. (2006). Short hairpin RNA-expressing bacteria elicit RNA interference in mammals. Nature biotechnology 24, 697-702.

Zamore, P. D., and Aronin, N. (2003). siRNAs knock down hepatitis. Nature medicine 9, 266-267.

Zamore, P. D., Tuschl, T., Sharp, P. A., and Bartel, D. P. (2000). RNAi: double-stranded RNA directs the ATP-dependent cleavage of mRNA at 21 to 23 nucleotide intervals. Cell 101, 25-33.

Zhang, B., and Farwell, M. A. (2007). microRNAs: a new emerging class of players for disease diagnostics and gene therapy. J Cell Mol Med.

Zhang, N.Y., Du, Q., Wahlestedt, C., and Liang, Z. (2006). RNA Interference with chemically modified siRNA. Current topics in medicinal chemistry 6, 893-900.

What is claimed is:

1. A method for preparing an asymmetric interfering RNA duplex comprising combining a sense oligonucleotide consisting of 14, 15, 16 or 17 nucleotides and an antisense oligonucleotide consisting of 19, 20, 21, 22 or 23 nucleotides,
   wherein the antisense oligonucleotide includes a 3'-overhang of 1, 2, 3, 4, 5, 6, 7, 8 or 9 nucleotides and a 5'-overhang of 0, 1, 2, 3, 4, 5, 6, 7 or 8 nucleotides, and having a sequence that is at least 70% complementary to an expressed nucleotide sequence of a target gene and has a last nucleotide at its 3' end consisting of an A, U, G or C ribonucleotide,
   wherein 10, 11, 12, 13, 14, 15, 16, or 17 bases of the sense oligonucleotide are complementary with bases in the antisense oligonucleotide to form a double-stranded region, and at least the first base and last base of the sense oligonucleotide base pair with bases of the antisense oligonucleotide, and
   wherein the sense oligonucleotide of the RNA duplex does not substantially mediate off-target silencing.

2. The method of claim 1, wherein the RNA duplex is more effective at silencing the expressed nucleotide sequence of the target gene than a corresponding 21-mer siRNA duplex targeting the same expressed nucleotide sequence of the target gene.

3. The method of claim 1, wherein the RNA duplex does not induce an interferon response.

4. The method of claim 1, wherein the antisense oligonucleotide comprises a 5'-overhang consisting of 0, 1, 2, 3, 4, or 5.

5. The method of claim 1, wherein the antisense oligonucleotide comprises a 3'-overhang consisting of 2, 3, 4, 5, or 6.

6. The method of claim 1, wherein the last base of the sense oligonucleotide base pairs with the first base of the antisense oligonucleotide.

7. The method of claim 1, wherein the bases in the antisense oligonucleotide that are complementary to the expressed nucleotide sequence of the target gene have a GC content ranging from 38.9% to 43%.

8. The method of claim 1, wherein the bases in the antisense oligonucleotide that are complementary to the expressed nucleotide sequence of the target gene have a GC content of about 43%.

9. The method of claim 1, wherein the sense oligonucleotide consists of 15 nucleotides.

10. The method of claim 1, wherein the antisense oligonucleotide consists of 21 nucleotides.

11. The method of claim 1, wherein the antisense oligonucleotide consists of 19, 20 or 21 nucleotides.

12. The method of claim 1, wherein the double-stranded region comprises at least one unmatched or mismatched base.

13. The method of claim 1, wherein 16, 17, 18, 19, 20 or 21 bases of the antisense oligonucleotide are complementary to the expressed nucleotide sequence of the target gene.

14. The method of claim 1, wherein the last nucleotide at the 3' end of the antisense oligonucleotide consists of a sugar- and/or backbone-modified A, U, G or C ribonucleotide and/or a base-modified A, G or C ribonucleotide.

15. The method of claim 1, wherein at least one of the sense oligonucleotide and the antisense oligonucleotide comprises at least one modified nucleotide or its analogue.

16. The method of claim 15, wherein the at least one modified nucleotide or its analogue is a sugar-, backbone-, and/or base-modified ribonucleotide.

17. The method of claim 16, wherein the backbone-modified ribonucleotide has a modification in a phosphodiester linkage that links it with another ribonucleotide.

18. The method of claim 17, wherein the phosphodiester linkage is modified to include at least one of a nitrogen or sulphur heteroatom.

19. The method of claim 15, wherein the at least one modified nucleotide or its analogue is a modified base.

20. The method of claim 15, wherein the at least one modified nucleotide or its analogue comprises an inosine or tritylated base.

21. The method of claim 15, wherein the at least one modified nucleotide or its analogue is a sugar-modified ribonucleotide in which the 2'-OH is replaced by H, OR, R, halo, SH, SR, $NH_2$, NHR, $NR_2$, or CN, wherein each R is independently $C_1$-$C_6$ alkyl, alkenyl or alkynyl, and the halo is F, Cl, Br or I.

22. The method of claim 15, wherein the at least one modified nucleotide or its analogue is a backbone-modified ribonucleotide containing a phosphothioate group.

23. The method of claim 15, wherein at least one of the sense oligonucleotide and the antisense oligonucleotide further comprises at least one deoxynucleotide.

24. The method of claim 1, wherein the RNA duplex molecule further comprises a peptide, an antibody, a polymer, a lipid, another oligonucleotide, cholesterol, or an aptamer.

25. The method of claim 1, wherein the sense oligonucleotide and/or antisense oligonucleotide is bound to a lipid or a cholesterol molecule.

26. The method of claim 25, wherein the lipid or cholesterol molecule is conjugated to the RNA duplex molecule.

27. The method of claim 1, wherein the antisense oligonucleotide comprises a 3'-overhang of 2-4 nucleotides and a 5'-overhang of 2-4 nucleotides.

28. The method of claim 1, wherein the antisense oligonucleotide comprises a 3'-overhang of 1-9 nucleotides and a 5'-blunt end.

29. The method of claim 1, wherein at least one nucleotide of the 5'-overhang of the antisense oligonucleotide is A, U or dT.

30. The method of claim 1, wherein the 5'-overhang of the antisense oligonucleotide comprises an AA motif.

31. The method of claim 1, wherein the target gene is:
a) a gene associated with human or animal diseases,
b) a gene of a pathogenic microorganism,
c) a viral gene,
d) a tumor-associated gene, or
e) a gene associated with a disease selected from the group selected from the group consisting of autoimmune diseases, inflammatory diseases, degenerative diseases, infectious diseases, proliferative diseases, metabolic diseases, immune-mediated disorders, allergic diseases, dermatological diseases, malignant diseases, gastrointestinal disorders, respiratory disorders, cardiovascular disorders, renal disorders, rheumatoid disorders, neurological disorders, endocrine disorders, and aging.

32. The method of claim 21, wherein the 2'-OH is replaced by a 2'-O-methyl group.

* * * * *

```
                         SEQUENCE LISTING

<160> NUMBER OF SEQ ID NOS: 172

<210> SEQ ID NO 1
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 1
uucgaaguau uccgcguacg u                                              21

<210> SEQ ID NO 2
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 2
ucgaaguauu ccgcguacgu g                                              21

<210> SEQ ID NO 3
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 3
cgaaguauuc cgcguacgug a                                              21

<210> SEQ ID NO 4
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 4
augcuguguu aacug                                                     15

<210> SEQ ID NO 5
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 5
aagcaguuaa cacagcauga u                                              21

<210> SEQ ID NO 6
<211> LENGTH: 15
```

```
<212> TYPE: RNA
<213> ORGANISM: Artificial Sequence
<220> FEATURE:
<223> OTHER INFORMATION: Strand of duplex RNA

<400> SEQUENCE: 6
ccucuuauga uguau                                                          15

<210> SEQ ID NO 7
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 7
aauauacauc auaagagggc c                                                   21

<210> SEQ ID NO 8
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 8
agcaaagaau cacau                                                          15

<210> SEQ ID NO 9
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 9
aacaugugau ucuuugcugg c                                                   21

<210> SEQ ID NO 10
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 10
gaaucucaac uucag                                                          15

<210> SEQ ID NO 11
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 11
aaucugaagu ugagauucug c                                                   21

<210> SEQ ID NO 12
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 12
```
uaaaggugaa gauau          15

<210> SEQ ID NO 13
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 13
aauauaucuu caccuuuagc u          21

<210> SEQ ID NO 14
<211> LENGTH: 15
<212> TYPE: RNA
<213> ORGANISM: Artificial Sequence
<220> FEATURE:
<223> OTHER INFORMATION: RNA strand

<400> SEQUENCE: 14
uguuugauuu ggauu          15

<210> SEQ ID NO 15
<211> LENGTH: 21
<212> TYPE: RNA
<213> ORGANISM: Artificial
<220> FEATURE:
<223> OTHER INFORMATION: synthetic

<400> SEQUENCE: 15
aaaaauccaa aucaaacacg g          21

<210> SEQ ID NO 16
<211> LENGTH: 15
<212> TYPE: RNA
<213> ORGANISM: Artificial
<220> FEATURE:
<223> OTHER INFORMATION: Synthetic

<400> SEQUENCE: 16
gaauugucaa gggau          15

<210> SEQ ID NO 17
<211> LENGTH: 21
<212> TYPE: RNA
<213> ORGANISM: Artificial
<220> FEATURE:
<223> OTHER INFORMATION: Synthetic

<400> SEQUENCE: 17
aauaucccuu gacaauucug c          21

<210> SEQ ID NO 18
<211> LENGTH: 15
<212> TYPE: RNA
<213> ORGANISM: Artificial
<220> FEATURE:
<223> OTHER INFORMATION: Synthetic

<400> SEQUENCE: 18
aauuggaaca caguu          15

<210> SEQ ID NO 19
<211> LENGTH: 21
<212> TYPE: RNA
<213> ORGANISM: Artificial

```
<220> FEATURE:
<223> OTHER INFORMATION: Synthetic

<400> SEQUENCE: 19
aaaaacugug uuccauuuc c                                              21

<210> SEQ ID NO 20
<211> LENGTH: 15
<212> TYPE: RNA
<213> ORGANISM: Artificial
<220> FEATURE:
<223> OTHER INFORMATION: Synthetic

<400> SEQUENCE: 20
agaugcuguu guaau                                                    15

<210> SEQ ID NO 21
<211> LENGTH: 21
<212> TYPE: RNA
<213> ORGANISM: Artificial
<220> FEATURE:
<223> OTHER INFORMATION: Synthetic

<400> SEQUENCE: 21
aaaauuacaa cagcaucucc a                                             21

<210> SEQ ID NO 22
<211> LENGTH: 15
<212> TYPE: RNA
<213> ORGANISM: Artificial Sequence
<220> FEATURE:
<223> OTHER INFORMATION: GeneRacer RNA adaptor

<400> SEQUENCE: 22
gcgaagaaga aaucu                                                    15

<210> SEQ ID NO 23
<211> LENGTH: 21
<212> TYPE: RNA
<213> ORGANISM: Artificial
<220> FEATURE:
<223> OTHER INFORMATION: Synthetic

<400> SEQUENCE: 23
aauagauuuc uucuucgcca c                                             21

<210> SEQ ID NO 24
<211> LENGTH: 15
<212> TYPE: RNA
<213> ORGANISM: Artificial
<220> FEATURE:
<223> OTHER INFORMATION: Synthetic

<400> SEQUENCE: 24
aggagaucaa cauuu                                                    15

<210> SEQ ID NO 25
<211> LENGTH: 21
<212> TYPE: DNA
<213> ORGANISM: Artificial Sequence
<220> FEATURE:
<223> OTHER INFORMATION: Strand of duplex RNA

<400> SEQUENCE: 25
ugaaaauguu gaucuccuut t                                             21
```

```
<210> SEQ ID NO 26
<211> LENGTH: 15
<212> TYPE: RNA
<213> ORGANISM: Artificial Sequence
<220> FEATURE:
<223> OTHER INFORMATION: Strand of RNA duplex

<400> SEQUENCE: 26
gcagaccuug ugaua                                                    15

<210> SEQ ID NO 27
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 27
aaauaucaca aggucugcgg c                                             21

<210> SEQ ID NO 28
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 28
cccgcucuac aucuu                                                    15

<210> SEQ ID NO 29
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 29
aagaagaugu agagcgggcc u                                             21

<210> SEQ ID NO 30
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 30
ggcgguugaa ugaga                                                    15

<210> SEQ ID NO 31
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 31
aacucucauu caaccgccua g                                             21

<210> SEQ ID NO 32
<211> LENGTH: 15
<212> TYPE: RNA
<213> ORGANISM: Artificial Sequence
<220> FEATURE:
<223> OTHER INFORMATION: Strand of duplex RNA
```

```
<400> SEQUENCE: 32
ggagcuguug gcgua                                                         15

<210> SEQ ID NO 33
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 33
aacuacgcca acagcuccaa c                                                  21

<210> SEQ ID NO 34
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 34
gcugauauug augga                                                         15

<210> SEQ ID NO 35
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 35
aaguccauca auaucagcua c                                                  21

<210> SEQ ID NO 36
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 36
gauauugaug gacuu                                                         15

<210> SEQ ID NO 37
<211> LENGTH: 20
<212> TYPE: RNA
<213> ORGANISM: Artificial Sequence
<220> FEATURE:
<223> OTHER INFORMATION: Strand of duplex RNA

<400> SEQUENCE: 37
aaguccauca auaucagcua                                                    20

<210> SEQ ID NO 38
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 38
cugauauuga uggac                                                         15

<210> SEQ ID NO 39
```

```
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 39
aaguccauca auaucagcua c                                              21

<210> SEQ ID NO 40
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 40
agcugauauu gaugg                                                     15

<210> SEQ ID NO 41
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 41
uagcugauau ugaug                                                     15

<210> SEQ ID NO 42
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 42
ugauauugau ggacu                                                     15

<210> SEQ ID NO 43
<211> LENGTH: 22
<212> TYPE: RNA
<213> ORGANISM: Artificial Sequence
<220> FEATURE:
<223> OTHER INFORMATION: Strand of duplex RNA

<400> SEQUENCE: 43
aaguccauca auaucagcua cu                                             22

<210> SEQ ID NO 44
<211> LENGTH: 16
<212> TYPE: RNA
<213> ORGANISM: Artificial Sequence
<220> FEATURE:
<223> OTHER INFORMATION: Strand of duplex RNA

<400> SEQUENCE: 44
gcugauauug auggac                                                    16

<210> SEQ ID NO 45
<211> LENGTH: 16
<212> TYPE: RNA
<213> ORGANISM: Artificial Sequence
<220> FEATURE:
<223> OTHER INFORMATION: Strand of duplex RNA

<400> SEQUENCE: 45
```
agcugauauu gaugga                                                    16

<210> SEQ ID NO 46
<211> LENGTH: 17
<212> TYPE: RNA
<213> ORGANISM: Artificial Sequence
<220> FEATURE:
<223> OTHER INFORMATION: Strand of duplex RNA

<400> SEQUENCE: 46
agcugauauu gauggac                                                   17

<210> SEQ ID NO 47
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 47
agcugauauu gauggacu                                                  18

<210> SEQ ID NO 48
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 48
uagcugauau ugauggac                                                  18

<210> SEQ ID NO 49
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 49
gcugauauug auggacuu                                                  18

<210> SEQ ID NO 50
<211> LENGTH: 19
<212> TYPE: RNA
<213> ORGANISM: Artificial Sequence
<220> FEATURE:
<223> OTHER INFORMATION: Strand of duplex RNA

<400> SEQUENCE: 50
agcugauauu gauggacuu                                                 19

<210> SEQ ID NO 51
<211> LENGTH: 19
<212> TYPE: RNA
<213> ORGANISM: Artificial Sequence
<220> FEATURE:
<223> OTHER INFORMATION: Strand of duplex RNA

<400> SEQUENCE: 51
uagcugauau ugauggacu                                                 19

<210> SEQ ID NO 52
<211> LENGTH: 20
<212> TYPE: RNA

```
<213> ORGANISM: Artificial Sequence
<220> FEATURE:
<223> OTHER INFORMATION: Strand of duplex RNA

<400> SEQUENCE: 52
uagcugauau ugauggacuu                                                        20

<210> SEQ ID NO 53
<211> LENGTH: 20
<212> TYPE: RNA
<213> ORGANISM: Artificial Sequence
<220> FEATURE:
<223> OTHER INFORMATION: Strand of duplex RNA

<400> SEQUENCE: 53
guagcugaua uugauggacu                                                        20

<210> SEQ ID NO 54
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 54
gcugauauug aagga                                                             15

<210> SEQ ID NO 55
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 55
cuguccauca auaucagcua c                                                      21

<210> SEQ ID NO 56
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(3)
<223> OTHER INFORMATION: deoxynucleotides
<220> FEATURE:
<221> NAME/KEY: misc_feature
<222> LOCATION: (4)..(21)
<223> OTHER INFORMATION: nucleotides

<400> SEQUENCE: 56
aaguccauca auaucagcua c                                                      21

<210> SEQ ID NO 57
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(18)
<223> OTHER INFORMATION: nucleotides
<220> FEATURE:
<221> NAME/KEY: misc_feature
<222> LOCATION: (19)..(21)
<223> OTHER INFORMATION: deoxynucleotides
```

<400> SEQUENCE: 57
aaguccauca auaucagcta c                                              21

<210> SEQ ID NO 58
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(1)
<223> OTHER INFORMATION: deoxynucleotide
<220> FEATURE:
<221> NAME/KEY: misc_feature
<222> LOCATION: (2)..(15)
<223> OTHER INFORMATION: nucleotides

<400> SEQUENCE: 58
gcugauauug augga                                                     15

<210> SEQ ID NO 59
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(14)
<223> OTHER INFORMATION: nucleotides
<220> FEATURE:
<221> NAME/KEY: misc_feature
<222> LOCATION: (15)..(15)
<223> OTHER INFORMATION: deoxynucleotides

<400> SEQUENCE: 59
gcugauauug augga                                                     15

<210> SEQ ID NO 60
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 60
cguacgcgga auacuucg                                                  18

<210> SEQ ID NO 61
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 61
uucgaaguau uccgcguacg u                                              21

<210> SEQ ID NO 62
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 62
ucgaaguauu ccgcguacgu g                                         21

<210> SEQ ID NO 63
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 63
cgaaguauuc cgcguacgug a                                         21

<210> SEQ ID NO 64
<211> LENGTH: 19
<212> TYPE: RNA
<213> ORGANISM: Artificial Sequence
<220> FEATURE:
<223> OTHER INFORMATION: Strand of duplex RNA

<400> SEQUENCE: 64
cguacgcgga auacuucga                                            19

<210> SEQ ID NO 65
<211> LENGTH: 20
<212> TYPE: RNA
<213> ORGANISM: Artificial Sequence
<220> FEATURE:
<223> OTHER INFORMATION: Strand of duplex RNA

<400> SEQUENCE: 65
cguacgcgga auacuucgaa                                           20

<210> SEQ ID NO 66
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 66
cguacgcgga auacuucgaa a                                         21

<210> SEQ ID NO 67
<211> LENGTH: 22
<212> TYPE: RNA
<213> ORGANISM: Artificial Sequence
<220> FEATURE:
<223> OTHER INFORMATION: Strand of duplex RNA

<400> SEQUENCE: 67
cguacgcgga auacuucgaa au                                        22

<210> SEQ ID NO 68
<211> LENGTH: 23
<212> TYPE: RNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (20)..(21)
<223> OTHER INFORMATION: n = deoxythymidine

<400> SEQUENCE: 68
cguacgcgga auacuucgaa aug                                       23

-continued

```
<210> SEQ ID NO 69
<211> LENGTH: 24
<212> TYPE: RNA
<213> ORGANISM: Artificial Sequence
<220> FEATURE:
<223> OTHER INFORMATION: Strand of duplex RNA

<400> SEQUENCE: 69
cguacgcgga auacuucgaa augu                                              24

<210> SEQ ID NO 70
<211> LENGTH: 25
<212> TYPE: RNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (20)..(21)
<223> OTHER INFORMATION: n = deoxythymidine

<400> SEQUENCE: 70
cguacgcgga auacuucgaa auguc                                             25

<210> SEQ ID NO 71
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 71
guagcugaua uugauggacu u                                                 21

<210> SEQ ID NO 72
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 72
uccaucaaua ucagc                                                        15

<210> SEQ ID NO 73
<211> LENGTH: 24
<212> TYPE: DNA
<213> ORGANISM: Artificial Sequence
<220> FEATURE:
<223> OTHER INFORMATION: Strand of duplex RNA

<400> SEQUENCE: 73
ggatctagaa tcagctacag cagc                                              24

<210> SEQ ID NO 74
<211> LENGTH: 24
<212> TYPE: DNA
<213> ORGANISM: Artificial Sequence
<220> FEATURE:
<223> OTHER INFORMATION: Strand of duplex RNA

<400> SEQUENCE: 74
tcctctagag ggcaatctcc attg                                              24

<210> SEQ ID NO 75
<211> LENGTH: 20
<212> TYPE: DNA
```

```
<213> ORGANISM: Artificial Sequence
<220> FEATURE:
<223> OTHER INFORMATION: Strand of duplex RNA

<400> SEQUENCE: 75
ccatggatga tgatatcgcc                                               20

<210> SEQ ID NO 76
<211> LENGTH: 20
<212> TYPE: DNA
<213> ORGANISM: Artificial Sequence
<220> FEATURE:
<223> OTHER INFORMATION: Strand of duplex RNA

<400> SEQUENCE: 76
tagaagcatt tgcggtggac                                               20

<210> SEQ ID NO 77
<211> LENGTH: 20
<212> TYPE: DNA
<213> ORGANISM: Artificial Sequence
<220> FEATURE:
<223> OTHER INFORMATION: Strand of duplex RNA

<400> SEQUENCE: 77
gacaatggct actcaagctg                                               20

<210> SEQ ID NO 78
<211> LENGTH: 20
<212> TYPE: DNA
<213> ORGANISM: Artificial Sequence
<220> FEATURE:
<223> OTHER INFORMATION: Strand of duplex RNA

<400> SEQUENCE: 78
caggtcagta tcaaaccagg                                               20

<210> SEQ ID NO 79
<211> LENGTH: 44
<212> TYPE: RNA
<213> ORGANISM: Artificial Sequence
<220> FEATURE:
<223> OTHER INFORMATION: Strand of duplex RNA

<400> SEQUENCE: 79
cgacuggagc acgaggacac ugacauggac ugaaggagua gaaa                    44

<210> SEQ ID NO 80
<211> LENGTH: 26
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (20)..(21)
<223> OTHER INFORMATION: n = deoxythymidine

<400> SEQUENCE: 80
ggacactgac atggactgaa ggagta                                        26

<210> SEQ ID NO 81
<211> LENGTH: 25
<212> TYPE: DNA
<213> ORGANISM: Artificial Sequence
<220> FEATURE:
<223> OTHER INFORMATION: Strand of duplex RNA
```

```
<400> SEQUENCE: 81
cgcatgatag cgtgtctgga agctt                                          25

<210> SEQ ID NO 82
<211> LENGTH: 21
<212> TYPE: DNA
<213> ORGANISM: Artificial Sequence
<220> FEATURE:
<223> OTHER INFORMATION: Strand of duplex RNA

<400> SEQUENCE: 82
guagcugaua uugauggact t                                              21

<210> SEQ ID NO 83
<211> LENGTH: 21
<212> TYPE: DNA
<213> ORGANISM: Artificial Sequence
<220> FEATURE:
<223> OTHER INFORMATION: Strand of duplex RNA

<400> SEQUENCE: 83
guccaucaau aucagcuact t                                              21

<210> SEQ ID NO 84
<211> LENGTH: 12
<212> TYPE: RNA
<213> ORGANISM: Artificial Sequence
<220> FEATURE:
<223> OTHER INFORMATION: Strand of duplex RNA

<400> SEQUENCE: 84
ugauauugau gg                                                        12

<210> SEQ ID NO 85
<211> LENGTH: 12
<212> TYPE: RNA
<213> ORGANISM: Artificial Sequence
<220> FEATURE:
<223> OTHER INFORMATION: Strand of duplex RNA

<400> SEQUENCE: 85
cugauauuga ug                                                        12

<210> SEQ ID NO 86
<211> LENGTH: 13
<212> TYPE: RNA
<213> ORGANISM: Artificial Sequence
<220> FEATURE:
<223> OTHER INFORMATION: Strand of duplex RNA

<400> SEQUENCE: 86
cugauauuga ugg                                                       13

<210> SEQ ID NO 87
<211> LENGTH: 14
<212> TYPE: RNA
<213> ORGANISM: Artificial Sequence
<220> FEATURE:
<223> OTHER INFORMATION: Strand of duplex RNA

<400> SEQUENCE: 87
gcugauauug augg                                                      14

<210> SEQ ID NO 88
```

```
<211> LENGTH: 14
<212> TYPE: RNA
<213> ORGANISM: Artificial Sequence
<220> FEATURE:
<223> OTHER INFORMATION: Strand of duplex RNA

<400> SEQUENCE: 88
cugauauuga ugga                                                         14

<210> SEQ ID NO 89
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 89
guagcugaua uugau                                                        15

<210> SEQ ID NO 90
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 90
aaguccauca auaucagc                                                     18

<210> SEQ ID NO 91
<211> LENGTH: 24
<212> TYPE: RNA
<213> ORGANISM: Artificial Sequence
<220> FEATURE:
<223> OTHER INFORMATION: Strand of duplex RNA

<400> SEQUENCE: 91
aauguccauc aauaucagcu acuu                                              24

<210> SEQ ID NO 92
<211> LENGTH: 24
<212> TYPE: RNA
<213> ORGANISM: Artificial Sequence
<220> FEATURE:
<223> OTHER INFORMATION: Strand of duplex RNA

<400> SEQUENCE: 92
aacuguccau caauaucagc uacu                                              24

<210> SEQ ID NO 93
<211> LENGTH: 27
<212> TYPE: RNA
<213> ORGANISM: Artificial Sequence
<220> FEATURE:
<223> OTHER INFORMATION: Strand of duplex RNA

<400> SEQUENCE: 93
auacugucca ucaauaucag cuacuug                                           27

<210> SEQ ID NO 94
<211> LENGTH: 20
<212> TYPE: RNA
<213> ORGANISM: Artificial Sequence
<220> FEATURE:
<223> OTHER INFORMATION: Strand of duplex RNA

<400> SEQUENCE: 94
```
aguccaucaa uaucagcuac    20

<210> SEQ ID NO 95
<211> LENGTH: 20
<212> TYPE: RNA
<213> ORGANISM: Artificial Sequence
<220> FEATURE:
<223> OTHER INFORMATION: Strand of duplex RNA

<400> SEQUENCE: 95
guccaucaau aucagcuacu    20

<210> SEQ ID NO 96
<211> LENGTH: 19
<212> TYPE: RNA
<213> ORGANISM: Artificial Sequence
<220> FEATURE:
<223> OTHER INFORMATION: Strand of duplex RNA

<400> SEQUENCE: 96
uccaucaaua ucagcuacu    19

<210> SEQ ID NO 97
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 97
guccaucaau aucagcua    18

<210> SEQ ID NO 98
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 98
uccaucaaua ucagcuac    18

<210> SEQ ID NO 99
<211> LENGTH: 17
<212> TYPE: RNA
<213> ORGANISM: Artificial Sequence
<220> FEATURE:
<223> OTHER INFORMATION: Strand of duplex RNA

<400> SEQUENCE: 99
uccaucaaua ucagcua    17

<210> SEQ ID NO 100
<211> LENGTH: 17
<212> TYPE: RNA
<213> ORGANISM: Artificial Sequence
<220> FEATURE:
<223> OTHER INFORMATION: Strand of duplex RNA

<400> SEQUENCE: 100
aguccaucaa uaucagc    17

<210> SEQ ID NO 101
<211> LENGTH: 19
<212> TYPE: RNA

<213> ORGANISM: Artificial Sequence
<220> FEATURE:
<223> OTHER INFORMATION: Strand of duplex RNA

<400> SEQUENCE: 101
guccaucaau aucagcuac					19

<210> SEQ ID NO 102
<211> LENGTH: 19
<212> TYPE: RNA
<213> ORGANISM: Artificial Sequence
<220> FEATURE:
<223> OTHER INFORMATION: Strand of duplex RNA

<400> SEQUENCE: 102
aguccaucaa uaucagcua					19

<210> SEQ ID NO 103
<211> LENGTH: 18
<212> TYPE: RNA
<213> ORGANISM: Artificial Sequence
<220> FEATURE:
<223> OTHER INFORMATION: Strand of duplex RNA

<400> SEQUENCE: 103
guagcugaua uugaugga					18

<210> SEQ ID NO 104
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 104
aaguccauca auaucugcua c					21

<210> SEQ ID NO 105
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(3)
<223> OTHER INFORMATION: deoxynucleotide
<220> FEATURE:
<221> NAME/KEY: misc_feature
<222> LOCATION: (4)..(18)
<223> OTHER INFORMATION: ribonucleotide
<220> FEATURE:
<221> NAME/KEY: misc_feature
<222> LOCATION: (19)..(21)
<223> OTHER INFORMATION: deoxynucleotide

<400> SEQUENCE: 105
aaguccauca auaucagcta c					21

<210> SEQ ID NO 106
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(1)
<223> OTHER INFORMATION: deoxynucleotide

```
<220> FEATURE:
<221> NAME/KEY: misc_feature
<222> LOCATION: (2)..(2)
<223> OTHER INFORMATION: ribonucleotide
<220> FEATURE:
<221> NAME/KEY: misc_feature
<222> LOCATION: (3)..(3)
<223> OTHER INFORMATION: deoxynucleotide
<220> FEATURE:
<221> NAME/KEY: misc_feature
<222> LOCATION: (4)..(10)
<223> OTHER INFORMATION: ribonucleotide
<220> FEATURE:
<221> NAME/KEY: misc_feature
<222> LOCATION: (11)..(11)
<223> OTHER INFORMATION: deoxynucleotide
<220> FEATURE:
<221> NAME/KEY: misc_feature
<222> LOCATION: (12)..(12)
<223> OTHER INFORMATION: ribonucleotide
<220> FEATURE:
<221> NAME/KEY: misc_feature
<222> LOCATION: (13)..(13)
<223> OTHER INFORMATION: deoxynucleotide
<220> FEATURE:
<221> NAME/KEY: misc_feature
<222> LOCATION: (14)..(14)
<223> OTHER INFORMATION: ribonucleotide
<220> FEATURE:
<221> NAME/KEY: misc_feature
<222> LOCATION: (15)..(15)
<223> OTHER INFORMATION: deoxynucleotide

<400> SEQUENCE: 106
gctgauauug augga                                                  15

<210> SEQ ID NO 107
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 107
guccaucaau aucagcuacu u                                           21

<210> SEQ ID NO 108
<211> LENGTH: 15
<212> TYPE: RNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(15)
<223> OTHER INFORMATION: n = ribonucleotide A, U, G, or C

<400> SEQUENCE: 108
nnnnnnnnnn nnnnn                                                  15

<210> SEQ ID NO 109
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(3)
<223> OTHER INFORMATION: any one of deoxynucleotides dA, dG, dT, and dC.
<220> FEATURE:
<221> NAME/KEY: misc_feature
<222> LOCATION: (4)..(21)
```

```
<223> OTHER INFORMATION: any one of ribonucleotides A, G, U and C.

<400> SEQUENCE: 109
nnnnnnnnnn nnnnnnnnn n                                            21

<210> SEQ ID NO 110
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(3)
<223> OTHER INFORMATION: any of deoxynucleotides dA, dG, dT and dC.
<220> FEATURE:
<221> NAME/KEY: misc_feature
<222> LOCATION: (4)..(18)
<223> OTHER INFORMATION: any of ribonucleotides A, G, U and C.
<220> FEATURE:
<221> NAME/KEY: misc_feature
<222> LOCATION: (19)..(21)
<223> OTHER INFORMATION: any of deoxynucleotides dA, dG, dT and dC.

<400> SEQUENCE: 110
nnnnnnnnnn nnnnnnnnn n                                            21

<210> SEQ ID NO 111
<211> LENGTH: 19
<212> TYPE: RNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(19)
<223> OTHER INFORMATION: n = ribonucleotide A, U, G, or C

<400> SEQUENCE: 111
nnnnnnnnnn nnnnnnnnn                                              19

<210> SEQ ID NO 112
<211> LENGTH: 21
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(18)
<223> OTHER INFORMATION: any of ribonucleotides A, G, U and C.
<220> FEATURE:
<221> NAME/KEY: misc_feature
<222> LOCATION: (19)..(21)
<223> OTHER INFORMATION: any of deoxynucleotides dA, dG, dT and dC.

<400> SEQUENCE: 112
nnnnnnnnnn nnnnnnnnn n                                            21

<210> SEQ ID NO 113
<211> LENGTH: 21
<212> TYPE: RNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(21)
<223> OTHER INFORMATION: n = ribonucleotide A, U, G, or C

<400> SEQUENCE: 113
```
nnnnnnnnnn nnnnnnnnn n                                             21

<210> SEQ ID NO 114
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(1)
<223> OTHER INFORMATION: any of deoxynucleotides dA, dG, dT and dC.
<220> FEATURE:
<221> NAME/KEY: misc_feature
<222> LOCATION: (2)..(15)
<223> OTHER INFORMATION: any of ribonucleotides A, G, U and C.

<400> SEQUENCE: 114
nnnnnnnnnn nnnnn                                                   15

<210> SEQ ID NO 115
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(14)
<223> OTHER INFORMATION: any of ribonucleotides A, G, U and C.
<220> FEATURE:
<221> NAME/KEY: misc_feature
<222> LOCATION: (15)..(15)
<223> OTHER INFORMATION: any of deoxynucleotides dA, dG, dT and dC.

<400> SEQUENCE: 115
nnnnnnnnnn nnnnn                                                   15

<210> SEQ ID NO 116
<211> LENGTH: 15
<212> TYPE: DNA
<213> ORGANISM: Artificial Sequence
<220> FEATURE:
<223> OTHER INFORMATION: Strand of duplex RNA
<220> FEATURE:
<221> NAME/KEY: misc_feature
<222> LOCATION: (1)..(1)
<223> OTHER INFORMATION: any of deoxynucleotides dA, dG, dT and dC.
<220> FEATURE:
<221> NAME/KEY: misc_feature
<222> LOCATION: (2)..(2)
<223> OTHER INFORMATION: any of ribonucleotides A, G, U and C.
<220> FEATURE:
<221> NAME/KEY: misc_feature
<222> LOCATION: (3)..(3)
<223> OTHER INFORMATION: any of deoxynucleotides dA, dG, dT and dC.
<220> FEATURE:
<221> NAME/KEY: misc_feature
<222> LOCATION: (4)..(10)
<223> OTHER INFORMATION: any of ribonucleotides A, G, U and C.
<220> FEATURE:
<221> NAME/KEY: misc_feature
<222> LOCATION: (11)..(11)
<223> OTHER INFORMATION: any of deoxynucleotides dA, dG, dT and dC.
<220> FEATURE:
<221> NAME/KEY: misc_feature
<222> LOCATION: (12)..(12)
<223> OTHER INFORMATION: any of ribonucleotides A, G, U and C.
<220> FEATURE:
<221> NAME/KEY: misc_feature
<222> LOCATION: (13)..(13)
<223> OTHER INFORMATION: any of deoxynucleotides dA, dG, dT and dC.
<220> FEATURE:

```
<221> NAME/KEY: misc_feature
<222> LOCATION: (14)..(14)
<223> OTHER INFORMATION: any of ribonucleotides A, G, U and C.
<220> FEATURE:
<221> NAME/KEY: misc_feature
<222> LOCATION: (15)..(15)
<223> OTHER INFORMATION: any of deoxynucleotides dA, dG, dT and dC.

<400> SEQUENCE: 116
nnnnnnnnnn nnnnn                                                           15

<210> SEQ ID NO 117
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 117
guagcugaua uugauggacu u                                                    21

<210> SEQ ID NO 118
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 118
guccaucaau aucagcuacu u                                                    21

<210> SEQ ID NO 119
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 119
gcugauauug augga                                                           15

<210> SEQ ID NO 120
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 120
aaguccauca auaucagcua c                                                    21

<210> SEQ ID NO 121
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 121
aucaugcugu guuaacugcu u                                                    21

<210> SEQ ID NO 122
<211> LENGTH: 21
<212> TYPE: RNA
<213> ORGANISM: Artificial Sequence
<220> FEATURE:
<223> OTHER INFORMATION: Strand of duplex RNA
```

```
<220> FEATURE:
<221> NAME/KEY: misc_feature
<222> LOCATION: (1)..(2)
<223> OTHER INFORMATION: n = deoxyadenosine
<220> FEATURE:
<221> NAME/KEY: misc_feature
<222> LOCATION: (3)..(3)
<223> OTHER INFORMATION: n = deoxyguanosine

<400> SEQUENCE: 122
gcaguuaaca cagcaugauu u                                              21

<210> SEQ ID NO 123
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 123
augcuguguu aacug                                                     15

<210> SEQ ID NO 124
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 124
aagcaguuaa cacagcauga u                                              21

<210> SEQ ID NO 125
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 125
ggcccucuua ugauguauau u                                              21

<210> SEQ ID NO 126
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 126
uauacaucau aagagggccu u                                              21

<210> SEQ ID NO 127
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 127
ccucuuauga uguau                                                     15

<210> SEQ ID NO 128
<211> LENGTH: 21
<212> TYPE: RNA
<213> ORGANISM: Artificial Sequence
<220> FEATURE:
```

```
<223> OTHER INFORMATION: Strand of duplex RNA

<400> SEQUENCE: 128
aauauacauc auaagagggc c                                             21

<210> SEQ ID NO 129
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 129
gccagcaaag aaucacaugu u                                             21

<210> SEQ ID NO 130
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 130
caugugauuc uuugcuggcu u                                             21

<210> SEQ ID NO 131
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 131
agcaaagaau cacau                                                    15

<210> SEQ ID NO 132
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 132
aacaugugau ucuuugcugg c                                             21

<210> SEQ ID NO 133
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 133
agcuaaaggu gaagauauau u                                             21

<210> SEQ ID NO 134
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 134
uauaucuuca ccuuuagcuu u                                             21
```

```
<210> SEQ ID NO 135
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 135
uaaaggugaa gauau                                                        15

<210> SEQ ID NO 136
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 136
aauauaucuu caccuuuagc u                                                 21

<210> SEQ ID NO 137
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 137
ccguguuuga uuuggauuuu u                                                 21

<210> SEQ ID NO 138
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 138
aaauccaaau caaacacggu u                                                 21

<210> SEQ ID NO 139
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 139
uguuugauuu ggauu                                                        15

<210> SEQ ID NO 140
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 140
aaaaauccaa aucaaacacg g                                                 21

<210> SEQ ID NO 141
<211> LENGTH: 21
<212> TYPE: RNA
<213> ORGANISM: Artificial Sequence
<220> FEATURE:
<223> OTHER INFORMATION: Strand of duplex RNA
```

```
<400> SEQUENCE: 141
gcagaauugu caagggauau u                                     21

<210> SEQ ID NO 142
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 142
uaucccuuga caauucugcu u                                     21

<210> SEQ ID NO 143
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 143
gaauugucaa gggau                                            15

<210> SEQ ID NO 144
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 144
aauaucccuu gacaauucug c                                     21

<210> SEQ ID NO 145
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 145
ggaaauugga acacaguuuu u                                     21

<210> SEQ ID NO 146
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 146
aaacuguguu ccaauuuccu u                                     21

<210> SEQ ID NO 147
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 147
aauuggaaca caguu                                            15

<210> SEQ ID NO 148
<211> LENGTH: 21
```

```
<212> TYPE: RNA
<213> ORGANISM: Artificial Sequence
<220> FEATURE:
<223> OTHER INFORMATION: Strand of duplex RNA

<400> SEQUENCE: 148
aaaaacugug uuccaauuuc c                                              21

<210> SEQ ID NO 149
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 149
uggagaugcu guuguaauuu u                                              21

<210> SEQ ID NO 150
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 150
aauuacaaca gcaucuccau u                                              21

<210> SEQ ID NO 151
<211> LENGTH: 15
<212> TYPE: RNA
<213> ORGANISM: Artificial Sequence
<220> FEATURE:
<223> OTHER INFORMATION: Strand of duplex RNA

<400> SEQUENCE: 151
agaugcuguu guaau                                                     15

<210> SEQ ID NO 152
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 152
aaaauuacaa cagcaucucc a                                              21

<210> SEQ ID NO 153
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 153
guggcgaaga agaaaucuau u                                              21

<210> SEQ ID NO 154
<211> LENGTH: 21
<212> TYPE: RNA
<213> ORGANISM: Artificial Sequence
<220> FEATURE:
<223> OTHER INFORMATION: Strand of duplex RNA

<400> SEQUENCE: 154
```

```
uagauuucuu cuucgccacu u                                              21

<210> SEQ ID NO 155
<211> LENGTH: 15
<212> TYPE: RNA
<213> ORGANISM: Artificial
<220> FEATURE:
<223> OTHER INFORMATION: duplex

<400> SEQUENCE: 155
gcgaagaaga aaucu                                                     15

<210> SEQ ID NO 156
<211> LENGTH: 21
<212> TYPE: RNA
<213> ORGANISM: Artificial
<220> FEATURE:
<223> OTHER INFORMATION: duplex

<400> SEQUENCE: 156
aauagauuuc uucuucgcca c                                              21

<210> SEQ ID NO 157
<211> LENGTH: 21
<212> TYPE: DNA
<213> ORGANISM: Artificial
<220> FEATURE:
<223> OTHER INFORMATION: Duplex
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxynucleotides

<400> SEQUENCE: 157
aaggagauca acauuuucat t                                              21

<210> SEQ ID NO 158
<211> LENGTH: 21
<212> TYPE: DNA
<213> ORGANISM: Artificial
<220> FEATURE:
<223> OTHER INFORMATION: Duplex
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxynucleotides

<400> SEQUENCE: 158
ugaaaauguu gaucuccuut t                                              21

<210> SEQ ID NO 159
<211> LENGTH: 15
<212> TYPE: RNA
<213> ORGANISM: Artificial
<220> FEATURE:
<223> OTHER INFORMATION: Duplex

<400> SEQUENCE: 159
aggagaucaa cauuu                                                     15
```

```
<210> SEQ ID NO 160
<211> LENGTH: 21
<212> TYPE: DNA
<213> ORGANISM: Artificial
<220> FEATURE:
<223> OTHER INFORMATION: duplex
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxynucleotides

<400> SEQUENCE: 160
ugaaaauguu gaucuccuut t                                              21

<210> SEQ ID NO 161
<211> LENGTH: 21
<212> TYPE: DNA
<213> ORGANISM: Artificial
<220> FEATURE:
<223> OTHER INFORMATION: Duplex
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxynucleotides

<400> SEQUENCE: 161
gccgcagacc uugugauaut t                                              21

<210> SEQ ID NO 162
<211> LENGTH: 21
<212> TYPE: DNA
<213> ORGANISM: Artificial
<220> FEATURE:
<223> OTHER INFORMATION: Duplex
<220> FEATURE:
<221> NAME/KEY: misc_feature
<222> LOCATION: (1)..(19)
<223> OTHER INFORMATION: ribonucleotides
<220> FEATURE:
<221> NAME/KEY: misc_feature
<222> LOCATION: (20)..(21)
<223> OTHER INFORMATION: deoxynucleotides

<400> SEQUENCE: 162
auaucacaag gucugcggct t                                              21

<210> SEQ ID NO 163
<211> LENGTH: 15
<212> TYPE: RNA
<213> ORGANISM: Artificial
<220> FEATURE:
<223> OTHER INFORMATION: Duplex

<400> SEQUENCE: 163
gcagaccuug ugaua                                                     15

<210> SEQ ID NO 164
<211> LENGTH: 21
<212> TYPE: RNA
<213> ORGANISM: Artificial
<220> FEATURE:
<223> OTHER INFORMATION: Duplex
```

-continued

```
<400> SEQUENCE: 164
aaauaucaca aggucugcgg c                                          21

<210> SEQ ID NO 165
<211> LENGTH: 21
<212> TYPE: RNA
<213> ORGANISM: Artificial
<220> FEATURE:
<223> OTHER INFORMATION: Duplex

<400> SEQUENCE: 165
aggcccgcuc uacaucuucu u                                          21

<210> SEQ ID NO 166
<211> LENGTH: 21
<212> TYPE: RNA
<213> ORGANISM: artificial
<220> FEATURE:
<223> OTHER INFORMATION: duplex

<400> SEQUENCE: 166
gaagauguag agcgggccuu u                                          21

<210> SEQ ID NO 167
<211> LENGTH: 15
<212> TYPE: RNA
<213> ORGANISM: Artificial
<220> FEATURE:
<223> OTHER INFORMATION: Duplex

<400> SEQUENCE: 167
cccgcucuac aucuu                                                 15

<210> SEQ ID NO 168
<211> LENGTH: 21
<212> TYPE: RNA
<213> ORGANISM: Artificial
<220> FEATURE:
<223> OTHER INFORMATION: Duplex

<400> SEQUENCE: 168
aagaagaugu agagcgggcc u                                          21

<210> SEQ ID NO 169
<211> LENGTH: 15
<212> TYPE: RNA
<213> ORGANISM: Artificial
<220> FEATURE:
<223> OTHER INFORMATION: Duplex

<400> SEQUENCE: 169
ggagcuguug gcgua                                                 15

<210> SEQ ID NO 170
<211> LENGTH: 21
<212> TYPE: RNA
<213> ORGANISM: Artificial
<220> FEATURE:
<223> OTHER INFORMATION: Duplex

<400> SEQUENCE: 170
aacuacgcca acagcuccaa c                                          21

<210> SEQ ID NO 171
<211> LENGTH: 21
```

```
<212> TYPE: RNA
<213> ORGANISM: Artificial
<220> FEATURE:
<223> OTHER INFORMATION: antisense probe

<400> SEQUENCE: 171
guagcugaua uugauggacu u                                      21

<210> SEQ ID NO 172
<211> LENGTH: 15
<212> TYPE: RNA
<213> ORGANISM: Artificial
<220> FEATURE:
<223> OTHER INFORMATION: sense probe

<400> SEQUENCE: 172
uccaucaaua ucagc                                             15
```